US012723030B2

(12) United States Patent
Silverman et al.

(10) Patent No.: US 12,723,030 B2
(45) Date of Patent: Sep. 1, 2026

(54) SELECTIVE NEURONAL NITRIC OXIDE SYNTHASE INHIBITORS

(71) Applicant: Northwestern University, Evanston, IL (US)

(72) Inventors: Richard B. Silverman, Winnetka, IL (US); Maris A. Cinelli, Evanston, IL (US); Cory T. Reidl, Northfield, IL (US)

(73) Assignee: Northwestern University, Evanston, IL (US)

( * ) Notice: Subject to any disclaimer, the term of this patent is extended or adjusted under 35 U.S.C. 154(b) by 1077 days.

(21) Appl. No.: 17/770,352

(22) PCT Filed: Oct. 26, 2020

(86) PCT No.: PCT/US2020/057417
§ 371 (c)(1),
(2) Date: Apr. 20, 2022

(87) PCT Pub. No.: WO2021/081528
PCT Pub. Date: Apr. 29, 2021

(65) Prior Publication Data

US 2022/0411377 A1 Dec. 29, 2022

Related U.S. Application Data

(60) Provisional application No. 62/926,178, filed on Oct. 25, 2019.

(51) Int. Cl.

| | |
|---|---|
| ***C07D 215/38*** | (2006.01) |
| ***C07D 401/04*** | (2006.01) |
| ***C07D 401/12*** | (2006.01) |
| ***C07D 413/12*** | (2006.01) |
| ***C07D 417/12*** | (2006.01) |

(52) U.S. Cl.
CPC ......... *C07D 215/38* (2013.01); *C07D 401/04* (2013.01); *C07D 401/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 2009/0209529 | A1 | 8/2009 | Andreini et al. |
| 2010/0273758 | A1 | 10/2010 | Brown et al. |

FOREIGN PATENT DOCUMENTS

| | | | |
|---|---|---|---|
| WO | 2008005457 | A2 | 1/2008 |
| WO | 2008057469 | A1 | 5/2008 |
| WO | 2008124092 | A3 | 12/2008 |
| WO | 2011054436 | A2 | 5/2011 |
| WO | 2011054841 | A1 | 5/2011 |
| WO | 2011128299 | A1 | 10/2011 |
| WO | 2011140325 | A1 | 11/2011 |
| WO | 2012148808 | A1 | 11/2012 |
| WO | 2016073623 | A2 | 12/2016 |

OTHER PUBLICATIONS

Database Registry Chemical Abstracts Service, Columbus, Ohio, Accession No. RN 1443142-18-4, Entered STN: Jul. 3, 2013.*

Adams, P. D.; Afonine, P. V.; Bunkoczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R.J.; Richardson, D. C.; Richardson, J. S.; Terwilliger, T. C.; Zwart, P. H. PHENIX: a comprehensive Python-based system for macromolecular structure solution. Acta Crystallogr., Sect. D: Biol. Crystallogr. 2010, 66, 213-221.

Ballatore, C.; Soper, J. H.; Piscitelli, F.; James, M.; Huang, L.; Atasoylu, O.; Huryn, D. M.; Trojanowski, J. Q.; Lee, V. M.; Brunden, K. R.; Smith, A. B. Cyclopentane-1,3-dione: a novel isostere for the carboxylic acid functional group. Application to the design of potent thromboxane (A2) receptor antagonists. J. Med. Chem. 2011, 54, 6969-6983.

Ballell, L.; Bates, R. H.; Young, R. J.; Alvarez-Gomez, D.; Alvarez-Ruiz, E.; Barroso, V.; Blanco, D.; Crespo, B.; Escribano, J.; González, R.; Lozano, S.; Huss, S.; Santos-Villarejo, A.; Martin-Plaza, J. J.; Mendoza, A.; Rebollo-Lopez, M. J.; Remuiñan-Blanco, M.; Lavandera, J. L.; Pérez-Herran, E.; Gamo-Benito, F. J.; García-Bustos, J. F.; Barros, D.; Castro, J. P.; Cammack, N. Fueling open-source drug discovery: 177 small-molecule leads against tuberculosis. ChemMed-Chem 2013, 8, 313-321.

Basith, S.; Cui, M.; Macalino, S. J. Y.; Park, J.; Clavio, N. A. B.; Kang, S.; Choi, S. Exploring G-protein-coupled Receptors (GPCRs) ligand space via cheminformatics approaches: impact on rational drug design. Front. Pharmacol. 2018, 9, 128.

Battye, T. G. G.; Kontogiannis, L.; Johnson, O.; Powell, H. R.; Leslie, A. G. W. iMOSFLM: a new graphical interface for diffractionimage processing with MOSFLM. Acta Crystallogr., Sect. D: Biol. Crystallogr. 2011, 67, 271-281.

Besnard, J.; Ruda, G. F.; Setola, V.; Abecassis, K.; Rodriguiz, R. M.; Huang, X.; Norval, S.; Sassano, M. F.; Shin, A. I.; Webster, L. A.; Simeons, F. R. C.; Stojanovski, L.; Prat, A.; Seidah, N. G.; Constam, D. B.; Bickerton, G. R.; Read, K. D.; Wetsel, W. C.; Gilbert, I. H.; Roth, B. L.; Hopkins, A. L. Automated design of ligands to polypharmacological profiles. Nature 2012, 492, 215-220.

(Continued)

*Primary Examiner* — Samantha L Shterengarts
(74) *Attorney, Agent, or Firm* — Quarles & Brady LLP

(57) ABSTRACT

Disclosed are 7-phenyl-2-aminoquinoline compounds that are shown to inhibit the biological activity of neuronal nitric oxide synthases (nNOSs). Also disclosed are pharmaceutical compositions comprising the compounds, and methods of using the compounds and pharmaceutical compositions for treating a subject in need thereof. Because the disclosed compounds are shown to inhibit the activity of neuronal nitric oxide synthases (nNOSs), the disclosed compounds and pharmaceutical compositions may be utilized in methods for treating a subject having or at risk for developing a disease or disorder that is associated with nNOS activity including neurological diseases and disorders.

20 Claims, 5 Drawing Sheets

(56) References Cited

OTHER PUBLICATIONS

Borg, G.; Cogan, D. A.; Ellman, J. A. One-pot asymmetric synthesis of tert-butanesulfinyl-protected amines from ketones by the in situ reduction of tert-butanesulfinyl ketimines. Tetrahedron Lett. 1999, 40, 6709-6712.
Campbell, M. G.; Smith, B. C.; Potter, C. S.; Carragher, B.; Marletta, M. A. Molecular architecture of mammalian nitric oxide synthase. Proc. Natl. Acad. Sci. U.S.A. 2014, 111, E3614-E3623.
Cinelli, M. A.; Li, H.; Chreifi, G.; Martasek, P.; Roman, L. J.; Poulos, T. L.; Silverman, R. B. Simplified 2-aminoquinoline-based scaffold for potent and selective neuronal nitric oxide synthase inhibition. J. Med. Chem. 2014, 57, 1513-1530.
Cinelli, M. A.; Li, H.; Chreifi, G.; Poulos, T. L.; Silverman, R. B. Nitrile in the hole: discovery of a small auxiliary pocket in neuronal nitric oxide synthase leading to the development of potent and selective 2-aminoquinoline inhibitors. J. Med. Chem. 2017, 60, 3958-3978.
Cinelli, M. A.; Li, H.; Pensa, A. V.; Kang, S.; Roman, L. J.; Martasek, P.; Poulos, T. L.; Silverman, R. B. Phenyl ether- and anilinecontaining 2-aminoquinolines as potent and selective inhibitors of neuronal nitric oxide synthase. J. Med. Chem. 2015, 58, 8694-8712.
Cinelli, Maris A., Cory T. Reidl, Huiying Li, Georges Chreifi, Thomas L. Poulos, and Richard B. Silverman. First Contact: 7-Phenyl-2-Aminoquinolines, Potent and Selective Neuronal Nitric Oxide Synthase Inhibitors That Target an Isoform-Specific Aspartate. J. Med. Chem. May 14, 2020;63(9):4528-4554, Epub Apr. 7, 2020.
Daina, A.; Michielin, O.; Zoete, V. SwissADME: a free web tool to evaluate pharmacokinetics, drug-likeness and medicinal chemistry friendliness of small molecules. Sci. Rep. 2017, 7, No. 42717.
Daina, A.; Zoete, V. A Boiled-Egg to predict gastrointestinal absorption and brain penetration of small molecules. ChemMedChem 2016, 11, 1117-1121.
Delker, S. L.; Ji, H.; Li, H.; Jamal, J.; Fang, J.; Xue, F.; Silverman, R. B.; Poulos, T. L. Unexpected binding modes of nitric oxide synthase inhibitors effective in the prevention of cerebral palsy. J. Am. Chem. Soc. 2010, 132, 5437-5442.
Delker, S. L.; Xue, F.; Li, H.; Jamal, J.; Silverman, R. B.; Poulos, T. L. Role of zinc in isoform-selective inhibitor binding to neuronal nitric oxide synthase. Biochemistry 2010, 49, 10803-10810.
Di, L.; Kerns, E. H.; Bezar, I. F.; Petusky, S. L.; Huang, Y. Comparison of blood-brain barrier permeability assays: in situ brain perfusion, MDR1-MDCKII and PAMPA-BBB. J. Pharm. Sci. 2009, 98, 1980-1991.
Di, L.; Kerns, E. H.; Fan, K.; McConnell, O. J.; Carter, G. T. High throughput artificial membrane permeability assay for blood-brain barrier. Eur. J. Med. Chem. 2003, 38, 223-232.
Dialer, L. O.; Selivanova, S. V.; Muller, C. J.; Muller, A.; Stellfeld, T.; Graham, K.; Dinkelborg, L. M.; Kramer, S. D.; Schibli, R.; Reiher, M.; Ametamey, S. M. Studies toward the development of new silicon-containing building blocks for the direct (18)F-labeling of peptides. J. Med. Chem. 2013, 56, 7552-7563.
Do, H. T.; Li, H.; Chreifi, G.; Poulos, T. L.; Silverman, R. B. Optimization of blood-brain barrier permeability with potent and selective human heuronal nitric oxide synthase inhibitors having a 2-aminopyridine scaffold. J. Med. Chem. 2019, 62, 2690-2707.
Do, H. T.; Wang, H.-Y.; Li, H.; Chreifi, G.; Poulos, T. L.; Silverman, R. B. Improvement of Cell Permeability of Human Neuronal Nitric Oxide Synthase Inhibitors Using Potent and Selective 2-Aminopyridine-Based Scaffolds with a Fluorobenzene Linker. J. Med. Chem. 2017, 60, 9360-9375.
Evans, P. Scaling and assessment of data quality. Acta Crystallogr., Sect. D: Biol. Crystallogr. 2006, 62, 72-82.
Fisher, T. H.; Dershem, S. M.; Prewitt, M. L. Meta-substituent effects on benzyl free-radical stability. J. Org. Chem. 1990, 55, 1040-1043.
Fossetta, J. D.; Niu, X. D.; Lunn, C. A.; Zavodny, P. J.; Narula, S. K.; Lundell, D. Expression of human inducible nitric oxide synthase in *Escherichia coli*. FEBS Lett. 1996, 379, 135-138.
Gamboa, A.; Shibao, C.; Diedrich, A.; Choi, L.; Pohar, B.; Jordan, J.; Paranjape, S.; Farley, G.; Biaggioni, I. Contribution of endothelial nitric oxide to blood pressure in humans. Hypertension 2007, 49, 170-177.
Garcin, E. D.; Arvai, A. S.; Rosenfeld, R. J.; Kroeger, M. D.; Crane, B. R.; Andersson, G.; Andrews, G.; Hamley, P. J.; Mallinder, P. R.; Nicholls, D. J.; St-Gallay, S. A.; Tinker, A. C.; Gensmantel, N. P.; Mete, A.; Cheshire, D. R.; Connolly, S.; Stuehr, D. J.; Aberg, A.; Wallace, A. V.; Tainer, J. A.; Getzoff, E. D. Anchored plasticity opens doors for selective inhibitor design in nitric oxide synthase. Nat. Chem. Biol. 2008, 4, 700-707.
Gerber, N. C.; Ortiz de Montellano, P. R. Neuronal nitric oxide synthase: expression in *Escherichia coli*, irreversible inhibition by phenyldiazene, and active site topology. J. Biol. Chem. 1995, 270, 17791-17796.
Günbaş, D. D.; Brouwer, A. M. Degenerate molecular shuttles with flexible and rigid spacers. J. Org. Chem. 2012, 77, 5724-5735.
Halgren, T. A. Merck molecular force field. I. Basis, form, scope, parameterization, and performance of MMFF94. J. Comput. Chem. 1996, 17, 490-519.
Hebeisen, P.; Weiss, U.; Staempfli, A.; Ring opening of cyclic sulfamidates with bromophenyl metal reagents: complementarity of sulfamidates and aziridines. Tetrahedron Lett. 2011, 52, 5229-5233.
Hevel, J. M.; Marletta, M. A. [25] Nitric-oxide synthase assays. Methods Enzymol. 1994, 233, 250-258.
Hevel, J. M.; White, K. A.; Marletta, M. A. Purification of the inducible murine macrophage nitric oxide synthase: identification as a flavoprotein. J. Biol. Chem. 1991, 266, 22789-22791.
Huang, H.; Li, H.; Martasek, P.; Roman, L. J.; Poulos, T. J.; Silverman, R. B. Structure-guided design of selective inhibitors of neuronal nitric oxide synthase. J. Med. Chem. 2013, 56, 3024-3032.
Jarboe, S. G.; Terrazas; Beak, P. The endocyclic restriction test: the geometries of nucleophilic substitutions at sulfur (VI) and sulfur (II). J. Org. Chem. 2008, 73, 9627-9632.
Kabsch, W. XDS. Acta Crystallogr., Sect. D: Biol. Crystallogr. 2010, 66, 125-132.
Könczöl, Á.; Müller, J.; Földes, E.; Béni, Z.; Végh, K.; Kéry, Á.; Balogh, G. T. Applicability of a blood-brain barrier specific artificial membrane permeability assay at the early stage of natural productbased CNS drug discovery. J. Nat. Prod. 2013, 76, 655-663.
Labby, K. J.; Xue, F.; Kraus, J. M.; Ji, H.; Mataka, J.; Li, H.; Martásek, P.; Roman, L. J.; Poulos, T. L.; Silverman, R. B. Intramolecular hydrogen bonding: A potential strategy for more bioavailable inhibitors of neuronal nitric oxide synthase. Bioorg. Med. Chem. 2012, 20, 2435-2443.
Labute P. The generalized Born/volume integral implicit solvent model: Estimation of the free energy of hydration using London dispersion instead of atomic surface area. J. Comput. Chem. 2008, 29, 1693-1698.
Lalwani, K. G.; and Sudalai, A. A concise enantioselective synthesis of (+)-L-733,060 and (+)-T-2328 via sequential proline catalysis. Synlett 2016, 27, 1339-1343.
Leber, A.; Hemmens, B.; Klosch, B.; Goessler, W.; Raber, G.; Mayer, B.; Schmidt, K. Characterization of recombinant human endothelial nitric-oxide synthase purified from the yeast *Pichia pastoris*. J. Biol. Chem. 1999, 274, 37658-37665.
Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. Acta Crystallogr., Sect. D: Biol. Crystallogr. 2014, 70, 2667-2674.
Li, H.; Wang, H. Y.; Kang, S.; Silverman, R. B.; Poulos, T. L. Electrostatic control of isoform selective inhibitor binding in nitric oxide synthase. Biochemistry 2016, 55, 3702-3707.
Liebschner, D.; Afonine, P. V.; Moriarty, N. W.; Poon, B. K.; Sobolev, O. V.; Terwilliger, T. C.; Adams, P. D. Polder maps: improving OMIT maps by excluding bulk solvent. Acta Crystallogr., Sect. D: Biol. Crystallogr.. 2017, 73, 148-157.
McCoy, A. J.; Grosse-Kunstleve, R. W.; Adams, P. D.; Winn, M. D.; Storoni, L. C.; Read, R. J. Phaser crystallographic software. J. Appl. Crystallogr. 2007, 40, 658-674.
McPhillips, T. M.; McPhillips, S. E.; Chiu, H.-J.; Cohen, A. E.; Deacon, A. M.; Ellis, P. J.; Garman, E.; Gonzalez, A.; Sauter, N. K.; Phizackerley, R. P.; Soltis, S. M.; Kuhn, P. Blu-Ice and the Distrib-

(56) References Cited

OTHER PUBLICATIONS uted Control System: software for data acquisition and instrument control at macromolecular crystallography beamlines. J. Synchrotron Radiat. 2002, 9, 401-406.
Molander, G. A.; Trice, S. L. J.; Kennedy, S. M. Scope of the two-step, one-pot palladium-catalyzed borylation/suzuki cross-coupling reaction utilizing bis-boronic acid. J. Org. Chem. 2012, 77, 8678-8688.
Molecular Operating Environment (MOE), Aug. 2013; Chemical Computing Group ULC, 1010 Sherbrooke St. West, Suite #910, Montreal, QC, Canada, H3A 2R7, 2018.
Mugumbate, G.; Abrahams, K. A.; Cox, J. A. G.; Papadatos, G.; van Westen, G.; Lelièvre, J.; Calus, S. T.; Loman, N. J.; Ballell, L.; Barros, D.; Overington, J. P.; Besra, G. S. Mycobacterial dihydrofolate reductase inhibitors identified using chemogenomic methods and in vitro validation. PLoS One 2015, 10, No. e0121492.
Mukherjee et al., Chem. Soc. Rev., Oct. 7, 2014; 43(19):6814-6838.
Mukherjee, P.; Li, H.; Sevrioukova, I.; Chreifi, G.; Martásek, P.; Roman, L. J.; Poulos, T. L.; Silverman, R. B. Novel 2,4-disubstituted pyrimidines as potent, selective, and cell-permeable inhibitors of neuronal nitric oxide Synthase. J. Med. Chem. 2015, 58, 1067-1088.
International Search Report and Written Report, corresponding to PCT/US2020/057417, dated Jan. 13, 2021.
Müller, J.; Essö, K.; Dargo', G.; Könczöl, A'.; Balogh, G. T. Tuning the predictive capacity of the PAMPA-BBB model. Eur. J. Pharm. Sci. 2015, 79, 53-60.
Murshudov, G. N.; Vagin, A. A.; Dodson, E. J. Refinement of macromolecular structures by the maximum-likelihood method. Acta Crystallogr., Sect. D: Biol. Crystallogr. 1997, 53, 240-255.
Emsley, P.; Cowtan, K. Coot: model-building tools for molecular graphics. Acta Crystallogr., Sect. D: Biol. Crystallogr. 2004, 60, 2126-2132.
Nielsen, S. F.; Larsen, M.; Boesen, T.; Schonning, K.; Kromann, H. Cationic chalcone antibiotics. Design, synthesis, and mechanism of action. J. Med. Chem. 2005, 48, 2667-2677.
Pensa, A. V.; Cinelli, M. A.; Li, H.; Chreifi, G.; Mukherjee, P.; Roman, L. J.; Martasek, P.; Poulos, T. L.; Silverman, R. B. Hydrophilic, potent, and selective 7-substituted 2-aminoquinolines as improved human neuronal nitric oxide synthase inhibitors. J. Med. Chem. 2017, 60, 7146-7165.
Poulos, T. L.; Li, H. Structural basis for isoform-selective inhibition in nitric oxide synthase. Acc. Chem. Res. 2013, 46, 390-398.
Rankovic, Z. CNS drug design: balancing physicochemical properties for optimal brain exposure. J. Med. Chem. 2015, 58, 2584-2608.
Roman, L. J.; Sheta, E. A.; Martásek, P.; Gross, S. S.; Liu, Q.; Masters, B. S. S. High-level expression of functional rat neuronal nitric oxide synthase in *Escherichia coli*. Proc. Natl. Acad. Sci. U.S.A. 1995, 92, 8428-8432.
The PyMOL Molecular Graphics System; version 1.8, Schrodinger, LLC.: 2015.
Torreilles, F.; Salman-Tabcheh, S.; Guérin, M.; Torreilles, J. Neurodegenerative disorders: the role of peroxynitrite. Brain Res. Rev. 1999, 30, 153-163.
Trippier, P. C.; Jansen Labby, K.; Hawker, D. D.; Mataka, J. J.; Silverman, R. B. Target- and mechanism-based therapeutics for neurodegenerative diseases: strength in numbers. J. Med. Chem. 2013, 56, 3121-3147.
Uehara, T.; Nakamura, T.; Yao, D.; Shi, Z.; Gu, Z.; Ma, Y.; Masliah, E.; Nomura, Y.; Lipton, S. A. S-Nitrosylated proteindisulphide isomerase links protein misfolding to neurodegeneration. Nature 2006, 441, 513-517.
Wang, J.; Wolf, R. M.; Caldwell, J. W.; Kollman, P. A.; Case, D. A. Development and testing of a general amber force field. J. Comput. Chem. 2004, 25, 1157-1174.
Winn, M. D.; Isupov, M. N.; Murshudov, G. N. Use of TLS parameters to model anisotropic displacements in macromolecular refinement. Acta Crystallogr., Sect. D: Biol. Crystallogr.. 2001, 57, 122-133.
Xue, F.; Li, H.; Fang, J.; Roman, L. J.; Martásek, P.; Poulos, T. L.; Silverman, R. B. Peripheral but crucial: A hydrophobic pocket (Tyr706, Leu337, and Met336) for potent and selective inhibition of neuronal nitric oxide synthase. Bioorg. Med. Chem. Lett. 2010, 20, 6258-6261.
Yanagisawa, I.; Hirata, Y.; Ishii, Y. Studies on histamine H2 receptor antagonists. 2. Synthesis and pharmacological activities of Nsulfamoyl and N-sulfonyl amidine derivatives. J. Med. Chem. 1987, 30, 1787-1793.
C, Yung-Chi; Prusoff, W. H. Relationship between the inhibition constant (Ki) and the concentration of the inhibitor which causes 50 per cent inhibition (IC50) of an enzymatic reaction. Biochem. Pharmacol. 1973, 22, 3099-3108.

* cited by examiner

1

2

3

4

5

6

7

8

9

10

11

12

13

5-Substitution
14
15
12
4-Substitution
R = F, 19
R = Cl, 20
R = $CF_3$, 21
R = Et, 22
R = OMe, 23
R = OEt, 24
R = O-*n*-Pr, 25
R = O-*i*-Pr, 26
R = O-*i*-Bu, 27
R = 28
R = 29
R = 30
R = 31
R = 32
R = 33
R = 34
R = 35
R = 36
R = 37
Amine Constraint
16
17
18

(b)

SELECTIVE NEURONAL NITRIC OXIDE SYNTHASE INHIBITORS

CROSS-REFERENCE TO RELATED APPLICATIONS

The present application represents the national sage entry of PCT/US2020/057417 filed on Oct. 26, 2020, which claims the benefit of priority under 35 U.S.C. § 119(e) to U.S. Provisional Application No. 62/926,178, filed on Oct. 25, 2019, the contents of each are incorporated herein by reference in their entireties.

CROSS-REFERENCE TO RELATED PATENT APPLICATIONS

The present application represents the national sage entry of PCT/US2020/057417 filed on Oct. 26, 2020, which claims the benefit of priority under 35 U.S.C. § 119(e) to U.S. Provisional Application No. 62/926,178, filed on Oct. 25, 2019, the contents of each are incorporated herein by reference in their entireties.

STATEMENT REGARDING FEDERALLY SPONSORED RESEARCH OR DEVELOPMENT

This invention was made with government support under GM049725 and GM131788 awarded by the National Institutes of Health. The government has certain rights in the invention.

BACKGROUND

The field of the invention relates to compounds that inhibit the biological activity of nitric oxide synthases (NOSs). In particular, the field of the invention relates to compounds that selectively inhibit nitric oxide synthases such as human neuronal NOS (nNOS).

NO is a highly reactive free radical produced by the hemethiolate monooxygenase nitric oxide synthase (NOS, mNOS=mammalian NOS). NOS generates NO by oxidizing L-Arg and is found in mammals. mNOS is a multi-domain protein composed of both oxygenase and reductase domains. X-ray crystal structures determined mNOS oxygenase domains reveals a near identical tertiary structure and active site. N-terminal fragment that contains the $Zn^{2+}$ binding motif is observed in mNOS.

In mammalian systems, NO functions as an essential signaling molecule and is involved in a variety of physiological functions ranging from blood pressure homeostasis to neural cell communication and host defense. There are three mNOS isoforms: endothelial NOS (eNOS), inducible NOS (iNOS) and neuronal NOS (nNOS). Owing to the pathological consequences of the over or under production of NO, significant effort has been made toward the development and characterization of isoform selective mNOS inhibitors, which has resulted in the development of many unique inhibitors.

Neuronal nitric oxide synthase (nNOS) catalyzes the oxidation of L-arginine to L-citrulline in the central nervous system, generating nitric oxide (NO), a critical neurotransmitter. Significant research has implicated the overexpression of nNOS and overproduction of NO in various neurological diseases, including Parkinson's, Alzheimer's, and Huntington's diseases, as well as neuronal damage due to stroke, cerebral palsy and migraine headaches. Inhibiting endothelial nitric oxide synthase (eNOS) and inducible nitric oxide synthase (iNOS) is, however, undesirable, because these isozymes are responsible for maintaining crucial body function. Thus, selective inhibition of nNOS over its closely related isoforms, eNOS and iNOS, can provide a promising strategy in developing therapeutics for the treatment of neurodegenerative diseases.

Many organic scaffolds have been investigated over the past decade. However, most inhibitor compounds investigated to datye are mimics of the natural substrate of nNOS, the amino acid L-argine. Such compound are basic and highly charge under physiological conditions, adversely affecting blood-brain barrier (BBB) permeation. In addition, useful nNOS inhibitors should exhibit selectivity for nNOS over the iNOS and eNOS to avoid unintended negative side effects. Yet some compounds, while promising, are limited by synthetic challenge and/or low yield. As a result, there remains an on-going concern in the art to provide an efficient approach toward a facile synthesis of a wide range of such nNOS inhibitors, with structures optimized for enhanced pharmacological effect

SUMMARY

Disclosed are compounds, pharmaceutical compositions comprising the compounds, and methods of using the compounds and pharmaceutical compositions for treating a subject in need thereof. The disclosed compounds inhibit the activity of nitric oxide synthases (NOSs) and may selectively inhibit nitric oxide synthase (nNOS). As such, the disclosed compounds and pharmaceutical compositions may be utilized in methods for treating a subject having or at risk for developing a disease or disorder that is associated with nNOS activity including neurodegenerative diseases and disorders.

The disclosed compounds, compositions and related methods of use for the selective inhibition of neuronal nitric oxide synthase, overcome various deficiencies and shortcomings of the prior art including those outlined above. The disclosed compounds preferably exhibit selective nNOS inhibition over other enzyme isoforms and preferably provide improved membrane permeability and bioavailability. The disclosed compounds can be utilized in vivo, for example in methods of treating and/or preventing diseases or disorders associated with nNOS activity, and/or in vitro for example in order to study conditions promoting nitric oxide production, indicative of one or more mammalian disease states.

The disclosed compounds may be described as having a formula:

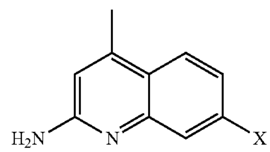

wherein:

X is selected from alkyl-amino substituted phenyl, alkyl-amino substituted pyridyl (e.g., alkyl-amino substituted pyridyl pyrid-2-yl, pyrid-3-yl, or pyrid-4-yl), isoindolinyl (e.g., isoindolin-3yl or isoindolin-4yl), and amino-substituted indanyl (e.g., amino-substituted indan-5-yl or indan-6-yl); and optionally X is substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy, and substituents having a formula —O—$CH_2$—Y, wherein Y is cycloalkyl (e.g., cyclopropyl or cyclobutyl), aryl, or heteroaryl wherein Y is optionally substituted with a substituent selected from alkyl (e.g., methyl), halo (e.g., fluoro), and cyano.

The disclosed compounds may be utilized to prepare pharmaceutical compositions for treating and/or preventing diseases and disorders associated with nNOS activity, including neurological diseasese and disorders (e.g., neurodegenerative diseases and disorders) such as Alzheimer's disease, Huntington's disease, Parkinson's disease, and amyotrophic lateral sclerosis (ALS). As such, methods of treatment also are contemplated herein. In the methods of treatment and/or prevention, the disclosed compounds or pharmaceutical compositions comprising the disclosed compounds may be administered to a subject in need thereof, such as a subject having or at risk for developing a disease or disorder associated with nNOS activity. In the treatment and/or prevention methods, the subject may be administered an effective amount of the disclosed compounds for inhibiting the biological activity of nNOS, thereby treating and/or preventing the disease or disorder associated with biological activity of nNOS in the subject.

DETAILED DESCRIPTION

Figure 1:
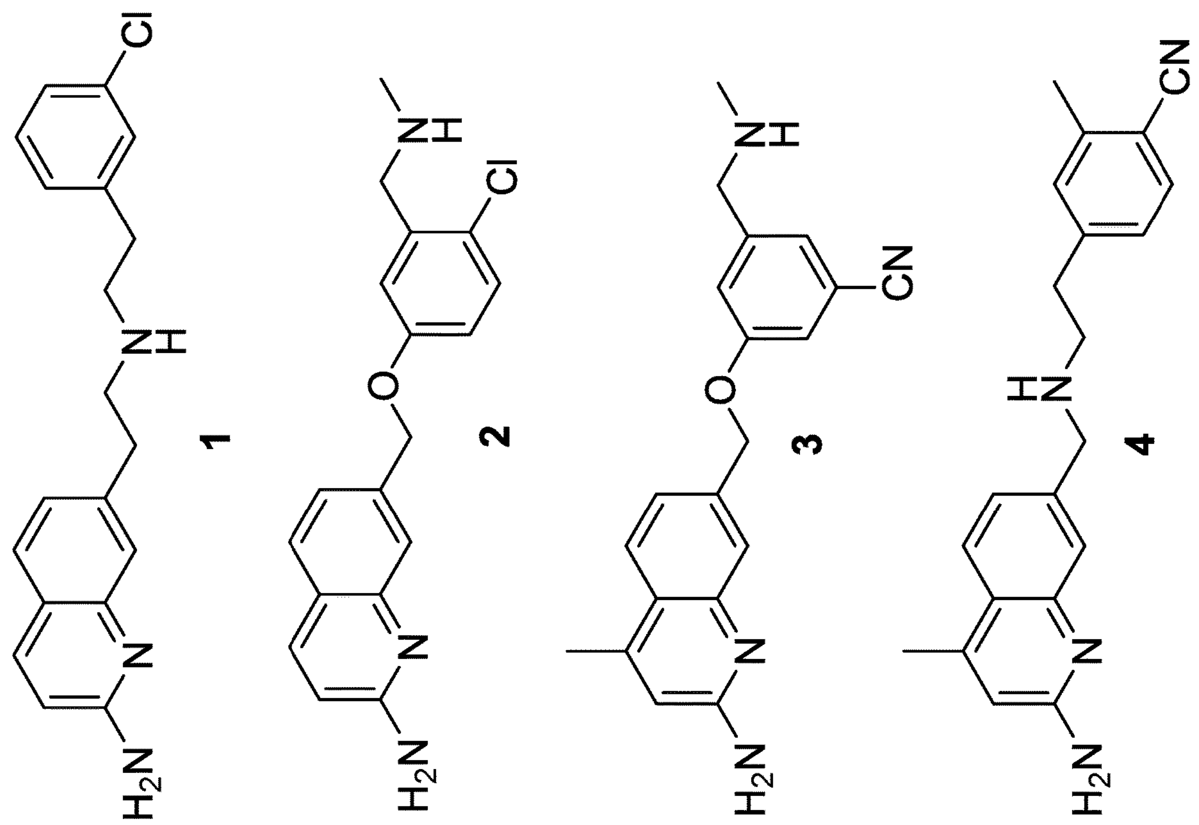
FIG. 1. Representative aminoquinoline nNOS inhibitors.

The disclosed subject matter further may be described utilizing terms as defined below.

Unless otherwise specified or indicated by context, the terms "a", "an", and "the" mean "one or more." For example, "a modulator of nitric oxide synthase activity" should be interpreted to mean "one or more modulators of nitric oxide synthase activity."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, a "subject in need thereof" may include a subject having or at risk for developing a disease or disorder associated with nitric oxide synthase (NOS) activity, including a disease or disorder associated with neuronal nitric oxide synthase (nNOS) activity. A subject in need thereof may include, but is not limited to, a subject having or at risk for developing a neurological disease or disorder, which may include, but is not limited to a neurodegenerative disease or disorder. A subject in need thereof may include, but is not limited to, a subject having or at risk for developing Parkinson's disease, Alzheimer's disease, and Huntington's disease, as well as neuronal damage due to stroke, cerebral palsy and migraine headaches. A "subject in need thereof" may include a human or non-human subject (e.g., a non-human mammal).

Chemical Entities

In some aspects, the disclosed matter relates to new chemical entities.

The term "alkyl" as used herein refers to a saturated straight or branched hydrocarbon, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen (e.g., —F, —Cl, —Br, or —I). For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The term "heterary" refers to a heterocyclic aromatic group. Representative heteroaryl groups may include pyridyl, thiozolyl, oxazolyl, and isoxazolyl.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of—O-alkyl, —O-alkenyl, —O-alkynyl, and the like.

The term "carbonyl" as used herein refers to the radical-C(O)—.

The term "carboxamido" as used herein refers to the radical-C(O) NRR', where R and R' may be the same or different. Rand R' may be independently alkyl, aryl, arylalkyl, cycloalkyl, formyl, haloalkyl, heteroaryl, or heterocyclyl.

The term "carboxy" as used herein refers to the radical-COOH or its corresponding salts, e.g. —COONa, etc.

The term "amide" or "amido" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Treatment Methods and Pharmaceutical Compositions

The terms "subject," "patient," and "individual" may be used interchangeably herein. A subject may be a human subject. A subject may refer to a human subject having or at risk for acquiring a disease or disorder that is associated with nitric oxide synthase (NOS) activity, which may include a disease or disorder that is associated with aberrant nitric oxide synthase activity. As used herein, the term "aberrant" means higher or lower activity relative to a normal healthy subject. A subject having a disease or disorder associated with nitric oxide synthase activity may include a subject having a disease or disorder associated with neuronal NOS (nNOS), inducible NOS (iNOS), and/or endothelial NOS (eNOS). In specific embodiments, a subject having a disease or disorder associated with nitric oxide synthase activity may include a subject having or at risk for developing a neuronal disease or disorder (e.g., migraine, depression, stroke) and/or a neurodegenerative disease (e.g., Alzheimer's, Parkinson's, and/or Huntington's disease). (See, e.g., Mukherjee et al., Chem. Soc. Rev., 2014 Oct. 7; 43 (19): 6814-6838, the content of which is incorporated herein by reference in its entirety. Inhibitors of NOS that are under clinical development include cindunistat, A-84643, ONO-1714, L-NOARG, NCX-456, VAS-2381, GW-273629, NXN-462, CKD-712, KD-7040, and guanidinoethyldisulfide.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating and/or preventing the conditions/diseases described herein, even though such dosage is deemed to be a therapeutically effective amount by those of skill in the art.

As used herein, the term "modulate" means decreasing or inhibiting activity and/or increasing or augmenting activity. For example, modulating glucocerebrosidase activity means decreasing or inhibiting glucocerebrosidase activity and/or increasing or augmenting glucocerebrosidase activity. The compounds disclosed herein may be administered to modulate glucocerebrosidase activity for example, as a chaperone or activator.

In part, the present invention can be directed to a method inhibiting, modulating or otherwise affecting a nitric oxide synthase. Such a method can comprise providing a compound of this invention, e.g., without limitation, one or more of the preceding compounds whether or not part of a pharmaceutical composition, and administering an effective amount of such a compound for contact with a nitric oxide synthase, such compounds as can include but are not limited to those illustrated by the following examples, referenced figures and/or accompanying synthetic schemes. Structural analogs of such compounds can be prepared using techniques of the sort described herein or in the references incorporated herein, or straight-forward variations thereof. Such analogous compounds are limited only by commercial or synthetic availability of corresponding starting materials and reagents, such techniques, variations, starting materials and reagents as would be understood by those skilled in the art made aware of this invention. In certain such embodiments, such a compound and/or combination thereof can be present in an amount at least partially sufficient to increase human (and rat) nNOS binding affinity and selectively inhibit human/rat neuronal nitric oxide synthase over inducible and endothelial isoforms. Such a method can thereby inhibit, modulate or otherwise affect production of nitric oxide. Such a method can comprise providing a compound of this invention, whether or not part of a pharmaceutical composition, and administering an effective amount of such a compound for contact with a nitric oxide synthase, such compounds including but not limited to those illustrated by the following examples, referenced figures and/or accompanying synthetic schemes. In certain such embodiments, such a compound and/or combination thereof can be present in an amount at least partially sufficient to selectively inhibit neuronal nitric oxide synthase over inducible and endothelial isoforms.

Further, it will be understood by those skilled in the art that any one or more the compounds of this invention can be provided as part of a pharmaceutical composition comprising a pharmaceutically-acceptable carrier component for use in conjunction with a treatment method or medicament.

Compositions suitable for administration can comprise physiologically acceptable sterile aqueous or nonaqueous solutions, dispersions, suspensions or emulsions. The resulting compositions can be, in conjunction with the various methods described herein, for administration or contact with a nitric oxide synthase. Whether or not in conjunction with a pharmaceutical composition, "contacting" means that a nitric oxide synthase and one or more inhibitor compounds are brought together for purpose of binding and/or complexing such an inhibitor compound to the enzyme (e.g. nNOS). Amounts of a compound effective to inhibit a nitric oxide synthase may be determined empirically, and making such determinations is within the skill in the art. Inhibition or otherwise affecting nitric oxide synthase activity includes modulation, reduction and/or mitigation, as well as elimination of NOS activity and/or nitric oxide production.

Itis understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, PA.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more neuronal nitric oxide synthase inhibitor compounds for the manufacture of a medicament for therapeutic use in the treatment or prevention of a disease state indicated by nitric oxide production.

Novel 7-Phenyl-2-Aminoquinolines For Use as Potent and Selective Neuronal Nitric Oxide Synthase Inhibitors Disclosed are compounds, pharmaceutical compositions comprising the compounds, and methods of using the compounds and pharmaceutical compositions for treating a subject in need thereof. The disclosed compounds inhibit the activity of nitric oxide synthases (NOSs) and may selectively inhibit nitric oxide synthase (nNOS). As such, the disclosed compounds and pharmaceutical compositions may be utilized in methods for treating a subject having or at risk for developing a disease or disorder that is associated with nNOS activity including neurodegenerative diseases and disorders.

In some embodiments, the disclosed compounds may have a formula described as

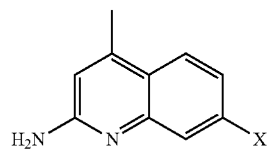

or a salt or solvate thereof, where X is selected from alkyl-amino substituted phenyl, alkyl-amino substituted pyridyl (e.g., alkyl-amino substituted pyridyl pyrid-2-yl, pyrid-3-yl, or pyrid-4-yl), isoindolinyl (e.g., isoindolin-3-yl or isoindolin-4yl), and amino-substituted indanyl (e.g., amino-substituted indan-5-yl or indan-6-yl); and optionally X is substituted or further substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy, and substituents having a formula —$OCH_2$—Y, wherein Y is cycloalkyl, aryl, or heteroaryl and wherein Y is optionally substituted with a substituent selected from alkyl (e.g., methyl), halo (e.g., fluoro), and cyano.

In some embodiments of the disclosed compounds, X is alkyl-amino substituted phenyl, and optionally X is substituted or further substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy, and substituents having a formula —O—$CH_2$—Y, wherein Y is cycloalkyl (e.g., cyclopropyl or cyclobutyl), aryl, or heteroaryl wherein Y is optionally substituted with a substituent selected from alkyl (e.g., methyl), halo (e.g., fluoro), and cyano.

More specifically, in some embodiments the disclosed compounds may have a formula:

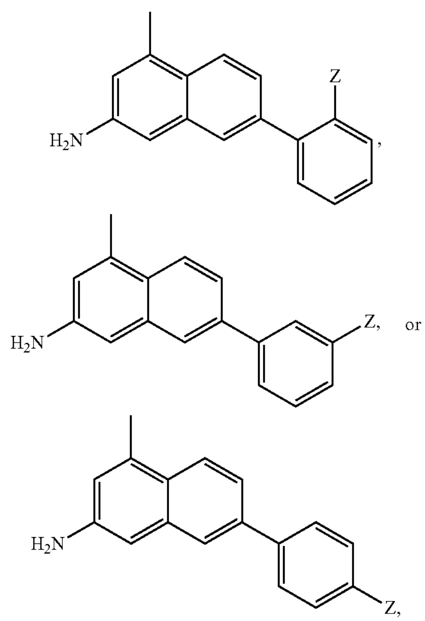

or wherein:

Z is alkyl-amino (e.g., —$CH_2NH_2$, —$CH_2CH_2NH_2$, —$CH_2NHCH_3$, —$CH_2CH_2NHCH_3$, or —$CH_2CH(NH_2)CH_3$).

More specifically, in some embodiments the disclosed compounds may have a formula:

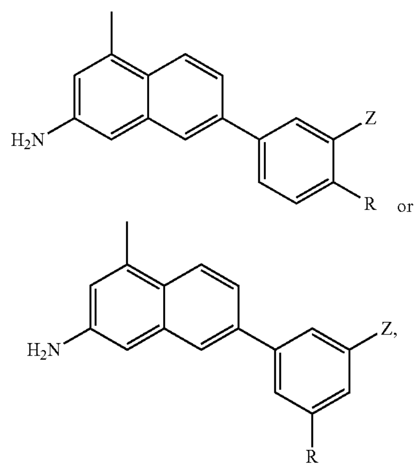

or where R is selected from hydrogen, cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy, and substituents having a formula —$OCH_2$—Y, wherein Y is cycloalkyl (e.g., cyclopropyl or cyclobutyl), aryl, or heteroaryl and wherein Y is optionally substituted with a substituent selected from alkyl (e.g., methyl), halo (e.g., fluoro), and cyano.

Exemplary compounds disclosed herein include, but are not limited to compounds of a formula:

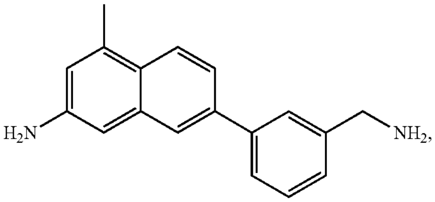

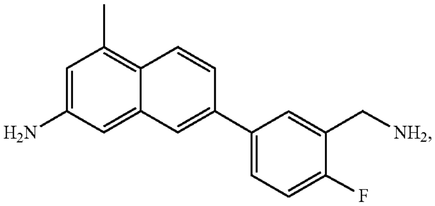

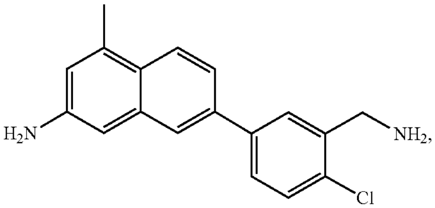

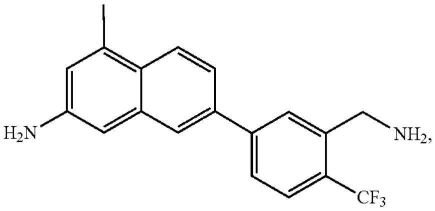

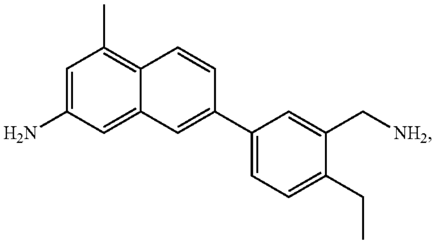

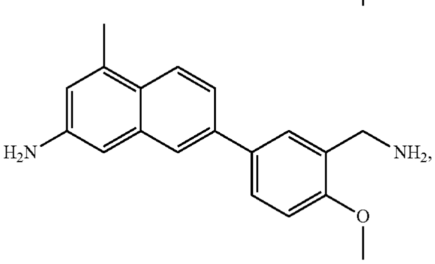

-continued
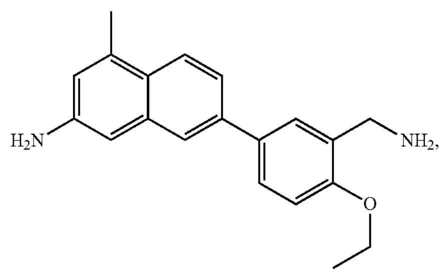
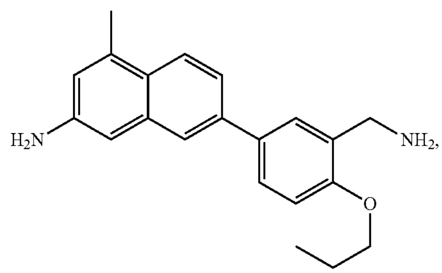
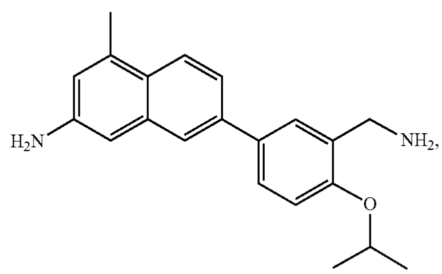
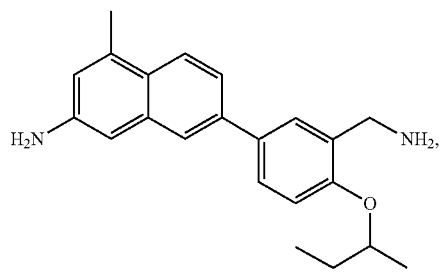
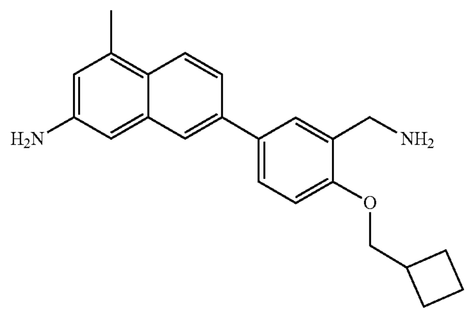
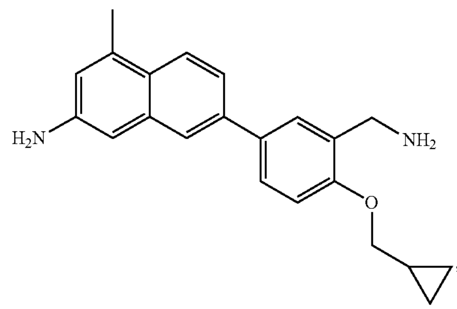
-continued
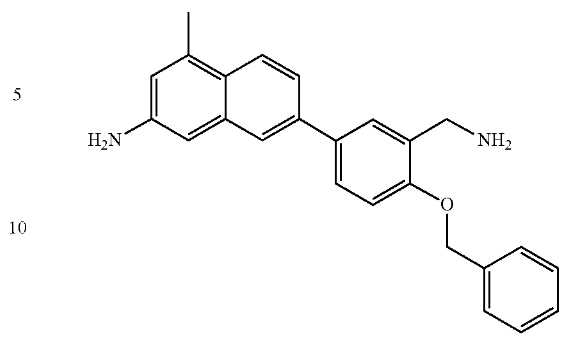
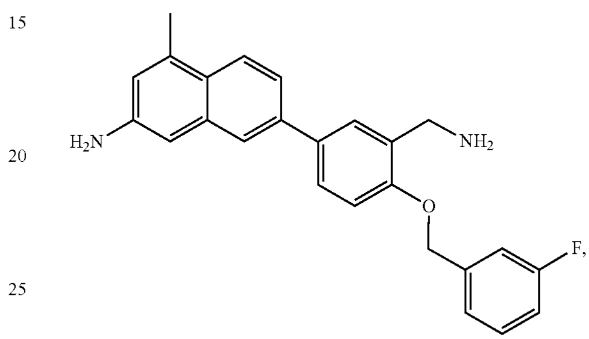
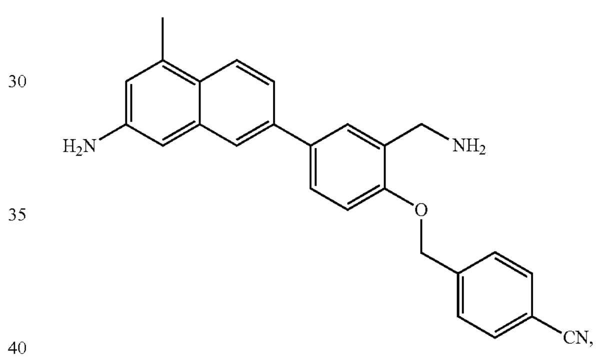
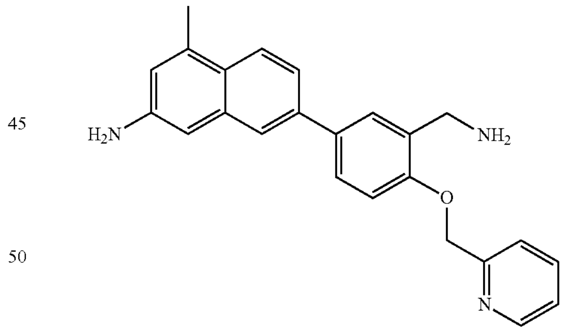
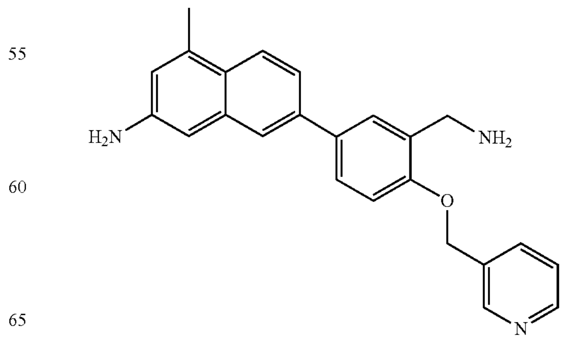

-continued

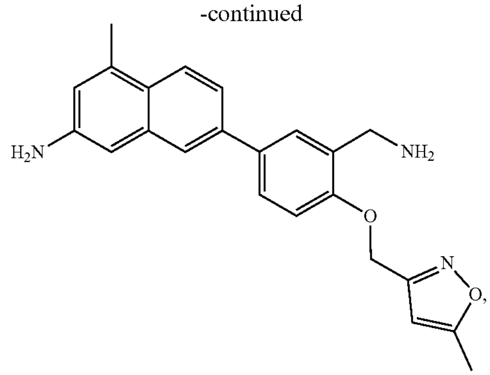

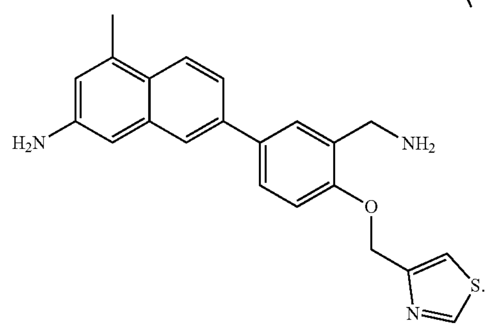

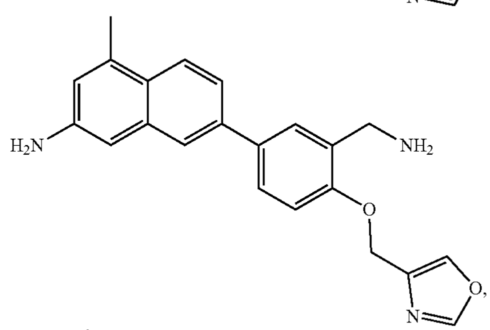

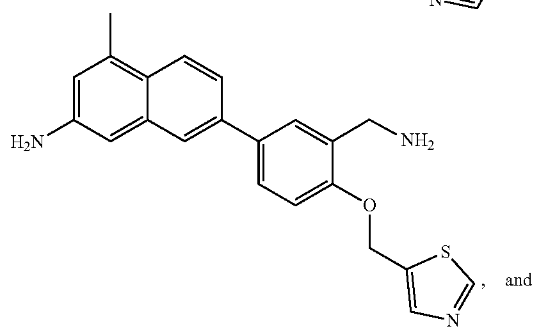

and

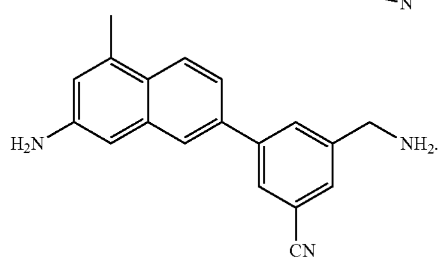

In some embodiments of the disclosed compounds, X is alkyl-amino substituted pyridyl (e.g., alkyl-amino substituted pyridyl pyrid-2-yl, pyrid-3-yl, or pyrid-4-yl), isoindolinyl (e.g., isoindolin-3-yl or isoindolin-4yl), and amino-substituted indanyl (e.g., amino-substituted indan-5-yl or indan-6-yl); and optionally X is substituted or further substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy, and substituents having a formula $-OCH_2-Y$, wherein Y is cycloalkyl (e.g., cyclopropyl or cyclobutyl), aryl, or heteroaryl and wherein Y is optionally substituted with a substituent selected from alkyl (e.g., methyl), halo (e.g., fluoro), and cyano. Such compounds may include compounds of a formula:

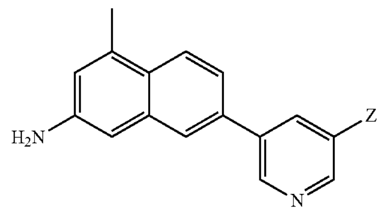

or more specifically compounds of a formula:

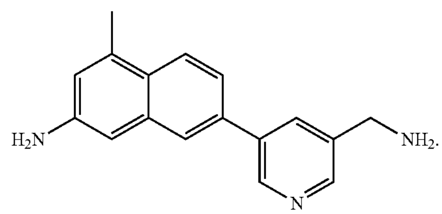 [SMILES: Cc1cc(N)cc2cc(-c3cncc(CN)c3)ccc12]

In some embodiments of the disclosed compounds, X is isoindolinyl (e.g., isoindolin-3-yl or isoindolin-4yl). Such compounds may include a compound of a formula:

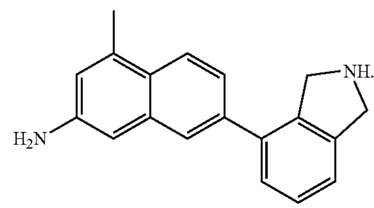 [SMILES: Cc1cc(N)cc2cc(-c3cccc4c3CNC4)ccc12]

In some embodiments of the disclosed compounds, X is amino-substituted indanyl (e.g., amino-substituted indan-5-yl or indan-6-yl). Such compounds may include a compound of a formula:

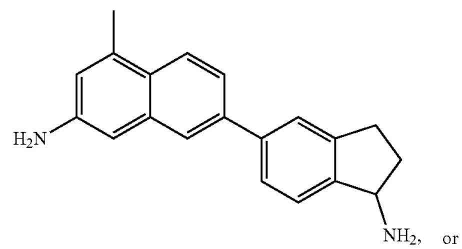

or

-continued

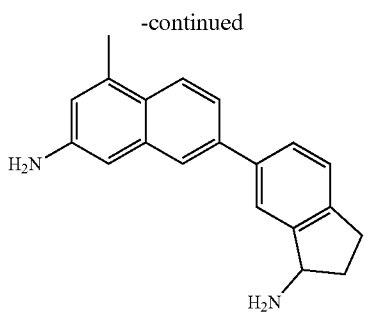

Also disclosed herein are pharmaceutical compositions comprising any of the compounds disclosed herein and a pharmaceutically acceptable carrier, diluent, or excipient. The disclosed pharmaceutical compositions may comprise an effective amount of the compounds to inhibit the biological activity of nitric oxide synthase (NOS) when the pharmaceutical compositions are administered to a subject in need thereof. Preferably, the disclosed pharmaceutical compositions comprise an effective amount of the compounds to selectively inhibit the biological activity of neuronal nitric oxide synthase (nNOS) when the pharmaceutical compositions are administered to a subject in need thereof.

Also disclosed herein are methods of treating and/or preventing a disease or disorder associated with nitric oxide synthase (e.g., neuronal nitric oxide synthase (nNOS)) in a subject in need thereof, the method comprising administering to the subject an effective amount any of the compounds disclosed herein and/or administering a pharmaceutical composition comprising an effective amount of any of the compound disclosed herein. Diseases and disorders treated by the disclosed methods may include but are not limited to neurodegenerative diseases or disorders (e.g., Alzheimer's disease, Huntington's disease, Parkinson's disease, and amyotrophic lateral scleroris (ALS))

The methods disclosed herein also include methods of inhibiting nitric oxide synthase (NOS) in a cell, the method comprising contacting the cell with any of the compounds disclosed herein. Specifically contemplated are methods of inhibiting neuronal nitric oxide synthase (nNOS) in a cell.

Illustrative Embodiments

The following Embodiments are illustrative and should not be interpreted to limit the scope of the claimed subject matter.

Embodiment 1. A compound of a formula:

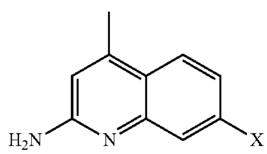

or a salt or solvate thereof, wherein:

X is selected from alkyl-amino substituted phenyl, alkyl-amino substituted pyridyl (e.g., alkyl-amino substituted pyridyl pyrid-2-yl, pyrid-3-yl, or pyrid-4-yl), isoindolinyl (e.g., isoindolin-3-yl or isoindolin-4yl), and amino-substituted indanyl (e.g., amino-substituted indan-5-yl or indan-6-yl); and optionally X is substituted or further substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy), and substituents having a formula —$OCH_2$—Y, wherein Y is cycloalkyl, aryl, or heteroaryl and wherein Y is optionally substituted with a substituent selected from alkyl (e.g., methyl), halo (e.g., fluoro), and cyano.

Embodiment 2. The compound of embodiment 1, wherein X is alkyl-amino substituted phenyl, and optionally X is substituted or further substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy), and substituents having a formula-O—$CH_2$—Y, wherein Y is cycloalkyl, aryl, or heteroaryl wherein Y is optionally substituted with a substituent selected from alkyl (e.g., methyl), halo (e.g., fluoro), and cyano.

Embodiment 3. The compound of embodiment 1 or 2 of a formula:

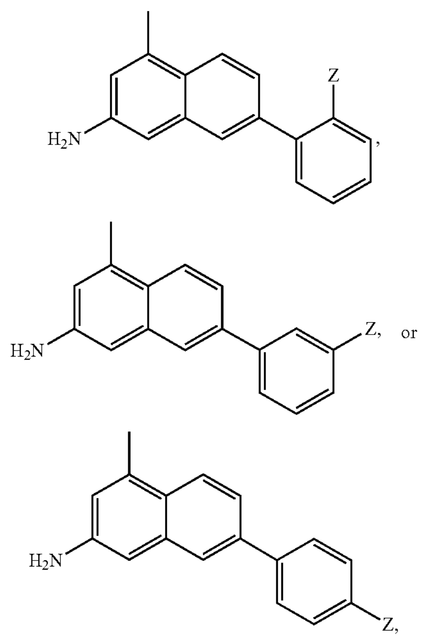

wherein:

Z is alkyl-amino (e.g., —$CH_2NH_2$, —$CH_2CH_2NH_2$, —$CH_2NHCH_3$, —$CH_2CH_2NHCH_3$, or —$CH_2CH(NH_2)CH_3$).

Embodiment 4. The compound of any of the foregoing embodiments of a formula:

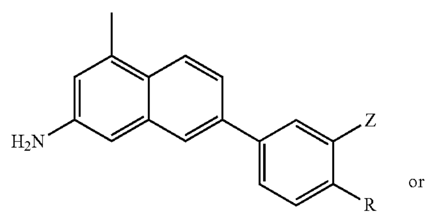

or

-continued

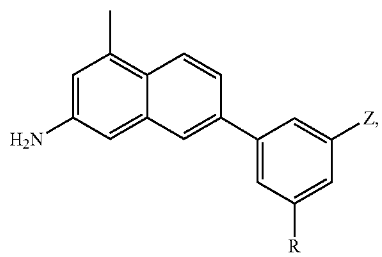

wherein:

R is selected from hydrogen, cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy), and substituents having a formula $-OCH_2-Y$, wherein Y is cycloalkyl, aryl, or heteroaryl and wherein Y is optionally substituted with a substituent selected from alkyl (e.g., methyl), halo (e.g., fluoro), and cyano.

Embodiment 5. The compound of embodiment 4, wherein Z is $-CH_2NH_2$ (i.e., methylamino).

Embodiment 6. The compound of any of the foregoing embodiments of a formula:

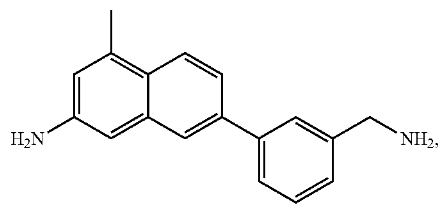

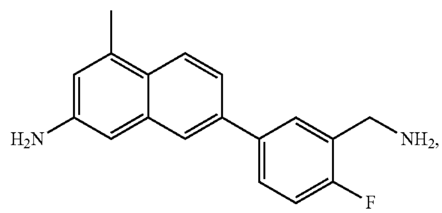

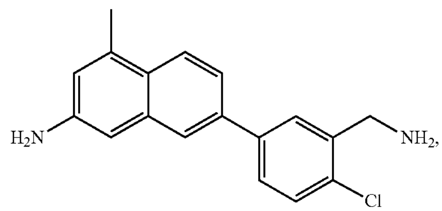

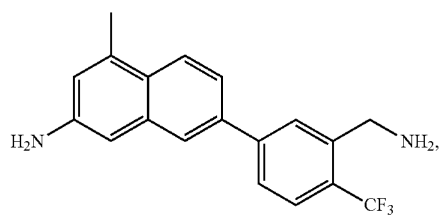

-continued

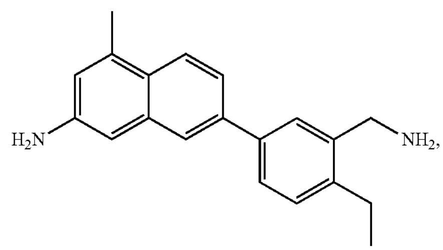

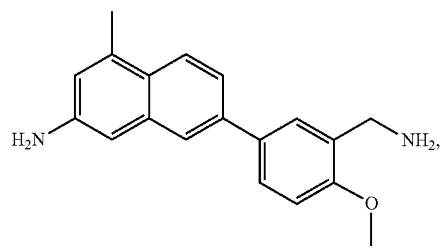

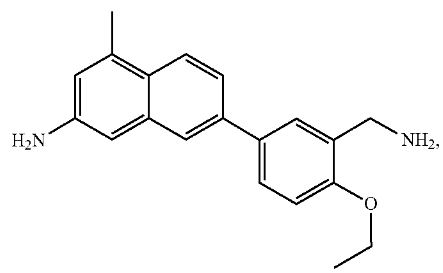

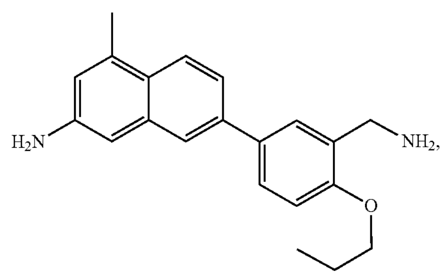

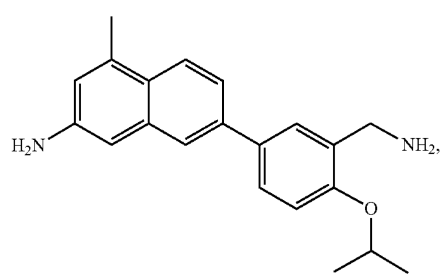

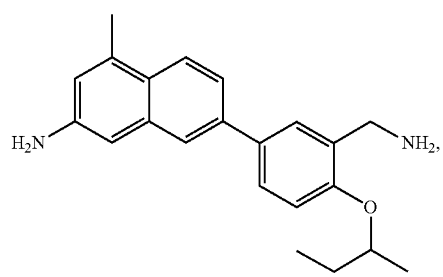

-continued
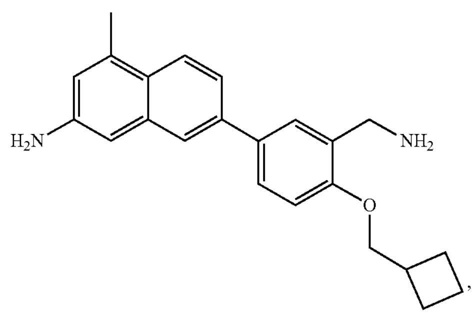
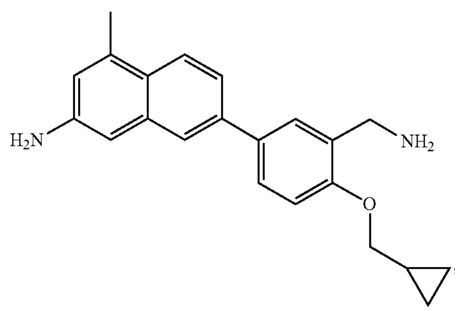
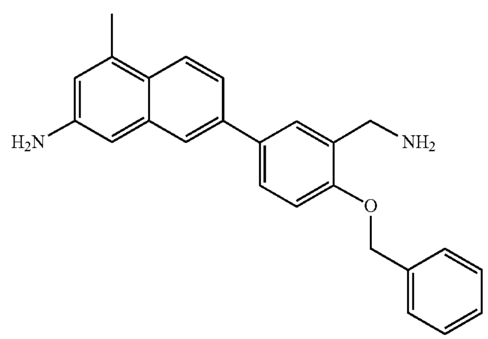
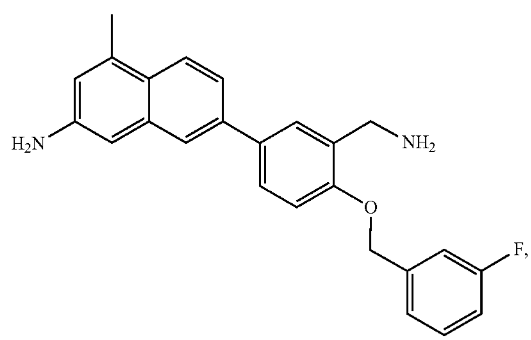
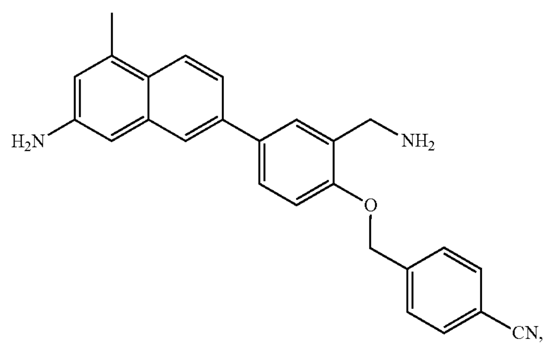
-continued
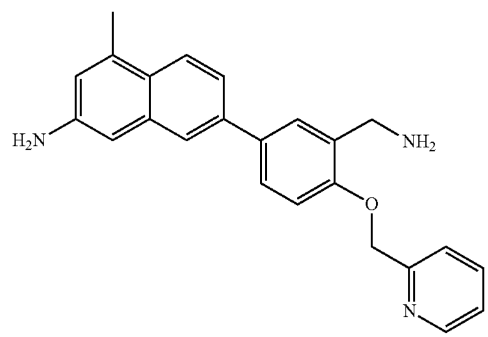
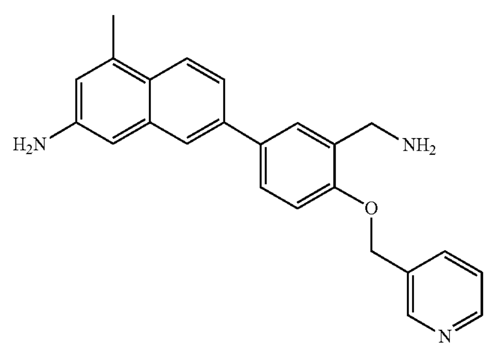
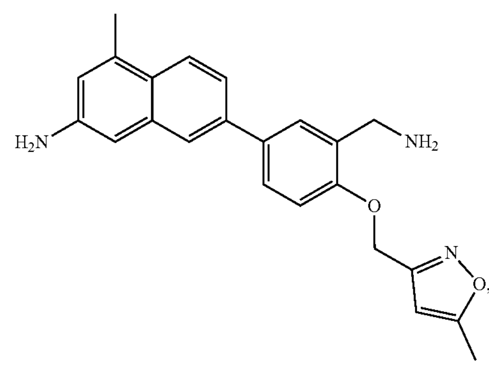
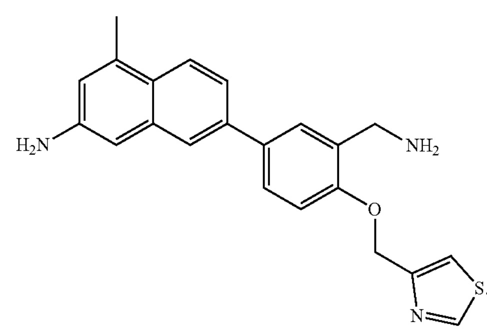
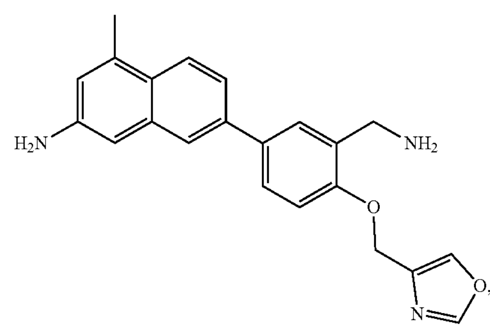

-continued

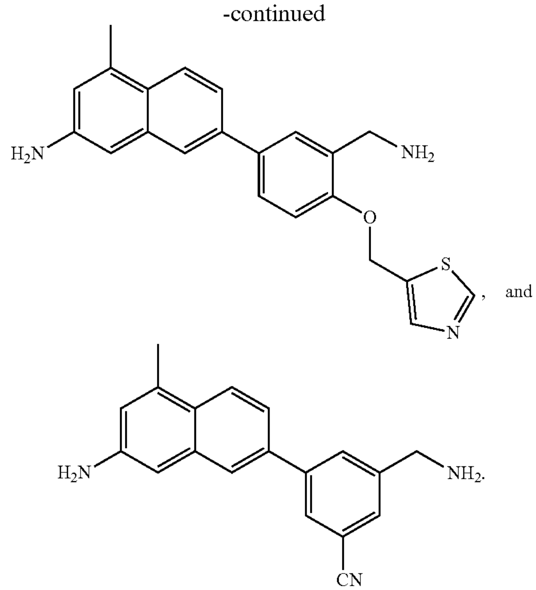

, and

Embodiment 7. The compound of any of the foregoing embodiments, wherein X is selected from alkyl-amino substituted pyridyl (e.g., alkyl-amino substituted pyridyl pyrid-2-yl, pyrid-3-yl, or pyrid-4-yl), isoindolinyl (e.g., isoindolin-3-yl or isoindolin-4yl), and amino-substituted indanyl (e.g., amino-substituted indan-5-yl or indan-6-yl); and optionally X is substituted or further substituted with a substituent selected from cyano, halo (e.g., fluoro, chloro), alkyl (e.g., ethyl), haloalkyl (e.g., trifluoromethyl), alkoxy (e.g., methoxy, ethoxy, n-propoxy, isopropoxy, isobutoxy), and substituents having a formula-$OCH_2$—Y, wherein Y is cycloalkyl, aryl, or heteroaryl and wherein Y is optionally substituted with a substituent selected from alkyl (e.g., methyl), halo (e.g., fluoro), and cyano.

Embodiment 8. The compound of embodiment 7 of a formula:

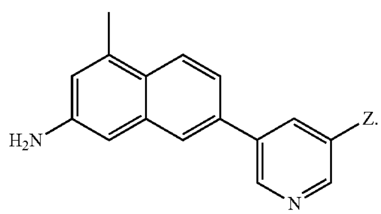

Embodiment 9. The compound of embodiment 8 of a formula:

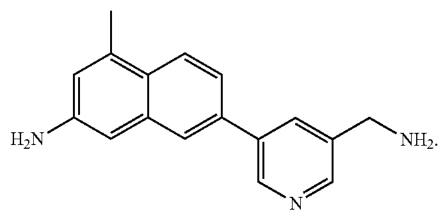 [SMILES: Cc1cc(N)cc2cc(-c3cncc(CN)c3)ccc12]

Embodiment 10. The compound of any of the foregoing embodiments, wherein X is isoindolinyl (e.g., isoindolin-3-yl or isoindolin-4yl).

Embodiment 11. The compound of any of the foregoing embodiments of a formula:

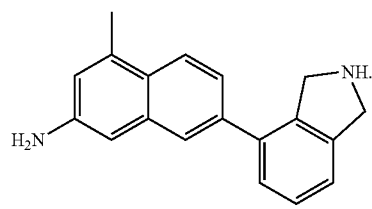 [SMILES: Cc1cc(N)cc2cc(-c3cccc4c3CNC4)ccc12]

Embodiment 12. The compound of any of the foregoing embodiments, wherein X is amino-substituted indanyl (e.g., amino-substituted indan-5-yl or indan-6-yl).

Embodiment 13. The compound of embodiment 12 of a formula:

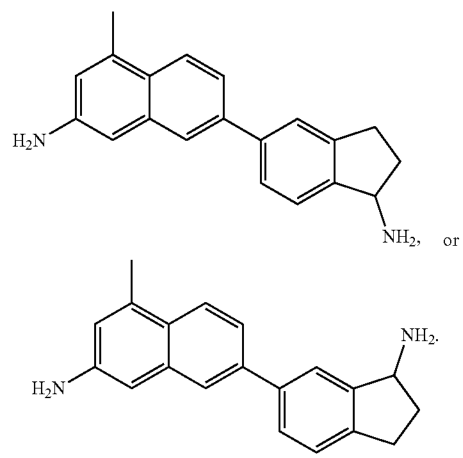

or

Embodiment 14. A pharmaceutical composition comprising the compound of any of the foregoing embodiments and a pharmaceutically acceptable carrier.

Embodiment 15. A method of treating or preventing a disease or disorder associated with nitric oxide synthase in a subject in need thereof, the method comprising administering to the subject the compound of any of embodiments 1-13 or the pharmaceutical composition of embodiment 14.

Embodiment 16. The method of embodiment 15, wherein the disease or disorder is a neurodegenerative disease or disorder.

Embodiment 17. The method of embodiment 15, wherein the disease or disorder is Alzheimer's disease.

Embodiment 18. The method of embodiment 15, wherein the disease or disorder is Huntington's disease.

Embodiment 19. The method of embodiment 15, wherein the disease or disorder is Parkinson's disease.

Embodiment 20. The method of embodiment 15, wherein the disease or disorder is amyotrophic lateral scleroris (ALS).

Embodiment 21. The method of embodiment 15, wherein the disease or disorder is cerebral palsy.

Embodiment 22. The method of embodiment 15, wherein the disease or disorder is a migraine.

Embodiment 23. A method of inhibiting nitric oxide synthase (NOS) in a cell, the method comprising contacting the cell with any of the compounds of embodiments 1-13.

Embodiment 24. The method of embodiment 23, wherein the NOS is neuronal NOS.

EXAMPLES

Example 1—First Contact: 7-Phenyl-2-Aminoquinolines, Potent and Selective Neuronal Nitric Oxide Synthase Inhibitors That Target an Isoform-Specific Aspartate Reference is made to the manuscript entitled "First Contact: 7-Phenyl-2-Aminoquinolines, Potent and Selective Neuronal Nitric Oxide Synthase Inhibitors That Target an Isoform-Specific Aspartate," authored by Maris A. Cinelli, Cory T. Reidl, Huiying Li, Georges Chreifi, Thomas L. Poulos, and Richard B. Silverman, J. Med. Chem. 2020 May 14; 63 (9): 4528-4554, Epub 2020 Apr. 7, which is incorporated herein by reference in its entirety.

Abstract

Inhibition of neuronal nitric oxide synthase (nNOS), an enzyme implicated in neurodegenerative disorders, is an attractive strategy for treating or preventing these diseases. We previously developed several classes of 2-aminoquinoline-based nNOS inhibitors, but these compounds had drawbacks including off-target promiscuity, low activity against human nNOS, and only modest selectivity for nNOS over related enzymes. In this study, we synthesized new nNOS inhibitors based on 7-phenyl-2-aminoquinoline and assayed them against rat and human nNOS, human eNOS, and murine and (in some cases) human iNOS. Compounds with a meta-relationship between the aminoquinoline and a positively charged tail moiety were potent and had up to nearly 900-fold selectivity for human nNOS over human eNOS. X-ray crystallography indicates that the amino groups of some compounds occupy a water-filled pocket surrounding an nNOS-specific aspartate residue (absent in eNOS). This interaction was confirmed by mutagenesis studies, making 7-phenyl-2-aminoquinolines the first aminoquinolines to interact with this residue.

Introduction

Neurodegenerative diseases such as Alzheimer's, Huntington's, Parkinson's, and amyotrophic lateral sclerosis (ALS), are characterized by the gradual loss of neuronal integrity and are responsible for a wide range of neurological deficiencies. Neuronal damage or death associated with stroke, ischemic events, and cerebral palsy (as well as acute or chronic brain injuries) has also been linked to similarly debilitating motor, cognitive, and psychological impairments. The overproduction of the vital secondary messenger nitric oxide (NO), produced by neuronal nitric oxide synthase (nNOS) in tissues of the central (CNS) and peripheral nervous system (PNS), is directly implicated in these disorders.[1,2] Because NO plays a key role in these diseases, rational control of NO levels in neuronal tissues via nNOS-specific inhibition is therapeutically desirable.

Nitric oxide synthases (NOSs) are a family of homodimeric enzymes that are responsible for the biosynthesis of NO. Functional regulation of NO is differentiated by subcellular localization, tissue distribution, and regulatory gene expression of three isoforms of NOS: endothelial NOS (eNOS), inducible NOS (iNOS), and neuronal NOS (nNOS), which are responsible for regulating blood pressure and vascular tone, immune activation, and normal neuronal communication, respectively.[3] Functional NOS is a homodimer. Each NOS monomer contains a reductase domain and an oxygenase domain, separated by a flexible region where calmodulin binds when activated by calcium ions. The reductase domain contains binding sites for flavin adenine dinucleotide (FAD), flavin mononucleotide (FMN), and reduced nicotinamide adenine dinucleotide phosphate (NADPH), whereas the oxygenase domain contains binding sites for (6R)-5,6,7,8-tetrahydrobiopterin (H4B), the metallocofactor heme, and the substrate L-arginine. Electron flow proceeds from one monomer's reductase domain, sequentially through NADPH, FAD, and FMN, to the opposite monomer's oxygenase domain, where the electron is transferred between FMN and heme, by which L-arginine is oxidized to L-citrulline and NO.[4]

Most compounds initially investigated for nNOS inhibition were designed as competitive mimics of L-arginine. These inhibitors have high basicity and polarity, a large total polar surface area (tPSA), and an overabundance of hydrogen bond donors, and as a result, suffer from poor bioavailability and blood-brain barrier (BBB) penetrability. Furthermore, many promising L-arginine-mimetic inhibitors are not nNOS-selective, owing to the high sequence similarity and nearly identical active-site architecture between the three NOS isoforms. High nNOS selectivity is crucial; non-selective inhibitors have the potential for dangerous side effects. For example, iNOS inhibition could impair immune system activation, while eNOS inhibition can lead to severe hypertension or other cardiovascular complications.[5]

We have been investigating 2-aminoquinoline-based scaffolds as isoform-selective arginine bioisosteres with more favorable pharmacokinetic properties. Since 2014, we have reported several generations of aminoquinolines that are modestly potent and selective towards nNOS (FIG. 1). The first generation of aminoquinolines (such as 1[6]), were found to be potent and selective nNOS inhibitors with improved pharmacokinetics. Unfortunately, 1 was found to have high rat nNOS (mNOS) over human nNOS (hnNOS) selectivity, low selectivity for hnNOS over human eNOS (heNOS), and caused toxic side effects, possibly because of its off-target promiscuity. The second generation of NOS inhibitors, (e.g., phenyl ether 2[7]) reduced off-target binding while preserving potency and selectivity against mnNOS. However, these compounds suffered from decreased Caco-2 permeability, low hnNOS activity, and similarly low hn/heNOS selectivity. Newer generation inhibitors, such as 3 and 4, improved upon their respective parent series by incorporating elements such as the quinoline 4-methyl group and cyano-containing tail moieties.[8,9] These compounds have greatly enhanced hnNOS potency, hn/heNOS selectivity, and improved cellular permeability and off-target profiles.

Because of some of the drawbacks associated with previous inhibitor generations, we have been investigating alternative aminoquinoline-containing scaffolds. Interestingly, the 7-phenylquinoline compound 5 appears in the literature as part of a Glaxo-SmithKline screening library and was recently employed in several high-throughput screening studies.[10,11] There are no articles, patents, or other reports of what research program this compound may have belonged to originally, but it appears to now be part of an "open source" drug discovery program.

Figure 2:
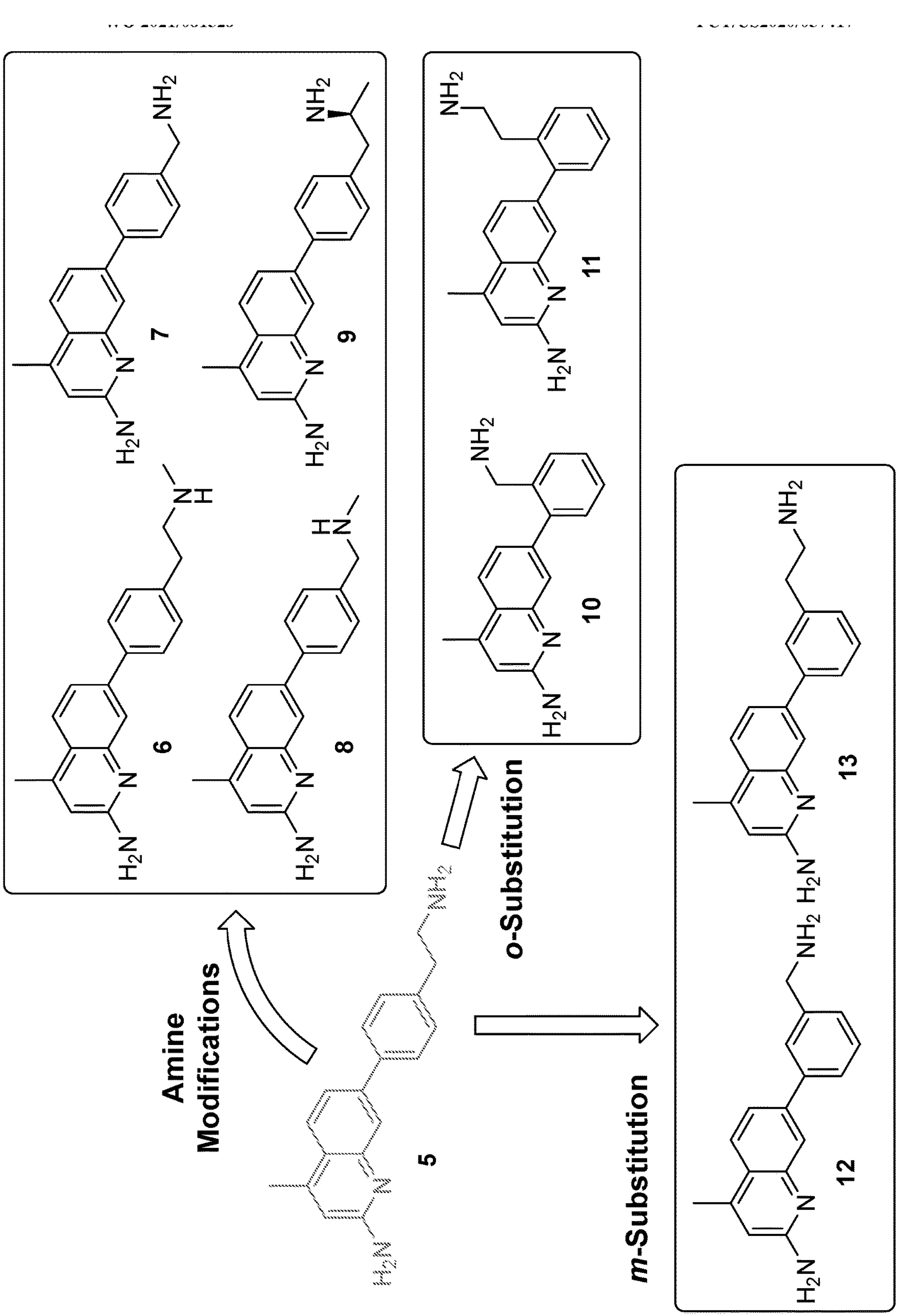
FIG. 2. Initial derivatives of 5 prepared in this study.

Because of its distinctively nNOS inhibitor-like structure, but with fewer rotatable bonds than earlier studies, a docking study with 5 in a nNOS crystal structure was conducted. Consequently, 5 was predicted to bind in an nNOS inhibitor-like mode, in which the aminoquinoline forms a salt-bridge with Glu592/Glu597 (rnNOS/hnNOS) and the phenethylamine tail portion faces out toward the regions of the active site. To this end, lead compound 5 and related compounds 6-9 (modified at the amine portion (FIG. 2) were designed, synthesized, and assayed against purified NOS isoforms to test the hypothesis that 5 and analogues could act as nNOS inhibitors. Satisfyingly, these compounds possessed encouraging nNOS inhibitory activity and good isoform selectivity, and we chose to undertake a more thorough structure-activity relationship (SAR) study. First, we investigated whether meta- or ortho-substitution of the central phenyl ring (compounds 10-13) might be more effective than the para-substitution of the parent compound. This early optimization revealed that meta-substituted analogue 12 displayed good inhibitory potency against rat and human nNOS, excellent hn/heNOS selectivity and n/i selectivity, as well as good solubility and desirable properties (few rotatable bonds and low tPSA).

Encouraged by both the inhibitory constants and the agreement between X-ray crystallography and our docking results (data not shown), 12 was used as a launching point for further optimization. We developed a set of compounds with modifications made at the 5-position of the central phenyl ring (e.g., nitrile 14 and pyridine 15) to investigate whether additional interactions could be made with the heme propionate or another active site residue.

Because of 12's high n/eNOS selectivity, we hypothesized that the flexible tail amino group might be contacting (directly or otherwise) a specific aspartate residue (Asp597/Asp602 in rnNOS/hnNOS, respectively). This residue is missing in eNOS isoforms, replaced by asparagine. Consequently, contact (H-bonding or electrostatic) between an inhibitor and this residue can impart very high n/eNOS selectivity (1000-fold or more). We hypothesized that a second set of compounds could be designed to solidify any existing contacts with Asp597/Asp602 by incorporating the tail amino group functionality into a rigid ring system, thereby reducing its overall flexibility and locking the interaction in place. As the amino group of 5 is quite flexible, both meta-/para- and ortho-/meta-constrained derivatives (isoindoline 16 and the two isomeric racemic indanylamines 17 and 18) were prepared.

Figure 3:
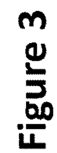
FIG. 3. Optimization of 12 by 5-substitution, amino group constraint, and 4-substitution.

Additional docking studies indicated that a variety of groups might be accommodated at the 4-position of the central phenyl ring of 12, which could form van der Waals interactions with Met336/Met341 (mNOS/hnNOS), a residue that was previously implicated in high n/eNOS selectivity for 2-aminoquinoline-based inhibitors as it is absent in eNOS isoforms (replaced by a smaller valine).[12] To this end, 3,4-substituted compounds 19-37 (FIG. 3), possessing a variety of steric, electronic, and H-bonding substituents at the 4-positions were investigated to determine if this substitution pattern could make extra contacts with the isoform-specific residues Met336/Met341 and/or the hnNOS-specific residue His342.

All synthesized compounds were assayed against rnNOS, and select compounds were also assayed against hnNOS. Murine iNOS and human eNOS were used to determine selectivity, and select compounds were also assayed against human iNOS.

Results and Discussion

Chemistry. To prepare compound 5, we envisioned that the quinoline-aryl bond could be constructed via Suzuki coupling. To this end, we sought to install the boron-containing moiety on the quinoline, taking advantage of a large and diverse set of available aryl halides (which are less expensive and easier to synthesize than an analogous series of boronates or boronic esters). Using versatile 7-bromoquinoline 38, a 7-BPin moiety was first installed via Miyaura borylation (Scheme 1). This intermediate was not isolated but rather converted to trifluoroborate 39, which was readily purified because of its insolubility in most organic solvents.

Scheme 1. Synthesis of Lead 5[a]

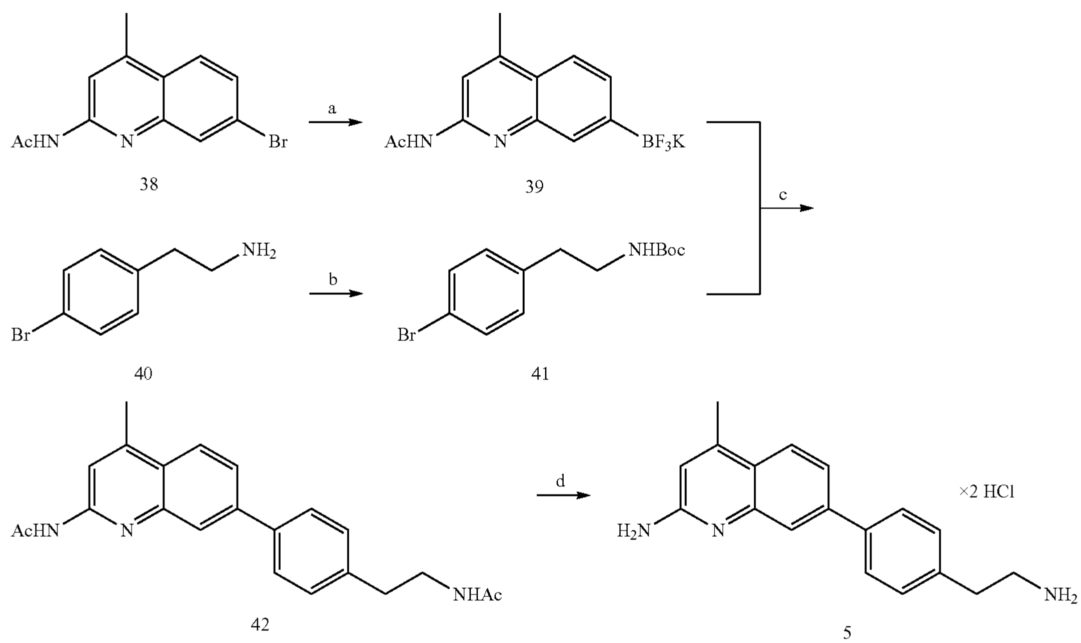

38
39
40
41
42
5

[a]Reagents and conditions: (a) i. $B_2Pin_2$, KOAc, Pd(dppf)$Cl_2$, dioxane, 75° C.; ii. $KHF_2$, THF/$H_2O$, r.t.; (b) $Boc_2O$, THF, r.t.; (c) Pd(dppf)$Cl_2$, $NaHCO_3$, 1,2-dimethoxyethane (DME)/$H_2O$, μwave, 120° C.; (d) i. $K_2CO_3$, MeOH, reflux; ii. HCl/MeOH, ether, r.t. (after isolation).

To prepare the halide precursor, commercially available 4-bromophenethylamine 40 was Boc-protected to yield 41. Many Suzuki conditions were screened for the coupling of 39 and 41, but the strong protic bases usually required for reductive elimination and activation of 39 often led to deacetylation of the quinoline and decomposition. The use of $NaHCO_3$as the base[13] in a mixed aqueous solvent was more successful, and microwave irradiation of this mixture yielded phenylquinoline 42 within 25 minutes at 120° C. without substantial deacetylation. The intermediate protected phenylquinolines were not extensively characterized but were isolated and immediately deprotected. Deprotection was accomplished stepwise, first with $K_2CO_3$ in refluxing methanol to cleave the acetyl group, followed by treatment of the free aminoquinoline with methanolic HCl to remove the Boc group and provide 5 as its water-soluble dihydrochloride salt.

To prepare the initial set of derivatives with different para-aminoalkyl tail portions (6-9), the halides were first prepared. Compound 41 was methylated to yield 43 (Scheme 2A). Commercially available iodobenzylamine 44 was Boc-protected to yield 45, which was also methylated to yield 46 (Scheme 2B). For the(S)-alpha-methyl-phenethylamine group of 9, the Ellman auxiliary method[14] was used (Scheme 2C). Ketone 47 was condensed with(S)-tert-butylsulfinamide, and the intermediate sulfinyl imine was reduced at low temperature to afford (S,S)-48 in a good d.r. of ~7:1.

Scheme 2. Preparation of Precursor p-, o-, and m- substituted Halides[a]

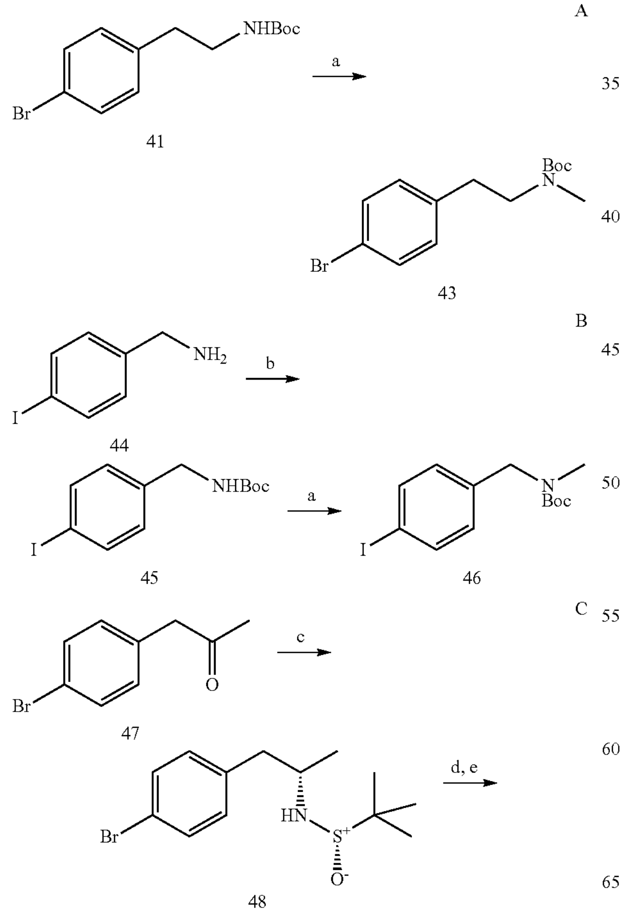

41

43

44

45

46

47

48

-continued

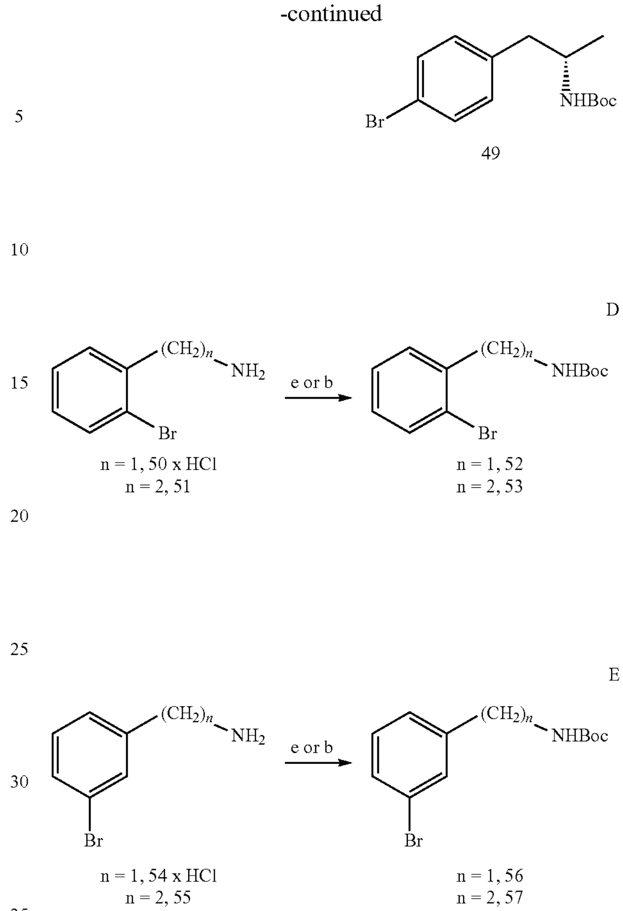

49 n = 1, 50 x HCl
n = 2, 51 n = 1, 52
n = 2, 53 n = 1, 54 x HCl
n = 2, 55 n = 1, 56
n = 2, 57

[a]Reagents and conditions: (a) (i) NaH, THF, 0° C. to r.t.; (ii) MeI, r.t. or reflux; (b) $Boc_2O$, THF, r.t.; (c) (i) (S)-t-butylsulfinamide, $Ti(OEt)_4$, THF, 70° C.; (ii) $NaBH_4$, THF, -40° C.; (d) (i) HCl/MeOH, ether, r.t.; (e) $Boc_2O$, $Et_3N$, THF/MeOH, r.t.

Desulfinylation under acidic conditions and Boc-protection. subsequently afforded derivative 49. For ortho- and meta-substituted derivatives 10/11 and 12/13, respectively, the commercially available benzylamines (50, 54) and phenethylamines (51, 55) were Boc-protected to yield o-substituted (52, 53) and m-substituted (56, 57) bromides, respectively (Schemes 2D and 2E). Suzuki coupling between 39 and these halides under the conditions described above (Scheme 3) was facile and displayed a high substrate tolerance, affording protected phenylquinolines 58-65 in good yields. Generally, the only impurity isolated was a small amount (<10%) of proto-deborylated acetamidoquinoline. Deprotection of 58-66 (Scheme 3) afforded analogues 6-13.

Scheme 3. Assembly and Deprotection of p-, o-, and m-Subsituted Phenylquinolines[a]

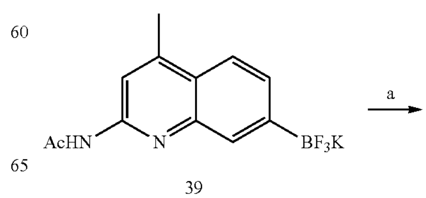

39

-continued

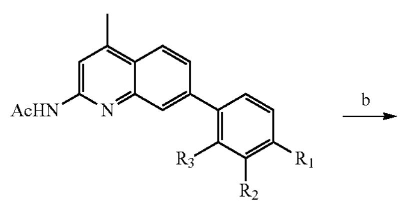

$R_2$, $R_3$ = H, $R_1$ = 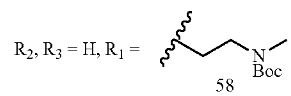

58

$R_2$, $R_3$ = H, $R_1$ = 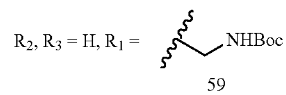

59

$R_2$, $R_3$ = H, $R_1$ = 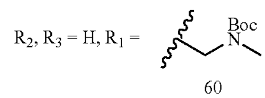

60

$R_2$, $R_3$ = H, $R_1$ = 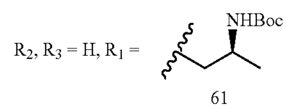

61

$R_1$, $R_2$ = H, $R_3$ = 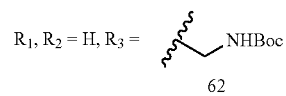

62

$R_1$, $R_2$ = H, $R_3$ = 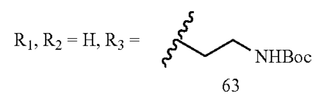

63

$R_1$, $R_3$ = H, $R_2$ = 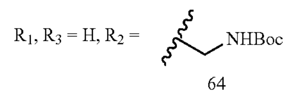

64

$R_1$, $R_3$ = H, $R_2$ = 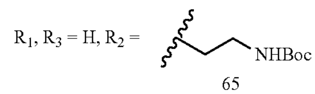

65

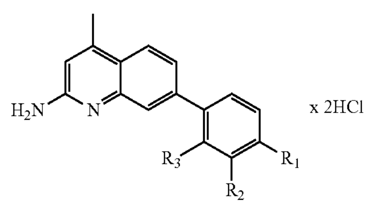

x 2HCl $R_2$, $R_3$ = H, $R_1$ = 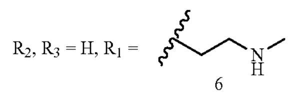

6

$R_2$, $R_3$ = H, $R_1$ = 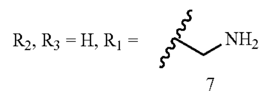

7

$R_2$, $R_3$ = H, $R_1$ = 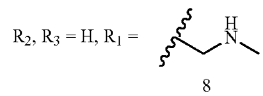

8

-continued $R_2$, $R_3$ = H, $R_1$ = 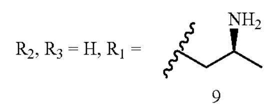

9

$R_1$, $R_2$ = H, $R_3$ = 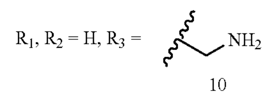

10

$R_1$, $R_2$ = H, $R_3$ = 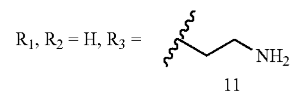

11

$R_1$, $R_3$ = H, $R_2$ = 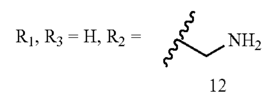

12

$R_1$, $R_3$ = H, $R_2$ = 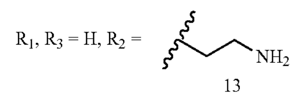

13

[a]Reagents and conditions:
a halides 43, 45-46, 49, 52-53, 56-57, Pd(dppf)$Cl_2$, $NaHCO_3$, 1,2-dimethoxyethane (DME)/$H_2O$, microwave, 120° C.;
b (i) $K_2CO_3$, MeOH, reflux; (ii) HCl/MeOH, ether, r.t. (after isolation).

Scheme 4. Synthesis of 14 and 15[a]

A

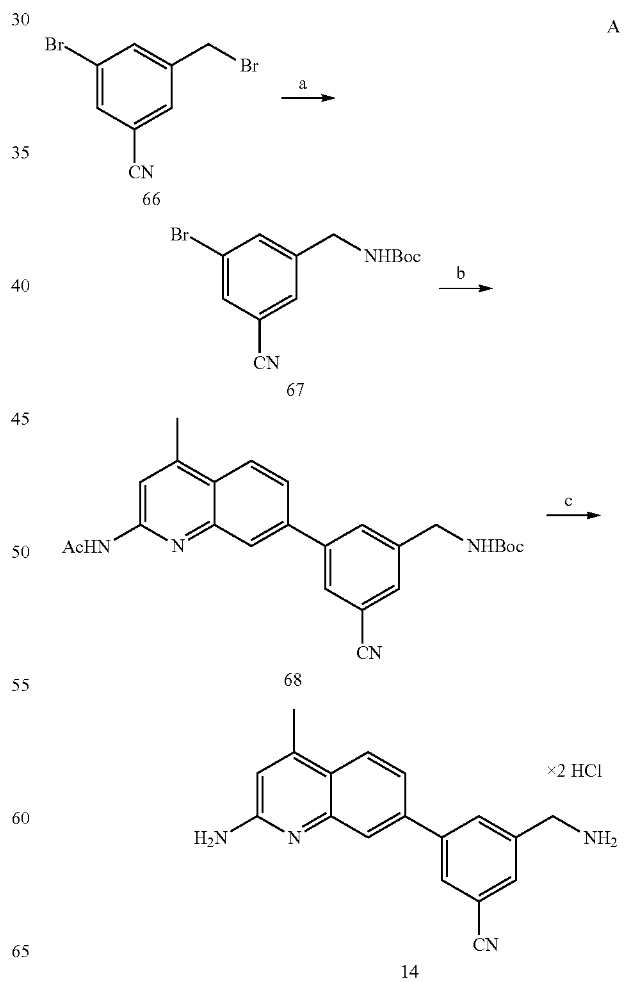

66

67

68

14

-continued

B

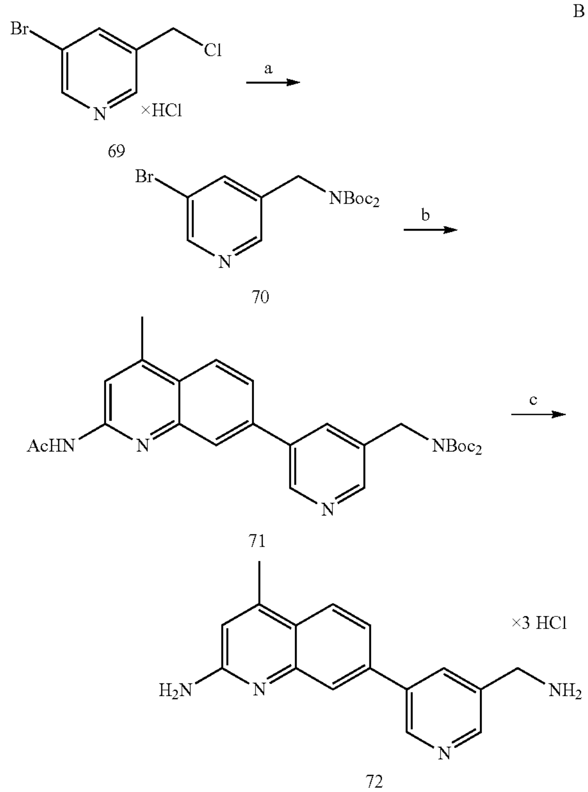

69

70

71

72

[a]Reagents and conditions: (a) (i) NaH, $Boc_2NH$, THF, r.t,; (ii) halide, r.t. or r.t. -50° C. (for 69); (b) 39, $Pd(dppf)Cl_2$, $NaHCO_3$, 1,2-dimethoxyethane (DME)/$H_2O$, microwave, 120° C.; (c) (i) $K_2CO_3$, MeOH, reflux; (ii) HCl/MeOH, reflux; (ii) HCl/MeOH, ether, r.t. (after isolation).

To synthesize 5-cyano derivative 14, bromobenzene 66 was prepared as previously described. Treatment of 66 with the anion derived from $Boc_2NH$ (Scheme 4A) yielded, surprisingly, mono-Boc protected amine 67, indicating that one Boc group was cleaved during the reaction or workup. Suzuki coupling with 39 yielded 68, which was then deprotected to provide amine 14. In contrast, heating $Boc_2NH$ and pyridine 69 under basic conditions (Scheme 4B) afforded the N,N-di-Boc compound (70).[15] Likewise, the major product (71) isolated upon coupling of 70 and 39 contained both Boc groups intact. During deacetylation, a longer period of heating (4.5 h) was employed to remove both the acetyl group and one Boc group, and the second Boc group was then removed with HCl to yield 15.

Synthesis of isoindoline derivative 16 (Scheme 5A) commenced with commercially available 4-bromoisoindoline salt 72, which was converted to the free base and Boc-protected to yield 73. Coupling with 39 afforded 74, which then yielded 16 upon deprotection. Indanylamine derivatives 17 and 18 (Scheme 5B) were prepared from the 5- and 6-bromoindanones (75 and 76), respectively. The Ellman method (as in Scheme 2C) was used to install the amino group as its racemate. However, yields of sulfinamides 77 and 78 were fairly low, and large amounts of insoluble ketone condensation by-products were obtained. Nonetheless, 77 and 78 were desulfinylated and Boc-protected, and carbamates 79 and 80 were readily amenable to Suzuki coupling with 39, affording 81 and 82, which were deprotected to yield, respectively, 17 and 18.

Scheme 5. Synthesis of Conformationally Constrained Derivatives 16-18[a]

A

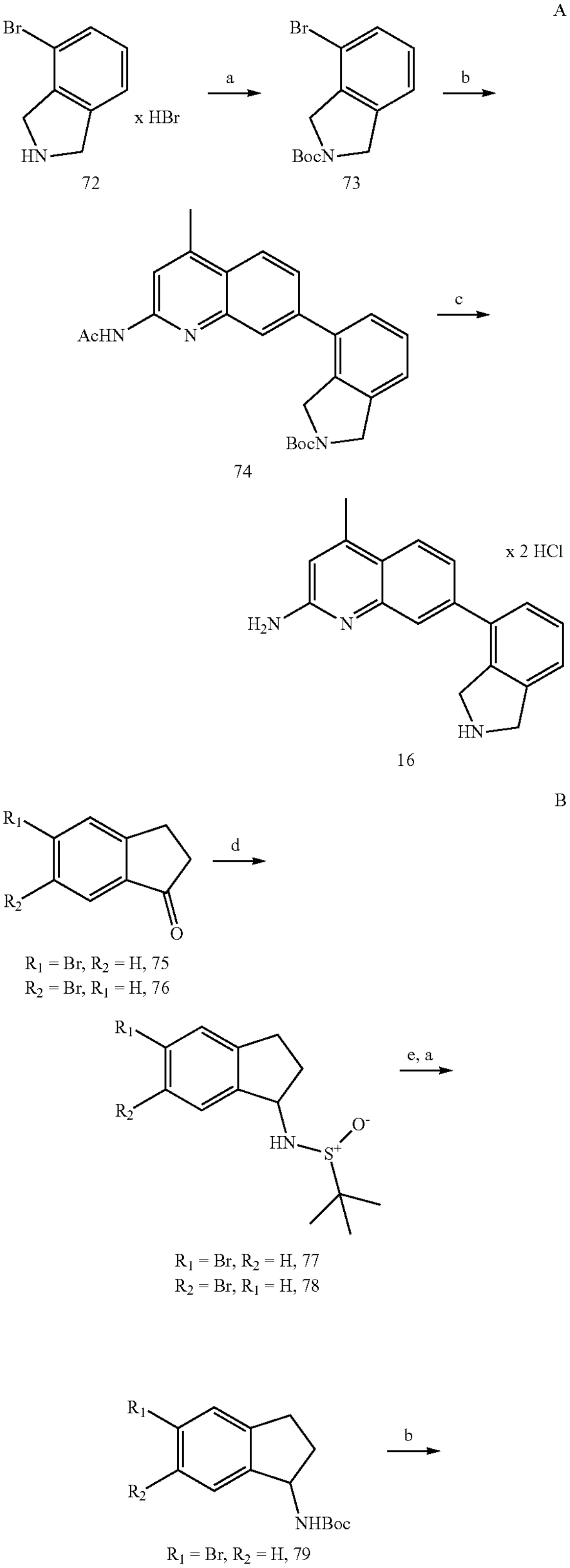

x HBr a b

72

73 c

74 x 2 HCl

16

B d $R_1$ = Br, $R_2$ = H, 75
$R_2$ = Br, $R_1$ = H, 76 e, a $R_1$ = Br, $R_2$ = H, 77
$R_2$ = Br, $R_1$ = H, 78 b $R_1$ = Br, $R_2$ = H, 79
$R_2$ = Br, $R_1$ = H, 80

-continued

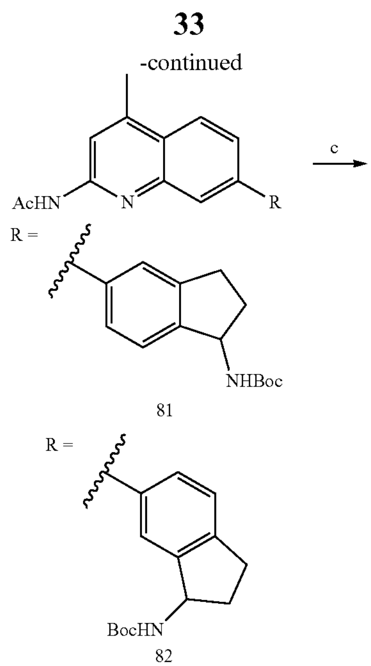

81

82

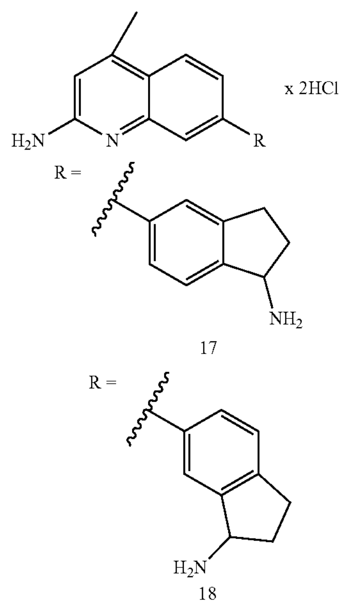

17

18

[a]Reagents and conditions:
a $Boc_2O$, $Et_3N$, THF/MeOH, r.t.;
b 39, $Pd(dppf)Cl_2$, $NaHCO_3$, 1,2-dimethoxyethane (DME)/$H_2O$, microwave, 120° C.;
c (i) $K_2CO_3$, MeOH, reflux; (ii) HCl/MeOH, ether, r.t. (after isolation);
d (i) (RS)-t-butylsulfinamide, $(Ti(OEt)_4$, THF, 70° C.; (ii) $NaBH_4$, THF, -40° C.;
e (i) HCl/MeOH, ether, r.t.

We envisioned that 4-substituted derivatives 19-24 could be accessed from commercially available benzaldehydes or toluene derivatives via conversion to the benzyl halides. To this end, fluorotoluene 83 and chlorotoluene 84 (for 19 and 20) were converted to benzyl bromides 85 and 86. A Delépine reaction, involving treatment with hexamethylenetetramine and acidic hydrolysis of the resulting hexaminium adduct, and subsequent Boc-protection of the amine yielded 87 and 88 (Scheme 6A). For the trifluoromethyl derivative en route to 21, commercially available nitrile 90 was reduced with $BH_3$-DMS,[16] and the isolated amine was protected to yield 91 (Scheme 6B). 2-Ethybenzaldehyde (91, for 22) was complexed with $AlCl_3$[17] and brominated to yield the major regioisomer (92b) as an inseparable 3:1 mixture with 92a. Following borohydride reduction, the isomers were separated, and the major isomer (93) was chlorinated to yield 94. A Delépine reaction and Boc protection provided bromobenzene derivative 95 (Scheme 6C).

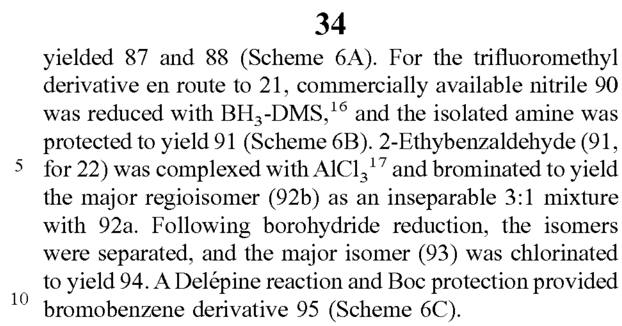

Scheme 6A. Synthesis of Intermediate 87 and 88 Carbamates for the Preparation of 4-Substituted Derivative[a]

A

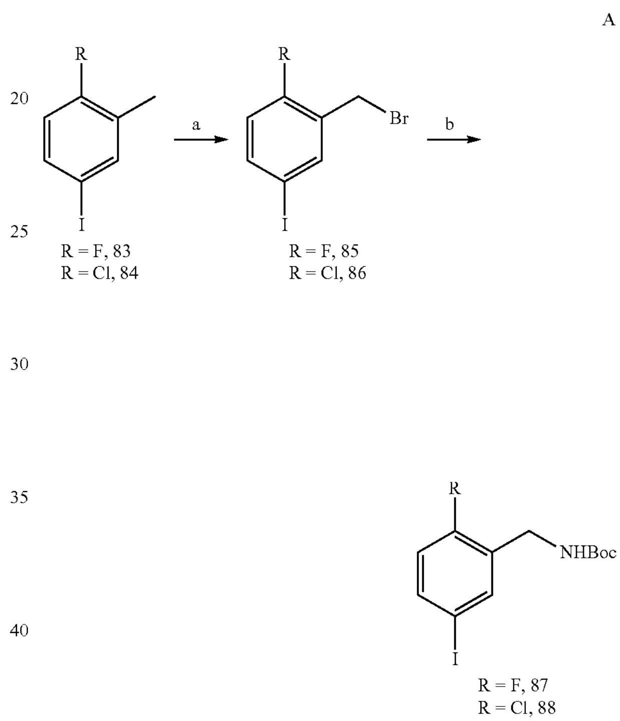

R = F, 83
R = Cl, 84

R = F, 85
R = Cl, 86

R = F, 87
R = Cl, 88

[a]Reagents and conditions: (a) NBS, $(PhCO_2)_2$, $CCl_4$, reflux; (b) (i) HMTA, NaI, EtOH, r.t.; (ii) HCl, reflux; (iii) $Boc_2O$, THF (after isolation).

Scheme 6B. Synthesis of Intermediate 90 Carbamate for the Preparation of 4-Substituted Derivative[a]

B

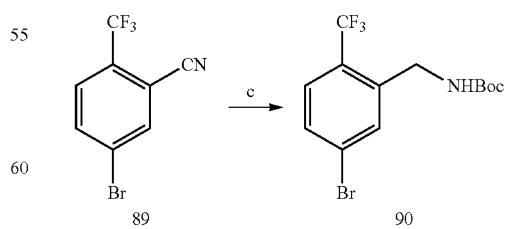

89

90

[a]Reagents and conditions:
c (i) $BH_3$—$Me_2S$, THF, 0° C. to reflux; (ii) HCl, reflux; (iii) $Boc_2O$, THF, r.t. (after isolation).

Scheme 6C. Synthesis of Intermediate 94 Carbamate for the Preparation of 4-Substituted Derivative[a]

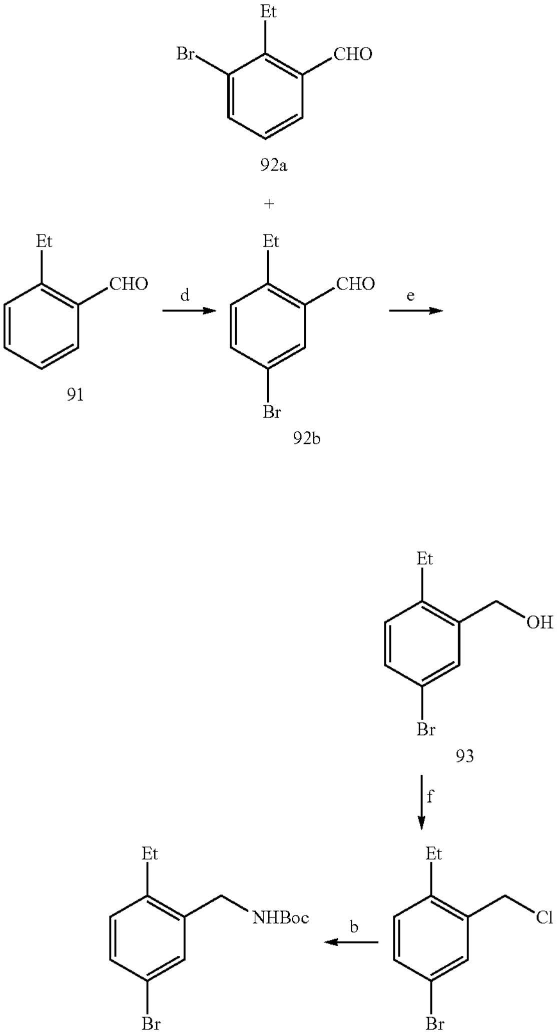

92a

+

91

92b

93

95

94

[a]Reagents and conditions: (b) (i) HMTA, NaI, EtOH, r.t.; (ii) HCl, reflux; (iii) $Boc_2O$, THF (after isolation); (d) $Br_2$, $AlCl_3$, $CH_2Cl_2$, ° C. to r.t.; (e) $NaBH_4$, MeOH, r.t.

Scheme 6D. Synthesis of Intermediate 98 Carbamate for the Preparation of 4-Substituted Derivative[a]

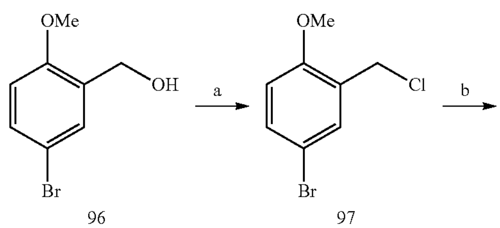

96

97

-continued

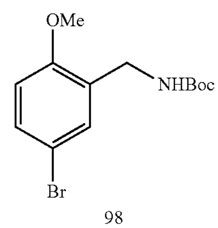

98

[a]Reagents and conditions: (b) (i) HMTA, NaI, EtOH, r.t.; (ii) HCl, reflux; (iii) $Boc_2O$, THF, (after isolation); (f) $SOCl_2$, $CH_2Cl_2$, ° C. to r.t.

Scheme 6E. Synthesis of Intermediate 101 Carbamate for the Preparation of 4-Substituted Derivative[a]

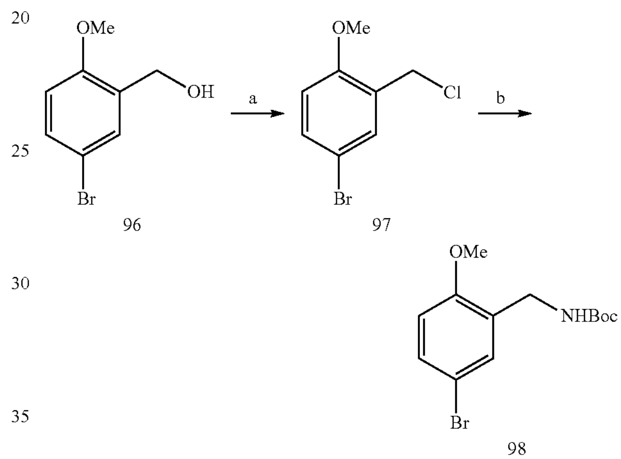

96

97

98

[a]Reagents and conditions: (a) NBS, $(PhCO_2)_2$, $CCl_4$, reflux; (b) (i) HMTA, NaI, EtOH, r.t.; (ii) HCl, reflux; (iii) $Boc_2O$, THF (after isolation).

Methoxybenzyl alcohol 96 (for 23) was prepared as previously described (Scheme 6D) and elaborated via 97 as described above to yield 98. Finally, ethoxylated toluene 99 was brominated to yield 100 (Scheme 6E). A Delépine reaction and Boc protection afforded carbamate 101.

As the multiple steps of this route would make the preparation of many similar analogues time consuming, and the $Boc_2NH$ method of Scheme 4 was unpredictable, a slightly different strategy was used to prepare 4-ether halide derivatives 25-37 (Scheme 7). In this route, protected amine 103 was first prepared via reduction of 102, and then the ether functionality was installed by deprotonation of the phenol and treatment with alkyl or benzyl halides.

Scheme 7. Preparaton of Ether-Substituted Carabates and Final Assembly of 4-Substituted Analogues 19-37[a]

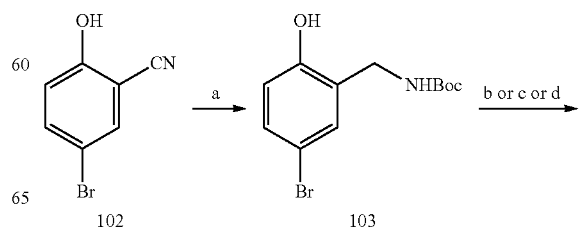

102

103

-continued

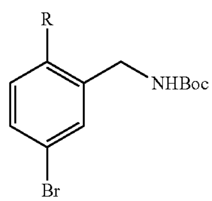

e or f

R = O-n-Pr, 104
R = O-i-Pr, 105
R = O-i-Bu, 106
R = O-methylcyclobutyl, 107
R = O-methylcyclopropyl, 108[b]
R = O-(3-fluorobenzyl), 109
R = O-(4-cyanobenzyl), 110
R = O-(2-pyridinylmethyl), 111
R = O-(3-pyridinylmethyl), 112
R = O-(5-methylisoxazol-3-yl)methyl, 113
R = O-(thiazol-4-methyl), 114
R = O-(oxazol-4-methyl), 115
R = O-(thiazol-5-methyl), 116
(or halides 87-88, 90, 95, 98, or 101)

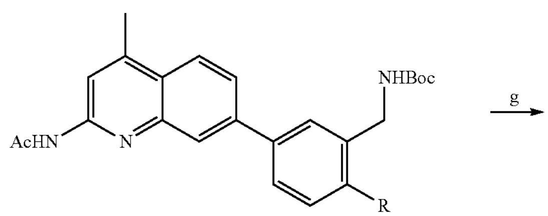

R = F, 117 R = Cl, 118
R = $CF_3$, 119 R = Et, 120
R = OMe, 121 R = OEt, 122
R = O-n-Pr, 123
R = O-i-Pr, 124
R = O-i-Bu, 125
R = O-methylcyclobutyl, 126
R = O-methylcyclopropyl, 127
R = O-(3-fluorobenzyl), 128
R = O-(4-cyanobenzyl), 129
R = O-(2-pyridinylmethyl), 130
R = O-(3-pyridinylmethyl), 131
R = O-(5-methylisoxazol-3-yl)methyl, 132
R = O-(thiazol-4-methyl), 133
R = O-(oxazol-4-methyl), 134
R = O-(thiazol-5-methyl), 135

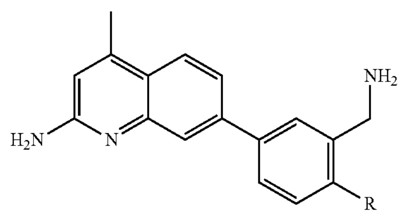

R = F, 19 R = Cl, 20
R = $CF_3$, 21 R = Et, 22
R = OMe, 23 R = OEt, 24
R = O-n-Pr, 25
R = O-i-Pr, 26
R = O-i-Bu, 27
R = O-methylcyclobutyl, 28
R = O-methylcyclopropyl, 29
R = O-(3-fluorobenzyl), 30

-continued

R = O-(4-cyanobenzyl), 31
R = O-(2-pyridinylmethyl), 32
R = O-(3-pyridinylmethyl), 33
R = O-(5-methylisoxazol-3-yl)methyl, 34
R = O-(thiazol-4-methyl), 35
R = O-(oxazol-4-methyl), 36
R = O-(thiazol-5-methyl), 27

[a]Reagents and conditions:
a (i) $BH_3$—$Me_2S$, THF, 0° C. to reflux; (ii) HCl•MeOH, reflux; (iii) $Boc_2O$, MeOH/THF, r.t. (after isolation);
b (i) NaH. N,N-dimethylformamide (DMF), 0° C.; (ii) alkyl or benzyl iodide or bromide, 0° C., to r.t.;
c alkyl bromide, $K_2CO_3$, acetone, reflux;
d heterocyclic halides, $Cs_2CO_3$, DMF, r.t.;
e 39, Pd(dppf)$Cl_2$, $NaHCO_3$, 1,2-dimethoxyethane (DME)/$H_2O$, pwave, 120° C.;
f[b] (i) $B_2(OH)_2$, KOAc, XPhos-Pd-G3, XPhos, EtOH, 80° C., 2 h; (ii) 38, $K_2CO_3$, $H_2O$, 80° C., 15 h; (
g (i) $K_2CO_3$, MeOH, reflux; (ii) HCl/MeOH, ether, r.t. (after isolation).

By this method, the n-propyl (104), isopropyl (105), isobutyl (106), methylcyclobutyl (107), methylcyclopropyl (108), 3-fluorobenzyl (109), 4-cyanobenzyl (110), (5-methylisoxazol-3-methyl (113), 4- and 5-methyl thiazoles (114/116), and oxazol-4-methyl (115) ethers were prepared. As the thiazol-5-methyl chloride and pyridylmethyl bromides are only commercially available as the HCl and HBr salts, respectively, these salts were converted to their free base immediately prior to the formation of the 2-pyridylmethyl (111), 3-pyridylmethyl (112), and thiazol-5-methyl (116) ethers. All of these ether-containing halides were subjected to Suzuki coupling with 39 to yield protected phenylquinolines 117-135 in moderate to excellent yields, and stepwise deprotection as described above yielded final analogues 19-37.

nNOS Inhibitor Assay and Crystallography. The hemoglobin capture assay (see Experimental Section) was used to determine the inhibitory constants ($K_i$) of synthesized compounds 5-37.[18,19] All compounds were assayed against purified mnNOS as a pre-screen, and eighteen of the most potent compounds against rnNOS were further assayed against purified human nNOS (hnNOS), murine iNOS (miNOS), and human eNOS (heNOS) to determine isoform selectivity. Table 1 summarizes the apparent $K_i$ values and isoform selectivities for 5-37. Values for compounds 1-4 are included for comparison. The rnNOS and miNOS isoforms were used to approximate n/i isoform selectivity because they are the easiest to express and purify, and those are the species used for crystallography. Furthermore, for preclinical purposes, it is essential to prove efficacy and selectivity in lower animals prior to advancement to clinical trials. Recent advances have made it possible to obtain and crystallize both hnNOS and heNOS, which were used to support our human isoform SAR development. Because high-resolution structures of murine or human iNOS with inhibitors bound are still not readily available, the majority of the structural discussion will focus on nNOS and eNOS; discussion of a comparison between murine and human iNOS inhibition follows that.

TABLE 1

Inhibition of NOS Enzymes by Synthesized Compounds 5-37[a]

| | $K_i$ (μM)[a] | | | | Selectivity | |
|---|---|---|---|---|---|---|
| compd | rnNOS | hnNOS | miNOS | heNOS | rn/mi | hn/he |
| 1 | 0.066 | 0.440 | 28.4 | 11.8 | 431 | 27 |
| 2 | 0.058 | 0.295 | 27.7 | 7.41 | 478 | 25 |

TABLE 1-continued

Inhibition of NOS Enzymes by Synthesized Compounds 5-37[a]

| | $K_i$ (μM)[a] | | | | Selectivity | |
|---|---|---|---|---|---|---|
| compd | rnNOS | hnNOS | miNOS | heNOS | rn/mi | hn/he |
| 3 | 0.033 | 0.031 | 6.7 | 5.63 | 203 | 181 |
| 4 | 0.025 | 0.030 | 4.83 | 5.76 | 193 | 192 |
| 5 | 0.105 | 0.122 | 21.7 | 23.3 | 207 | 191 |
| 6 | 0.246 | — | — | — | — | — |
| 7 | 0.045 | 0.088 | 16.3 | 18.7 | 362 | 212 |
| 8 | 0.090 | 0.149 | — | — | — | — |
| 9 | 0.140 | — | 27.5 | — | 197 | — |
| 10 | 0.119 | 0.151 | 2.86 | 41.9 | 24 | 277 |
| 11 | 0.935 | — | — | — | — | — |
| 12 | 0.055 | 0.060 | 24.2 | 52.6 | 440 | 877 |
| 13 | 0.107 | — | — | — | — | — |
| 14 | 1.03 | — | — | — | — | — |
| 15 | 0.285 | — | — | — | — | — |
| 16 | 0.254 | — | — | — | — | — |
| 17 | 0.159 | — | — | — | — | — |
| 18 | 0.180 | — | — | — | — | — |
| 19 | 0.108 | — | — | — | — | — |
| 20 | 0.235 | — | — | — | — | — |
| 21 | 1.42 | — | — | — | — | — |
| 22 | 0.390 | — | — | — | — | — |
| 23 | 0.106 | — | — | — | — | — |
| 24 | 0.058 | 0.111 | 24.2 | 18.2 | 418 | 164 |
| 25 | 0.072 | 0.058 | 23.9 | 12.9 | 333 | 223 |
| 26 | 0.071 | 0.066 | 25.5 | 20.2 | 360 | 307 |
| 27 | 0.062 | 0.072 | 9.66 | 5.65 | 156 | 78 |
| 28 | 0.049 | 0.096 | 10.4 | 22.8 | 212 | 238 |
| 29 | 0.039 | 0.046 | 32.8 | 21.0 | 841 | 457 |
| 30 | 0.083 | — | — | — | — | — |
| 31 | 0.055 | 0.114 | 13.5 | 8.31 | 246 | 73 |
| 32 | 0.052 | 0.076 | 45.7 | 23.7 | 879 | 312 |
| 33 | 0.044 | 0.045 | 8.18 | 7.73 | 186 | 172 |
| 34 | 0.056 | 0.106 | — | — | — | — |
| 35 | 0.043 | 0.031 | 4.32 | 6.20 | 100 | 200 |
| 36 | 0.043 | 0.063 | 16.4 | 27.3 | 382 | 433 |
| 37 | 0.053 | 0.046 | 21.0 | 20.0 | 397 | 435 |

[a]The compounds were assayed for in vitro inhibition against four purified NOS isoforms: rat nNOS (rnNOS), human nNOS (hnNOS), murine iNOS (miNOS), and human eNOS (heNOS) using known literature methods (see the Experimental Section for details), and $K_i$ values are calculated directly from $IC_{50}$ values. $IC_{50}$ values are the average of at least two replicates from 6-9 data points; all experimental standard error values (for the log $IC_{50}$) are less than 10%, and all correlation coefficients are good ($r^2 > 0.87$). Selectivity values are ratios of respective $K_i$ values.

Initial Inhibitory and Structural Analysis of Modified Amine Tail Analogues. The initial lead, 7-phenyl-2-aminoquinoline (5), has good rat and human nNOS inhibitory activity (105 nM and 122 nM, respectively) with moderately high n/iNOS and n/eNOS selectivity of 207-fold and 191-fold, respectively. The X-ray crystal structure of 5 bound to mnNOS, hnNOS, and heNOS revealed the structural basis for inhibitory potency (data not shown). The quinoline portion of 5 mimics arginine and forms a bifurcated hydrogen bond system with the main chain carbonyl of Trp587/Trp592 (mnNOS/hnNOS) and the side chain carboxylate of Glu592/Glu602 (mNOS/hnNOS). This is identical to the structural details observed for other nNOS inhibitors possessing the aminoquinoline functionality.[6-9] All three crystal structures clearly reveal that the central phenyl ring sits between heme propionates A and D. In the hnNOS-5 structure, the tail phenethylamine moiety makes a direct H-bond interaction with the $H_4B$ and propionate A, displacing the water there, while the mNOS-5 structure only makes H-bonding contacts with the carbonyl of the $H_4B$ and is unable to displace the water molecule bridging propionate A and the $H_4B$.

In heNOS there are two molecules of 5 bound. Ligand A binds as expected in the active site and is very similar to the nNOS structures, while Ligand B displaces HAB with the aminoquinoline positioned in the pterin binding pocket. As a result, the tail ethylamine of 5 bound to heNOS is oriented in the opposite direction to what we observed in the nNOS structures, and instead interacts with propionate D. Ligand B is stabilized by aromatic stacking interactions with both Trp447 as well as Trp74 and Phe460 from the opposite chain at the dimer interface. Two-site binding is not unique to 5 and has been observed in several NOS-inhibitor structures.[20,21] In all four molecules of the asymmetric unit of heNOS, the aminoquinoline and phenyl rings of 5 are clearly defined. The electron density is weaker for the tail ethylamines, with slightly more density observed near propionate D, indicating a potential interaction with the heme propionate. Interestingly, the ability of 5 and other compounds to bind in both sites has little correlation with inhibitory potency, indicating active site binding, but not the ability to displace the $H_4B$, determines potency.

With the goal of improving hnNOS activity and isoform selectivity, we made efforts to optimize the conformational positioning of the tail amine of 5. To this end, homologation, chain shortening, and isomerization of lead molecule 5 resulted in compounds 6-13. Methylation of the tail nitrogen atom of 5 (compound 6) resulted in over a 2-fold loss in mnNOS activity, while shortening the ethylene linker between the central ring and the terminal nitrogen atom by one carbon (compound 7) resulted in a 2.3-fold increase in rnNOS activity. Moreover, 7 showed increased hnNOS inhibitory activity, as well as improvements in both rn/miNOS and hn/heNOS selectivity ratios, relative to parent molecule 5. The X-ray crystal structures of 7 bound to mNOS and hnNOS reveal well-defined density at the aminoquinoline and central ring regions that closely overlaps with lead 5 (data not shown). However, the orientation of the tail aminomethyl group in both structures could not be determined because of poor density, even at a low contour levels, suggesting free rotation of the aminomethyl occurs toward either propionate A and the $H_4B$ site water or toward propionate D and Tyr706/Tyr711 (mnNOS/hnNOS) (data not shown). In both nNOS structures, the position of the central phenyl ring of 7 forces heme propionate D into a downward conformation. As observed for 5 and 6, methylation of the tail nitrogen atom of 7 to yield 8 again resulted in a loss of potency against both rat and human nNOS, suggesting that a primary amino group at this position is important for achieving maximal inhibitory activity against nNOS isoforms.

It appears that some parts of the phenylaminoquinoline SAR overlap with that of the previously reported phenyl ether compounds. For example, phenyl ether compounds with one methylene between the amino group and the aryl ring (benzyl) are more potent and selective than those with two or more methylenes (phenethyl), and the same trend is observed here (cf. 7 and 8 vs. 5 and 6). Likewise, compound 9 ($K_i$ (mnNOS)=140 nM) has slightly less potency than 7. Nonetheless, other parts of the SAR are distinct from the previous generation of aminoquinoline NOS inhibitors; for instance, N-methylated compounds (6, 8) appear less potent than the desmethyl analogues (5, 7). This appears to be the reverse of what was generally observed for benzyl and phenethyl ether compounds.

The o-substituted isomers (11 and 10) were shown to possess less inhibitory potency (11, $K_i$ (mNOS)=935 nM; 10, $K_i$ (mNOS)=119 nM) than their corresponding para-substituted derivatives 5 and 7, respectively. Furthermore, 10 displays a similar loss in hnNOS potency and a sharp decrease in rn/miNOS selectivity. However, poor binding affinity with heNOS (10, $K_i$ (heNOS)=41,900 nM) results in a gain in hnNOS selectivity over heNOS compared to 7. In contrast to the o-substituted isomers, m-substituted isomers 13 and 12 exhibited comparable potencies to 5 and 7, respectively [13, $K_i$ (mNOS)=107 nM; 12, $K_i$ (rnNOS)=55 nM]. Moreover, 12 also has very good nNOS selectivity over iNOS (rn/miNOS=440) and outstanding selectivity over eNOS (hn/heNOS=877). The kinetic data for 12 suggests that placing the aminoalkyl tail portion meta- to the quinoline favors binding to the human nNOS isoform, which prompted us to check the crystal structures of both mNOS-12 and hnNOS-12. In X-ray crystal structures, we observed that the tail amino group in the meta-position of the benzene ring may participate in maximal binding interactions with a water-filled polar pocket made up by the carboxylate of propionate A, the side chains of Gln478/Gln483, Arg481/Arg486, and, most notably, Asp597/Asp602 (rnNOS/hnNOS, respectively), resulting in reduced flexibility in the tail aminomethyl group (data not shown).

In sharp contrast, we observed that the tail aminomethyl group in the heNOS-12 structure shows a different orientation, making H-bonds with heme propionate A (data not shown). It is important to note that there is a major difference in the active site of human eNOS, namely, Asn366 replaces Asp597/Asp602 (rnNOS/hnNOS) in the polar pocket noted for nNOS. In earlier studies we found that this Asp/Asn difference makes substantial contributions to isoform selectivity.23 This is likely the basis for the high selectivity observed for 12 because the aminomethyl group is oriented back toward Asp597/Asp602 in the rnNOS/hnNOS structures.

We proposed that homologated analogue 13 could have improved activity because the longer chain might allowe it to potentially displace one of the structural waters near the nNOS-specific Asp residue. However, the nNOS inhibitory activity of 13 is weaker, comparable to para-substituted derivative 5 (and about two-fold lower than 12), indicating that either (a) this water molecule is not displaced, or (b) any energy gained from water displacement does not offset entropic costs of chain elongation, internal torsion, or other negative interactions between the enzyme and inhibitor. The crystal structures of rnNOS-13 and hnNOS-13 supports the former hypothesis (data not shown); the tail amino group does not occupy this polar pocket but rather displaces the water molecule bridging propionate A and the $H_4B$. Consequently, the aminoethyl group can only reach the closer heme propionate A for an electrostatic interaction, rather than the farther Asp597/Asp602 site (mNOS/hnNOS).

Previously, installation of a nitrile at the 5-position of phenyl ether-linked aminoquinolines greatly improved potency, as the nitrile fit into a small, previously undiscovered auxiliary pocket, where it formed a H-bond with a deep structural water and stabilized binding; likewise, 1,3,5-trisubstituted nitrile-containing aminopyridine derivatives[2,4] exert augmented potency and selectivity via differential interactions with the Asp site (vs. the Asn site in eNOS). For the phenylquinoline scaffold, however, the nitrile is a very deleterious modification in [14, $K_i$ (rnNOS)=10,300 nM]. Examination of the crystal structure of 12 indicated that the 5-position nitrile of the more compact and rigid phenylquinoline (compared to the more flexible phenyl ether molecule) cannot reach this auxiliary pocket (data not shown). Instead, the position of the phenyl ring of 14 (just like 12) would force heme propionate D into a downward conformation; thus, the 5-position nitrile would cause serious clashes with nearby residues. This is another area where the SARs of phenyl ether-linked aminoquinolines and phenylquinolines drastically diverge.

On the basis of the 12-bound NOS crystal structures, pyridine 15 was expected to be a potent inhibitor (data not shown). In addition to having an identical binding mode to 12, the pyridine nitrogen atom forms a hydrogen bond with heme propionate D in all three NOS structures (data not shown). The aminomethyl group of 15 approaches Gln478 in rnNOS, and is disordered but may point to Asp602 in hnNOS, and heads to the water molecule near heme propionate A in heNOS, where a second molecule of 15 is bound in the pterin site. Nonetheless, the pyridine analogue is approximately 5-fold less potent than 12 in mNOS, contradicting both the crystallographic observations and previous results observed for the pyridine-containing 2-aminopyridine and 2-aminoquinoline compounds. The unpredicted effect may be electronic, or the pyridine influences interactions of the aminomethyl group with nearby water molecules.

Constrained Amine Analogues 16-18. See Supporting Information for details.

4-Alkoxy-3-aminomethyl Analogues 19-29. Docking studies with 12 also indicated that a variety of groups can be accommodated at position 4 of the phenyl ring (data not shown). Substituents at this position could form favorable van der Waals interactions with Met336/Met341 or Leu337/His342 (rnNOS/hnNOS), residues that have previously been implicated in high n/eNOS selectivity for 2-aminoquinoline-based inhibitors, and which are replaced by Val104 and Phe105 in heNOS, respectively. To this end, 19-29, having a variety of steric, electronic, and H-bonding properties that could yield crucial SAR information, were prepared and assayed for NOS inhibitory potency. In general, small substituent modifications at the 4-position of lead 12, such as fluorine (19), chlorine (20), ethyl (22), and methoxyl (23) do not add additional good contacts in the rat nNOS active site, resulting in a loss in potency. Compound 21 is a less potent inhibitor given that the trifluoromethyl group of 21 is likely too bulky to fit. However, changing the 4-position methoxyl group (23) to an ethoxyl group (24) restored the potency in mNOS. The crystal structure of 24 bound to rnNOS shows strong density for the aminoquinoline and central phenyl ring as seen in parent compound 12 (data not shown). While the aminomethyl moiety occupies the water site between $H_4B$ and propionate A, the ethoxyl moiety is large enough to establish some contacts with Met336. It seems that as a minimum a 3-atom, nonpolar moiety at the 4-position fits better into rnNOS.

In the hnNOS structure, the central phenyl ring of 24 flips 180° relative to the orientation seen in mNOS (data not shown). The aminomethyl moiety interacts with Asn574 and the ethoxyl group still can reach Met341 for contact (data not shown). It might be the polar nature of His342 that pushes the ethoxyl group away and cause the central phenyl ring to flip. The binding mode of 24 in heNOS is almost identical to that observed in mnNOS (data not shown). The better nonbonded contacts between the ethoxyl moiety of 24 and the bulky Phe105 side chain makes the inhibitor more ordered in structure and leads to rather low n/e selectivity (164-fold).

Discussion of the small-4-alkoxy-3-aminomethyl analogues (25-28) is provided in the Supporting Information.

A further improvement for mNOS inhibition was observed by the addition of a small cycloalkyl group (28 and 29). The addition of a cyclobutyl tail moiety allows 28 to form van der Waals interactions in the Met336-Leu337-Tyr706 pocket ((data not shown)), resulting in good potency with rnNOS ($K_i$ (mnNOS)=49 nM). The slightly less bulky cyclopropane analogue 29 was found to have even greater rnNOS potency [$K_i$ (rnNOS)=39 nM], making it the most potent rnNOS inhibitor in the entire series. The X-ray crystal structure of 29 bound to rnNOS reveals that the tail cyclobutane ring fits nicely into the hydrophobic pocket surrounded by Met336, Leu337, and Tyr706 pocket, with the side chain of Tyr706 occupying two alternate conformations (data not shown). Propionate D is pushed by 29 into the downward conformation. However, the orientation of the aminomethyl group shown two alternate directions that form H-bonds with either the $H_4B$ site water or the side chain of Arg481 via water bridging (data not shown). Compound 29 has a nearly 2-fold increase in m/miRNOS selectivity compared to 12 (29, rn/miNOS=841; 12, rn/miNOS=441).

Not only does 29 have high inhibition potency against rnNOS, but it also maintains equally high potency against hnNOS, making it a potent dual rnNOS and hnNOS inhibitor. Similar to the binding mode found in the rnNOS-29 structure, the central phenyl ring of 29 bound to hnNOS presses into heme propionate D. The polar nature of His342 forces the tail cyclopropyl group to move away from the imidazole side chain, making contacts with Met341 instead. The binding conformation of the tail cyclopropyl group closely overlaps with the tail cyclobutyl group of 28 in the hnNOS-28 structure, suggesting the placement of the aminomethyl substituent gives rise to the difference in hnNOS activity between 28 and 29. In hnNOS-29, the density for the aminomethyl group is weak in one chain but visible in the other, which indicates that the central phenyl ring is flipped compared to that seen in hnNOS-28 (data not shown), so the aminomethyl group of 29 points to water near Gln483, which is very similar to the binding conformation of the aminomethyl moiety of 12 bound to hnNOS. The positive ammonium group of 29 faces a water-filled pocket noted above for 12 that is influenced by the negative charge of Asp602. In heNOS, again the bulky Phe105 pushes the cyclopropyl group toward heme propionate A, allowing the aminomethyl moiety to make H-bonds with both the propionate and $H_4B$. The aminomethyl group would not point to the water-filled pocket because there is no negatively charged residue lining the pocket in heNOS. Rather, Asn366 is part of this pocket and is very likely the origin of the 457-fold hn/heNOS selectivity for this compound.

4-Phenyloxymethylaryl Analogues 30-37. Thus far, it appears that considerably larger alkoxyl substituents can be accommodated at the 4-position. Aryl substituents are also tolerated; for example, compound 30, with its bulky 3-fluorobenzyl group to the 4-position, is only slightly less potent than 24, although it is considerably less potent than an aminopyridine-pyrrolidine compound (18 nM) after which it is modeled.[25] A similar trend is observed with the benzonitrile ring of 31; previously, 4-cyanoaryl compounds had good hnNOS activity, but lower hn/heNOS selectivity (generally around 30-fold), but in this phenylquinoline scaffold, the hn/heNOS selectivity is higher with the 4-cyanoaryl group present. However, the hn/heNOS selectivity of 31 remains inferior to leads 5, 12, and 24 as a result of increased binding to heNOS (8300 nM). The unusual binding behavior of 31 is discussed in the Supporting Information.

Given the low hn/heNOS selectivity for 31, as well as the disfavored binding to the human nNOS active site, we decided to reduce the overall length of the inhibitors to better fit into the hnNOS active site, while maintaining H-bond accepting capability in the tail ring. The 2- and 3-pyridinylmethyl ether groups of 32 and 33, respectively, were introduced to provide synergistic contact with either Leu337 in rnNOS or His342 in hnNOS. Relative to 12, both pyridinyl modifications provide slight improvements in mNOS potency (32, $K_i$=52 nM; 33, $K_i$=44 nM). The crystal structure mNOS-32 with compound 33 overlaid shows nearly identical binding positions for the aminoquinoline and tail pyridine, with the pyridinyl nitrogen facing away from Leu337 in both cases (to allow hydrophobic interactions) (data not shown). The difference lies in the orientation of the central phenyl ring. As a result, the central-ring aminomethyl group of 33 displaces the $H_4B$ site water, whereas this moiety points away from the existing water in 32.

In the hnNOS-32 structure, the overall binding remains largely the same, although the orientation of the middle phenyl ring is different in the two nNOS cases (data not shown). Here, the ring does not press sufficiently against heme propionate D so that the latter is not distorted as seen in the mNOS-32 structure. The differences might be the result of the Leu337 (rat) and His342 (human) variation, where the bulkier His342 side chain in human nNOS pushes the tail pyridine of 32 away so that the central phenyl does not make such close contacts with the heme propionate D. Because of the 2-position of the pyridine nitrogen atom, a H-bond with the His342 side chain is not possible. Additionally, the position of the aminomethyl group on the phenyl ring has some uncertainty, although some weak electron densities support a likely interaction with Asn574. These deleterious interactions lead to a decreased binding affinity of 32 to hnNOS ($K_i$=76 nM). However, by virtue of substantially diminished binding potency towards miNOS and heNOS, the rn/miNOS and hn/heNOS selectivities of 32 remain quite high (rn/miNOS=879, hn/heNOS=312).

Compound 32 is unique in that previously reported aminoquinolines substituted with pyridines[3] generally had only 10-20-fold n/eNOS selectivity. However, 32 exhibits fairly good hn/heNOS selectivity (312-fold). The main difference is that in the heNOS-32 crystal structure the orientation of the central phenyl ring is perpendicular to the aminoquinoline ring rather than parallel as in hnNOS-32 (data not shown). As a result, the amino group of 32 in heNOS is about 2 Å farther from heme propionate D than it is in hnNOS-32. In addition, the amino group in hnNOS-32 H-bonds with Asn574. These interactions are possible reasons for the good hn/heNOS selectivity.

The 3-pyridylmethyl ether of 33 moderately increases hnNOS potency ($K_i$=45 nM for 33 vs 60 nM for 12). This is not the first instance where the 3-pyridyl moiety has improved binding to both hnNOS, 26 although it is the first example where such a compound has equal potency for both the rat and human enzymes. The hnNOS-33 X-ray structure shows good density for the aminoquinoline and central phenyl rings (data not shown). The tail pyridine portion show signs of disorder but, a potential H-bond between the pyridine and His342 is more feasible for 33 than for 32. In the mNOS-33 structure, however, the hydrophobic portion of the pyridine reach the nonpolar residues Leu337 and Met336, suggesting that the pyridine can be either a hydrophobic or a H-bonding moiety depending on to which nNOS isoform it is bound (data not shown). The aminomethyl moiety of 33 still interacts with Asn574 of hnNOS (data not shown), while in rnNOS-33, it makes an electrostatic interaction with heme propionate A (data not shown). Both interactions are favorable, and the results taken together may suggest a reason for equal potency against rat and human enzymes.

In heNOS-33 the aminomethyl moiety is able to H-bond with heme propionate (data not shown), rather than pointing out toward Gln247 as in the case of 32 (data not shown). How could a simple difference in the pyridinyl nitrogen atom position make such a large difference? The pyridine ring nitrogen atom of 33 can make an extra H-bond with a water molecule next to the $H_4B$, which pulls the inhibitor closer to heme propionate A and results in better interactions. This may explain the 3-fold improvement in binding affinity of 33 (7700 nM) versus 32 (23,700 nM) toward heNOS, which leads to poorer n/eNOS selectivity for 33 (172-fold).

The incorporation of heterocyclic H-bond acceptors leads to favorable increases in both potency and selectivity. Utilizing heterocyclic tail moieties with the dual ability to form hydrophobic interactions with Leu337 in rnNOS, while also forming H-bonding interactions with isoform-specific His342 in hnNOS, may be advantageous for future in vivo studies (where activity in rats is necessary). Considering the importance of the heterocycle, we also sought to exchange the bulkier pyridine for smaller heterocycles (34-37). These compounds all demonstrated high potencies against rnNOS, with $K_i$ values all below 60 nM.

The use of isoxazole (34) resulted in lost activity against hnNOS. However, 4-(methyloxy)-1,3-thiazole (35) resulted in a $K_i$ of 31 nM against hnNOS, making 35 the most potent hnNOS inhibitor in the entire series. Comparing the X-ray crystal structures of mNOS-35 and hnNOS-35 reveals a common binding orientation of the aminoquinoline ring but with differences in the central phenyl ring resulting from different interactions between the thiazole and the enzyme (data not shown). In the mnNOS structure, the thiazole ring is positioned near Leu337 with its carbon atom making the closest contact. In hnNOS-35, the thiazole is near His342 with its S atom facing toward His342 and its N atom H-bonding with a water molecule. The bulkier His342 in hnNOS pushes 35 slightly farther away from the heme than its position in rnNOS. Therefore, the aminomethyl moiety on the central phenyl ring in hnNOS H-bonds with Asn574, whereas the same moiety points toward Gln478 in mNOS, and the phenyl ring flips almost 180°. Unfortunately, single digit micromolar inhibitory activity of 35 against miNOS and heNOS results in low m/mi and hn/heNOS selectivities relative to 32.

The use of oxazole (36) results in a slight loss in hnNOS potency ($K_i$=63 nM). However, reduced inhibitory activity against miNOS and heNOS led to excellent selectivities (m/miNOS=382, hn/heNOS=433).

Human iNOS Inhibition Study. Recently, we successfully expressed and purified human iNOS protein that showed robust activity. Human iNOS (hiNOS) assay data were collected for eight compounds, including the three simple aminomethyl compounds 7, 10, and 12, as well as a sampling of the more potent compounds from the latter series (29, 32, 36, and 37) to determine the SAR for the human system. $K_i$ values obtained from rat and human nNOS, as well as murine and human iNOS, were used to approximate the cross-species selectivity between lower-(rn/mi) and higher-order species (hn/hi) (vide infra). The major difference between murine and human iNOS that might affect inhibitor binding is that Asn115 in miNOS is Thr121 in hiNOS. The tail part of many inhibitors might reach the site based on observations in the available nNOS and eNOS structures. Without an iNOS-inhibitor structure, we can only speculate on potential interactions by superimposing the iNOS structures onto the known nNOS-inhibitor structures.

The general inhibition trends in Table 2 are more or less consistent (<2-fold) between murine and human iNOS, with only 7 and 33 as the principal exceptions. Compound 7 is a compact inhibitor that would make only weak contacts with the Asn115/Thr121 (miNOS/hiNOS) site. The twofold difference in binding affinity might result from the variation in a water-mediated H-bonding network or another unknown reason. Contrarily, overlaying the structure of miNOS or hiNOS on hnNOS-33 reveals that the pyridine nitrogen atom of 33 is capable of making a direct H-bond with either Asn115 or Thr121 (data not shown). The three-fold weaker binding affinity to hiNOS might indicate a weaker interaction with Thr121 in hiNOS (than with Asn115 in miNOS). In the same overlay, another variation site, Ser256/Ala262 (miNOS/hiNOS), is more than 5.0 Å from the potential position of the aminomethyl moiety of 33, likely too far away to influence inhibitor binding.

TABLE 2

Inhibition of Rat and Human nNOS Compared to Murine and Human iNOS by Selected Compounds[a]

| | $K_i$ (μM) | | | | Selectivity | |
|---|---|---|---|---|---|---|
| compd | rnNOS | hnNOS | miNOS | hiNOS | rn/mi | hn/hi |
| 7 | 0.045 | 0.088 | 16.3 | 6.94 | 362 | 79 |
| 10 | 0.119 | 0.151 | 2.86 | 3.55 | 24 | 24 |
| 12 | 0.055 | 0.060 | 24.2 | 29.9 | 441 | 498 |
| 29 | 0.039 | 0.046 | 32.8 | 21.1 | 841 | 459 |
| 32 | 0.052 | 0.076 | 45.7 | 43.9 | 879 | 578 |
| 33 | 0.044 | 0.045 | 8.18 | 29.4 | 186 | 653 |
| 36 | 0.043 | 0.063 | 16.4 | 24.6 | 382 | 390 |
| 37 | 0.053 | 0.046 | 21.0 | 34.8 | 397 | 757 |

[a]Compounds 7, 10, 12, 29, 32, 33, 36 and 37 were assayed for in vitro inhibition against purified human iNOS (hiNOS) using known literature methods, and $K_i$ values were calculated directly from $IC_{50}$ values using the Cheng-Prusoff equation. $IC_{50}$ values are the average of at least two replicates from 6-9 data points, all experimental standard error values (for the log $IC_{50}$) are less than ±0.10. $K_i$ values for isoforms: rat nNOS (rnNOS), human nNOS (hnNOS), and murine iNOS (miNOS) were included for comparison. Selectivity values are ratios of respective $K_i$ values.

Directed Mutagenesis Supports Water-Mediated Interaction of Inhibitors with Asp597. Previous studies indicated that Asp597 in mNOS electrostatically stabilizes cationic inhibitors and can account for much of the selectivity for nNOS over eNOW (as this residue is Asn in heNOS). A second difference, Met336 in rnNOS (Val in heNOS), can provide better nonpolar contacts with inhibitors and impart selectivity. To test the importance of these differences further, we determined the $K_i$ values for certain compounds against various mnNOS mutants (Table 3).

TABLE 3

Inhibition Data for Wild-Type and Mutant NOS Enzymes by Selected Compound (7, 10, 12, 29, 32, and 36)[a]

| | $K_i$ (μM) | | | | Selectivity | |
|---|---|---|---|---|---|---|
| compd | WT-rnNOS | heNOS | D597N rnNos | M336V/D597N rnNOS | WT/SM | WT/DM |
| 7 | 0.045 | 18.7 | 0.273 | 0.215 | 6 | 5 |
| 10 | 0.119 | 41.9 | 2.11 | 1.57 | 18 | 13 |
| 12 | 0.055 | 52.6 | 0.416 | 1.60 | 8 | 29 |
| 29 | 0.039 | 21.0 | 0.246 | 0.189 | 6 | 5 |
| 32 | 0.052 | 23.7 | 0.384 | 0.159 | 7 | 3 |
| 36 | 0.043 | 27.3 | 0.575 | 0.114 | 13 | 3 |

[a]The compounds were assayed for in vitro inhibition against purified NOS isoforms: rat nNOS (rnNOS), human eNOS (heNOS), as well as single mutant (SM) (D597N) and double mutant (DM) (M336V/D597N) of rat nNOS using known literature methods, and $K_i$ values were calculated directly from $IC_{50}$ values using the Cheng-Prusoff equation. $IC_{50}$ values are the average of at least two replicates from 6-9 data points; all experimental standard error values (for the log $IC_{50}$) are less than ±0.10. Selectivity values are ratios of respective $K_i$ values.

All tested compounds exhibited decreased potency against the single-mutant enzyme (D597N) (perhaps, as expected), but against the double mutant, all compounds had potency comparable to the single mutant (except for 12, where it was greatly reduced). Compound 36 actually displayed 5-fold increased potency against the double mutant (versus the single mutant). The rnNOS-36 structure shows that the tail end of the inhibitor contacts Met336 and Leu337. These two residues are Val104 and Phe105 in heNOS, and contacts made with the tail end of the inhibitor may involve more than the Met/Val difference. It is possible that the local environment near the Val336 and Leu337 residues in the M336V/D597N double mutant enables better contacts with the tail end of the inhibitor than the same area in the D597N single mutant does, thus improving the potency against the double mutant versus the single mutant. This trend is reflected in the behaviors of 29, 32, and 36, all of which have a long tail moiety that fits in this region of the enzyme. On the other hand, more compact inhibitors might be less sensitive to the Met/Val mutation site.

We conclude by focusing on 12, since this inhibitor exhibits the best hn/heNOS selectivity (877-fold). The D597N mutant decreases potency 8-fold, which further drops to 29-fold against the M336V/D597N mutant, even though this inhibitor does not appear to make contact with the Met/Val site. It is perhaps more instructive to consider the change in $\Delta G_{bind}$ obtained from the $K_i$ values, where $\Delta G_{bind}$=−RT ln $K_i$. $\Delta G_{bind}$ for WT hnNOS, WT heNOS, and the hnNOS D597N mutant are −9.9, −4.5, and −7.3 kcal/mol, respectively. Thus, the Asp/Asn difference accounts for about half of $\Delta\Delta G_{bind}$ between heNOS and hnNOS, leaving about −2.6 kcal/mol of binding affinity unexplained. This underscores the limitation of quantitatively explaining selectivity (against isoforms or mutants) by a few simple amino acid differences and a comparison of static X-ray structures. There are clear examples of differences in active-site dynamics and the ability of even conserved side chains to adjust to inhibitor binding that could also contribute to selectivity (anchored plasticity) in cases like this.[27]

Off-Target Profiling. Four structurally diverse compounds from this series (12, 29, 32, and 33) were screened by the National Institute of Mental Health's Psychoactive Drug Screening Program (PDSP, Table 4). In this assay,[28] compounds were screened against a panel of 45 pharmacologically relevant CNS targets and receptors using a radioligand displacement assay. Initially, the assay used a primary high dose (10 μM) and then a secondary $K_i$ determination was performed for compounds showing >50% binding in the primary assay. We classify off-target binding using the following rubric: concerning ($K_i$<100 nM, or <~2×nNOS $K_i$ value), moderate (100-300 nM, or ~2-5×nNOS $K_i$ value), weak (>300 M, or >~5×nNOS $K_i$ value, typically ~1 μM), and insignificant (<50% at 10 μM). The off-target profiles of previous aminoquinolines 1 and 4 have been included for comparison. Although not as effective as 4, a slight decrease in the fraction of concerning or moderate hits for 32 is observed (11/45 for 32 compared to 15/45 for 1), while this fraction decreases further to 8/45 for 33. Unfortunately, most of the flagged targets for 32 and 33 are serotonin receptors, suggesting that the heteroaryl-alkyl tails may resemble a GPCR-ligand-like pharmacophore.[29] Conversely, the off-target profiles for 12 and 29 reveal the cleanest CNS counter screening observed for 2-aminoquinolines to date, flagging only the H2 and H3 receptors as concerning for 12 and 29, respectively, which is unsurprising as these receptors are known to bind cationic amidine groups (e.g., ranitidine), while 29 only flagged an additional 4/45 targets for moderate binding.[30] For 12, 21/45 targets were classified as weak (27/45 for 29), while 23/45 (12) and 13/45 (29) were classified as insignificant. These results indicate that reducing the tail group's size (as in 29) or eliminating it completely (as in 12) are both effective strategies to reduce off-target CNS binding, which may translate to improved safety in vivo.

TABLE 4

]PDSP Binding Summary for Selected Compounds[a]

| compd | concerning | moderate | weak | insignificant | total |
|---|---|---|---|---|---|
| 1 | 8 | 7 | 22 | 8 | 45 |
| 4 | 3 | 6 | 17 | 22 | 45 |
| 12 | 1 | 0 | 21 | 23 | 45 |
| 29 | 1 | 4 | 27 | 13 | 45 |
| 32 | 4 | 7 | 22 | 12 | 45 |
| 33 | 3 | 5 | 17 | 20 | 45 |

[a]Off-target binding is classified into four categories: concerning ($K_i$ < 100 nM, or < ~2 × nNOS $K_i$ value), moderate (100-300 nM, or ~2-5 × nNOS $K_i$value), weak (>300 nM, or > ~5 × nNOS$K_i$ value, typically ~1 μM), and insignificant (<50% bound at 10 μM), for a total of 45 receptors as assayed by the PDSP's "comprehensive screen" (see ref 28). See Supporting Information, Table S1 for PDSP secondary binding affinities ($K_i$).

Membrane Permeability and Microsome Stability. As our ultimate goal is to utilize these compounds as CNS drugs, membrane permeability for compounds 7, 12, 29, 33, and 37 was determined using the parallel artificial membrane permeability for the blood-brain barrier (PAMPA-BBB) assay. In this assay, an artificial membrane containing BBB phospholipids is used to assess permeability. A compound is predicted to have good BBB penetration and is classified as a "CNS (+)" molecule if its effective permeability (Pe) in this assay is larger than $4.0\times10^{-6}$ cm $s^{-1}$.[31-34] Additionally, the web tool SwissADME was used to make in silico passive-BBB penetrability predictions based on their validated BOILED-Egg (Brain Or Intestinal EstimateD permeation) predictive model.[35,36] Table 5 contains $P_e$ values of three commercial drug standards and selected nNOS inhibitors 7, 12, 29, 33, and 37. All of the selected nNOS inhibitors are predicted "CNS (+)" with $P_e$ values of up to $15.5\times10^{-6}$ cm $s^{-1}$. Compounds 33 and 37 display the lowest permeability among the selected compounds ($P_e$=$8.09\pm0.67\times10^{-6}$ cm $s^{-1}$ and $7.04\pm2.43\times10^{-6}$ cm $s^{-1}$, respectively), indicating that the presence of the heterocyclic tail portion may reduce the permeability of these compounds. However, while the Pe values for 33 and 37 were high enough to score as "CNS (+)", the BOILED-Egg permeant model predicted that they would not have BBB penetration because of their higher tPSA values of 87.05 and 115.29 Å2, respectively, although these two compounds, along with all of the tested compounds, have predicted log D and log P values that are favorable for BBB penetration. Cyclopropyl compound 29, which lacks polar heterocycles of 33 and 37, has a lower tPSA (74.16 $Å^2$), a twofold higher Pe, and is predicted to be BBB (+). Eliminating the substitution at the 4-position gave mixed results. Although not as high as 29, compound 7 maintained a high $P_e$ value ($11.3\pm1.64\times10^{-6}$ cm $s^{-1}$) relative to 33 and 37, although compound 12 was found to have the highest Pe out of all compounds assayed. Additional cellular pharmacokinetic assays are in progress.

TABLE 5

Effective Permeability ($P_e$) of Five Commercial Drugs and nNOS Inhibitors in the PAMPA-BBB Assay[a]

| Compd | log D[b] | log P[b] | TPSA ($Å^2$)[c] | reported $P_e$ ($10^{-6}$ cm $s^{-1}$)[d] | determined $P_e$ ($10^{-6}$ cm $s^{-1}$)[e] | BBB permeant predition[c] | prediction |
|---|---|---|---|---|---|---|---|
| verapamil | 2.29 | 4.55 | 63.95 | 16 | 21.3 ± 1.5[f]<br>18.5 ± 1.9 | BBB (+) | CNS (+) |
| chlorpromazine | 2.76 | 4.56 | 31.78 | 6.5 | 8.04 ± 0.41[f]<br>8.90 ± 0.68 | BBB (+) | CNS (+) |
| dopamine | −1.50 | 0.03 | 66.48 | 0.2 | 0.12 ± 0.41[f]<br>0.125 ± 0.14 | BBB (−) | CNS (−) |
| 7 | 1.36 | 3.32 | 64.93 | | 11.3 ± 1.64 | BBB (+) | CNS (+) |
| 12 | 1.27 | 3.18 | 64.93 | | 15.5 ± 2.32 | BBB (+) | CNS (+) |
| 29 | 2.37 | 3.78 | 74.16 | | 14.6 ± 0.97 | BBB (+) | CNS (+) |
| 33 | 2.13 | 3.53 | 87.05 | | 8.09 ± 0.67 | BBB (−) | CNS (+) |
| 37 | 1.94 | 3.35 | 115.29 | | 7.04 ± 2.43 | BBB (−) | CNS (+) |

[a]All assays were performed over 17 h at a concentration of 200 μM; see the Experimental Section for details.
[b]log D (pH = 7.4) and log P values of the free-base species were predicted using ChemAxon software.
[c]TPSA calculations and BBB permeation were predicted using the free web tool SwissADME.
[d]Effective permeability values from the literature.[32]
[e]Effective permeability values obtained in-house.
[f]Experimental $P_e$ values reported previously by Do et al.[37]

Figure 4A:
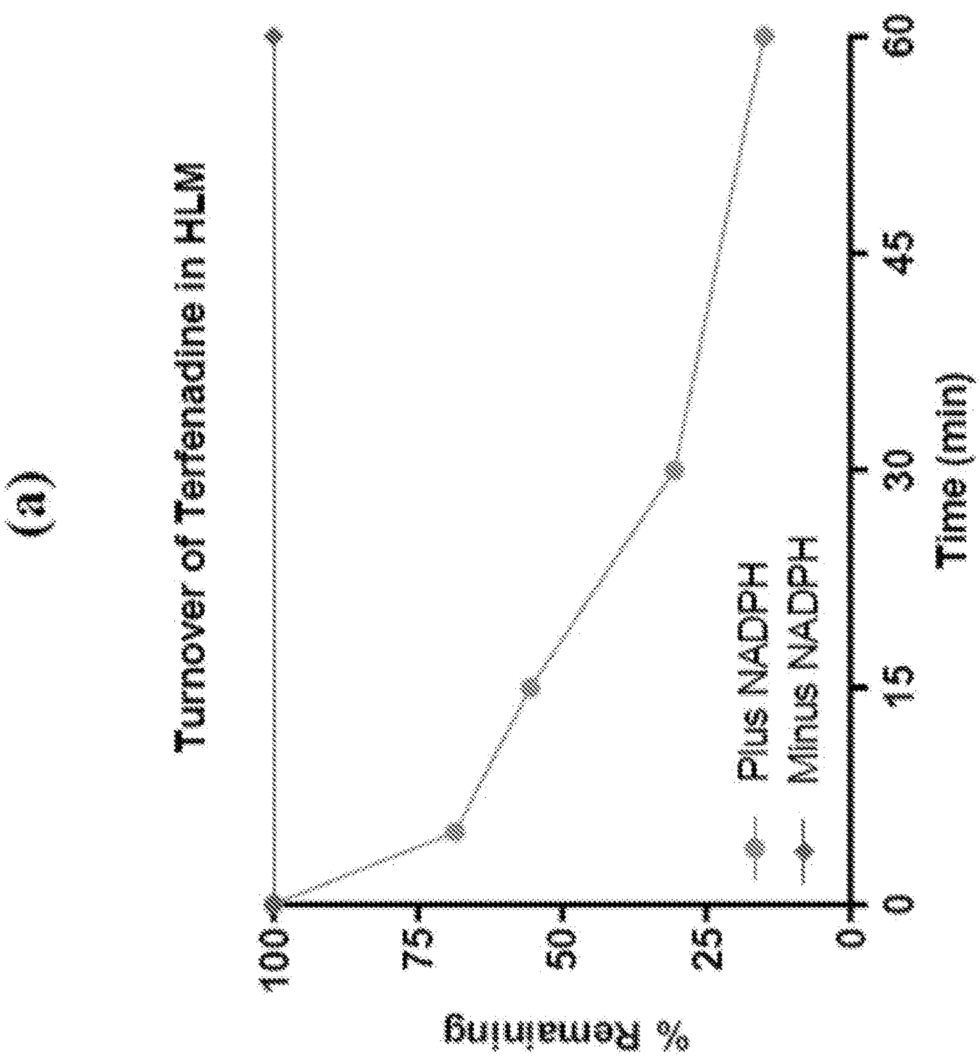
FIG. 4*a*. Time-dependent loss of terfenadine in human liver microsome (HLM).
Figure 4B:
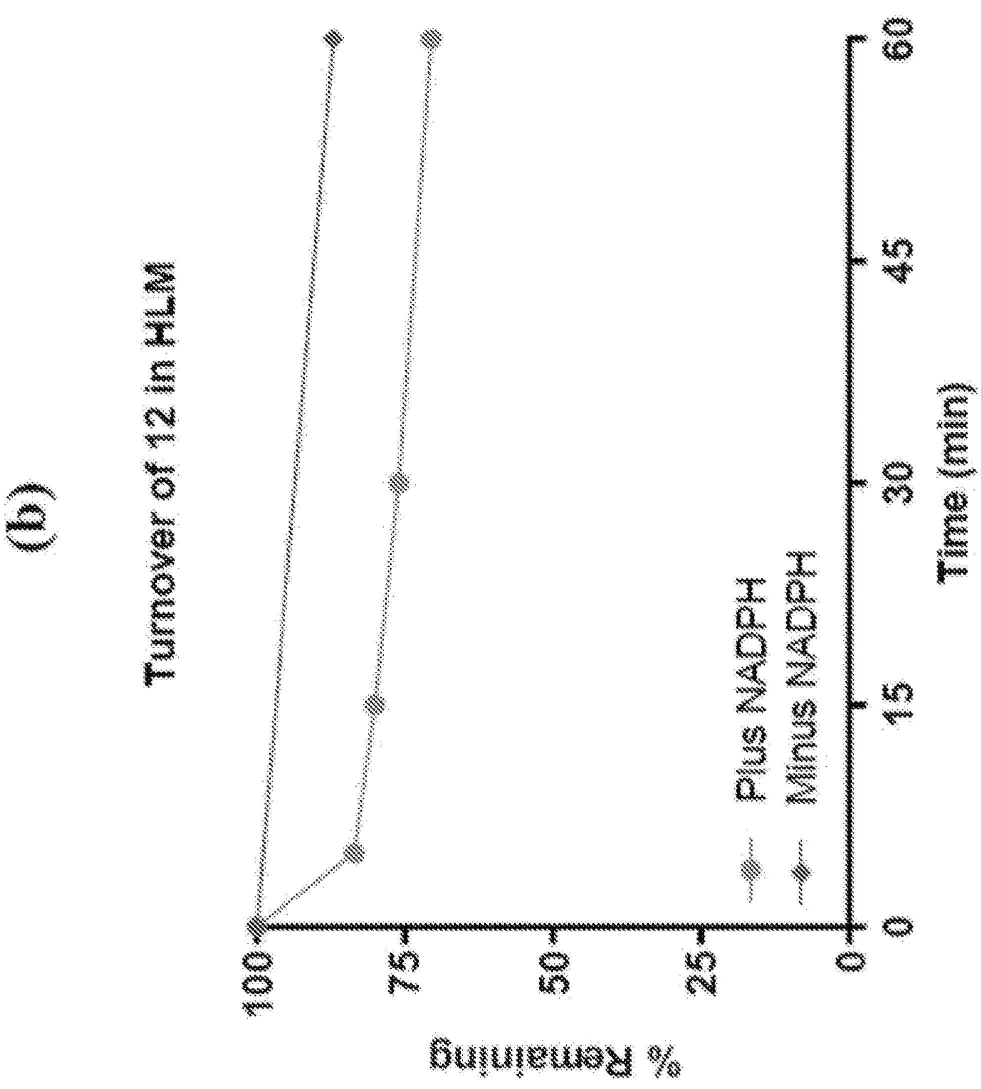
FIG. 4*b*. Time-dependent loss of compound 12 in human liver microsome (HLM).

Additionally, stability in the presence of human liver microsomes (HLMs) was determined for 12 and positive control terfenadine. The results of this study (Table 6) show that 12 displays high stability relative to the positive control, as indicated by a half-life ($t_{1/2}$)>60 min. However, 12 did show a sign of degradation in buffer control samples (FIG. 4).

TABLE 6

Metabolic Stability of 12 and Positive Control in Human Liver Microsome[a]

| compd | % remaining at 60 min (—NADPH ) | % remaining at 60 min (buffer) | $t_{1/2}$ (min)[b] | $CL_{int}$ (mL/(min kg)[c] |
|---|---|---|---|---|
| 12 | 87 | 67 | >60 | 8 |
| terfenadine[d] | 101 | 100 | 23 | 108 |

[a]All assays were performed in 50 mM Kphos buffer (pH 7.4) containing HLM (0.714 mg/mL) over 60 min at 1.428 μM drug concentration. Parent compound peak disappearance was monitored by liquid chromatography-mass spectrometry (LC-MS)/MS; see Experimental Section for details.
[b]$t_{1/2}$: half-life.
[c]$CL_{int}$: in vitro intrinsic clearance.
[d]Positive control.

Conclusions

In summary, we prepared a series of novel 7-phenyl-2-aminoquinolines possessing tail amines designed to target nNOS-specific aspartate residues Asp597/Asp602 (mNOS/hnNOS) and thereby result in higher n/eNOS selectivity. Initially, screening compounds 5-13 revealed a preference for meta-substituted benzylamines, such as 12, which shows excellent potency and outstanding selectivity for nNOS over the other isozymes. A number of modifications to 12 were made, which included reducing or constraining amino group flexibility, substituting the 4-position of the phenyl ring, and using a 1,3,5-tri-substituted phenyl core. While the amine cannot be constrained effectively and 1,3,5-tri-substitutions clash deleteriously with heme propionates in the enzyme, some 4-position additions enhance potency and maintain high isoform selectivity via favorable interactions with isoform-specific residues on the far end of the substrate access channel, namely, Leu337/His342 (rnNOS/hnNOS). Crystal structures indicate that these compounds act as competitive arginine mimics, where the aminoquinoline forms hydrogen bonds with the active-site glutamate residue, but also that substitutions at the 4-position can reduce phenyl ring rotation to favor interactions with the Asp (Asp597/Asp602)/H4B/propionate A site over the propionate D site. Mutagenesis studies confirmed the influence of the Asp site on inhibitor potency, making this class of aminoquinolines the first with the ability to target this site in nNOS, although preference for this site varies from compound to compound. Finally, with these inhibitors, the hn/heNOS selectivity derives more from a weakening of affinity to heNOS rather than from an increase in affinity for hnNOS; inhibitors more complex than 12 tend to be less selective because of an increased affinity for heNOS. Apparently, more complex substituents provide additional contacts that improve binding to heNOS relative to hnNOS. On the basis of both their good potency and selectivity, clean CNS counterscreening (PDSP) profiles, and excellent permeability in our PAMPA-BBB assay, the most promising compounds, 12 and 29, are being advanced into preclinical studies.

Experimental Section

General Procedures. Anhydrous solvents (THF, $CH_2Cl_2$, MeOH, $Et_3N$, and DMF) were distilled prior to use. All other solvents, reactants, and reagents were purchased from commercial vendors and were used without further purification. Methanolic HCl (3 M, for ammonium hydrochloride salt formation and Boc-deprotection) was prepared fresh by the reaction of acetyl chloride and anhydrous MeOH at 0° C. Melting points were determined in capillary tubes using a Buchi melting point B-540 apparatus and are uncorrected. $^1$H-NMR spectra were recorded at 500 MHz, using a Bruker Avance III 500 (direct cryoprobe), and $^{13}$C-NMR spectra were obtained at 126 MHz using the same instrument. High-resolution mass spectral data were obtained at the Integrated Molecular Structure Education and Research Center (IMSERC, Northwestern University) on an Agilent 6210A TOF mass spectrometer in positive ion mode coupled to an Agilent 1200 series HPLC system. Data were processed using MassHunter software version B.04.00. Flash column chromatography was performed using an Agilent 971-FP automated flash purification system with a Varian column station and SiliCycle cartridges (12-80 g, both normal and High Performance). Analytical HPLC was performed using an Agilent Infinity 1260 HPLC system with injection volumes of 5-10 μL. A Phenomenex Luna 5 μm C-8 (2) 100 Å column, 50×4.60 mm, was used for all HPLC experiments, using a 10-min gradient of 95% $H_2O$/5% acetonitrile +0.05% TFA to 95% acetonitrile/5% $H_2O$+ 0.05% TFA, at 1.5 mL/min. The purity of all final target compounds was found to be ≥95% by HPLC. Analytical thin-layer chromatography was performed on Silicycle extra-hard 250 μm TLC plates. Compounds were visualized with short-wavelength UV light, and with ninhydrin and CAM stains, where appropriate. The preparation of quinoline precursors and assembly of final compounds is described below, while the preparation of other precursors is discussed in the Supporting Information in Example 2. Compounds 38,[8] 41,[38] 43,[39] 45,[40] 52,[41] 53,[42] 56,[43] 57,[8] 66,[44] 69,[45] 70,[15] 86,[46] 89,[47] 90,[40] and 96[48] were prepared by literature procedures or are known, and their spectral or analytical data are identical to those reported.

General Procedure 1: Suzuki Coupling between 39 and Aryl Halides. Compound 39 (1 eq.), the requisite aryl halide (1-1.2 eq.), $Pd(dppf)Cl_2$ (5 mol %) and $NaHCO_3$ (3.5-4 eq.) were combined in dimethoxyethane/$H_2O$ (3:1, 4 mL solvent per 0.25 mmol 39 is sufficient) in a 20 mL sealable microwave vial. The mixture was briefly sparged with argon, sealed, and heated to 120° C. under microwave irradiation with stirring (720 rpm) for 20-25 minutes. After cooling, the mixture was partitioned between EtOAc and $H_2O$ (10 mL each), the layers were separated, and the aqueous layer was extracted with EtOAc (3×30 mL), and the organic layer was washed with 5% aq. NaCl (2×50 mL) and sat. aq. NaCl (50 mL), dried over anhydrous sodium sulfate and concentrated. The crude residue was purified as listed below under subheadings for individual compounds.

General Procedure 2: Deprotection of Aminoquinolines. The protected intermediate was immediately diluted with MeOH (9-10 mL/0.2 mmol of protected quinoline), and $K_2CO_3$ (2 eq.) was added. The mixture was heated at reflux for 2-2.5 h, cooled, and concentrated, and the residue was partitioned between EtOAc (10 mL) and $H_2O$/sat. aq. NaCl (1:1, 10 mL). The layers were separated, the aqueous phase was extracted with EtOAc (3×20 mL), and the organic layers were combined, washed with sat. aq. NaCl (20 mL), dried over anhydrous sodium sulfate and concentrated. Purification, if necessary, is described below under subheadings for individual compounds. The resulting free 2-aminoquinoline was dissolved in MeOH or ether/MeOH (10-15 mL), filtered to remove particulate matter, and treated with methanolic HCl (~3 M, ~1.5-2 mL). The mixture was stirred overnight at r.t. and workup (as described below) afforded the deprotected compounds as hydrochloride salts.

7-(4-(2-Aminoethyl)phenyl)-4-methylquinolin-2-amine Dihydrochloride (5). Compounds 39 (0.050 g, 0.163 mmol) and 41 (0.050 g, 0.167 mmol) were coupled using General Procedure 1. Purification by flash column chromatography, eluting with a gradient of 5% EtOAc in $CH_2Cl_2$ to 30% EtOAc in $CH_2Cl_2$, afforded protected phenylquinoline 42 as a white solid (0.052 g, 76%). This compound was immediately deprotected using General Procedure 2. After workup, the free aminoquinoline was diluted in ether/MeOH (1:1, 20 mL), heated gently to affect solution, filtered, and cooled. After treatment with methanolic HCl, 5 was obtained as a cream-colored solid (0.037 g, 86% from 42) after triturating with ether and drying in vacuo: $^1H$-NMR (500 MHz; DMSO-$d_6$): δ 14.09 (s, 1H), 8.07-7.94 (m, 5H), 7.81 (dd, J=8.5, 1.6 Hz, 1H), 7.75 (d, J=8.2 Hz, 2H), 7.46 (d, J=8.2 Hz, 2H), 6.93 (s, 1H), 3.12-3.08 (m, 2H), 2.96 (t, J=7.8 Hz, 2H), 2.65 (s, 3H); the aminoquinoline-NH protons are mostly broadened into the baseline at 8.1 and 8.9 ppm; $^{13}C$-NMR (126 MHz; DMSO-$d_6$): δ 154.3, 152.6, 143.8, 138.6, 137.4, 136.9, 130.2 (2 C), 127.8 (2 C), 126.7, 123.9, 120.9, 115.4, 112.9, 33.1, 19.4; one of the aliphatic carbon signals is obscured by the solvent peak; HRMS calcd for $C_{18}H_{20}N_3^+$: 278.1652; found, 278.1661.

4-Methyl-7-(4-(2-(methylamino)ethyl)phenyl) quinolin-2-amine Dihydrochloride (6). Compounds 39 (0.075 g, 0.245 mmol) and 44 (0.079 g, 0.251 mmol) were coupled using General Procedure 1. Purification by flash column chromatography, eluting with a gradient of 5% EtOAc in $CH_2Cl_2$ to 30% EtOAc in $CH_2Cl_2$, afforded protected phenylquinoline 59 as a yellow foam (0.070 g, 70%). This compound was immediately deprotected using General Procedure 2. After workup, the free aminoquinoline was passed through a short $SiO_2$ plug, eluting with 1% MeOH in EtOAc. The filtrate was concentrated, washed with hexanes, and diluted in ether/MeOH (8:1, 20 mL). After treatment with methanolic HCl, 6 was obtained as a flocculent cream-colored solid (0.057 g, 76% from 58) after filtering, precipitating from MeOH (1 mL) with ether (5 mL) triturating with ether, and drying in vacuo: mp 307-308.3° C. (dec). $^1H$-NMR (500 MHz; DMSO-$d_6$): δ 14.09 (s, 1H), 8.86-8.85 (m, 2H), 8.06 (d, J=8.5 Hz, 1H), 7.94 (d, J=1.7 Hz, 1H), 7.82 (dd, J=8.5, 1.7 Hz, 1H), 7.77-7.75 (m, 2H), 7.46 (d, J=8.3 Hz, 2H), 6.93 (d, J=1.0 Hz, 1H), 3.22-3.16 (m, 2H), 3.02 (t, J=8.0 Hz, 2H), 2.66 (d, J=0.9 Hz, 3H), 2.59 (t, J=5.1 Hz, 3H); the aminoquinoline-NH protons are mostly broadened into the baseline at 8.1 and 8.9 ppm; $^{13}C$-NMR (126 MHz; DMSO-$d_6$): δ 154.33, 152.50, 143.75, 138.36, 137.40, 136.98, 130.14 (2 C), 127.79 (2 C), 126.66, 123.84, 120.89, 115.42, 112.93, 49.36, 32.93, 31.57, 19.41; HRMS calcd for $C_{19}H_{22}N_3^+$: 292.1808; found, 292.1822.

7-(4-(Aminomethyl)phenyl)-4-methylquinolin-2-amine Dihydrochloride (7). Compounds 39 (0.075 g, 0.245 mmol) and 45 (0.082 g, 0.245 mmol) were coupled using General Procedure 1. Purification by flash column chromatography, eluting with a gradient of 5% EtOAc in $CH_2Cl_2$ to 40% EtOAc in $CH_2Cl_2$, afforded protected phenylquinoline 59 as a yellow solid (0.062 g, 63%). This compound was immediately deprotected using General Procedure 2. After workup, the free aminoquinoline was precipitated from EtOAc (1 mL) with hexanes (9 mL), triturated with hexanes, and diluted in ether/MeOH (5:1). After treatment with methanolic HCl, 7 was obtained as a cream-colored solid (0.043 g, 84% from 59) after filtering, precipitating twice from hot MeOH (2 mL) with ether (10 mL), washing with ether, and drying in vacuo: mp >300° C. (darkens slowly), >360° C. (melts or decomposes). $^1H$-NMR (500 MHz; DMSO-$d_6$): δ 14.10 (s, 1 H), 9.06 (br s, 1H), 8.43 (s, 3H), 8.30 (br s, 1H), 8.09 (d, J=8.5 Hz, 1H), 7.98 (d, J=1.7 Hz, 1 H), 7.86-7.84 (m, 3H), 7.67 (d, J=8.4 Hz, 2H), 6.95 (d, J=1.0 Hz, 1H), 4.13-4.10 (m, 2H), 2.67 (d, J=0.9 Hz, 3H); $^{13}C$-NMR (126 MHz; DMSO-$d_6$): δ 154.3, 152.6, 143.5, 138.9, 136.7, 135.1, 130.3 (2 C), 127.7 (2 C), 126.7, 124.0, 121.0, 115.5, 113.1, 42.3, 19.4; HRMS calcd for $C_{17}H_{18}N_3^+$: 264.1495; found, 264.1503.

4-Methyl-7-(4-((methylamino)methyl)phenyl) quinolin-2-amine Dihydrochloride (8). Compounds 39 (0.075 g, 0.245 mmol) and 46 (0.085 g, 0.245 mmol) were coupled using General Procedure 1. Purification by flash column chromatography, eluting with a gradient of 5% EtOAc in $CH_2Cl_2$ to 40% EtOAc in $CH_2Cl_2$, afforded protected phenylquinoline 60 as a yellow solid (0.072 g, 70%). This compound was immediately deprotected using General Procedure 2. After workup, the free aminoquinoline was precipitated from EtOAc (1 mL) with hexanes (9 mL). The solid was collected and diluted in ether/MeOH (3:1). After treatment with methanolic HCl, ether (10 mL) was added, and 8 was obtained as a cream-colored solid (0.047 g, 78% from 60) after filtering, precipitating from hot MeOH (2 mL) with ether (10 mL), washing with ether, and drying in vacuo. $^1$H-NMR (500 MHz; DMSO-$d_6$): δ 14.06 (s, 1H), 9.20 (s, 2H), 9.00 (br s, 1H), 8.20 (br s, 1H), 8.08 (d, J=8.5 Hz, 1H), 7.97 (d, J=1.7 Hz, 1H), 7.86-7.82 (m, 2.0 Hz, 3H), 7.70 (d, J=8.3 Hz, 2H), 6.94 (d, J=1.0 Hz, 1H), 4.21-4.19 (m 2 H), 2.66 (d, J=0.9 Hz, 3H), 2.58-2.56 (m, 3H); $^{13}$C-NMR (126 MHz; DMSO-$d_6$): δ 154.3, 152.6, 143.3, 139.4, 136.8, 133.1, 131.3 (2 C), 127.8 (2 C), 126.7, 124.0, 121.1, 115.6, 113.1, 51.2, 32.6, 19.4; HRMS calcd for $C_{18}H_{20}N_3^+$: 278.1652; found, 278.1664.

(S)-7-(4-(2-Aminopropyl)phenyl)-4-methylquinolin-2-amine Dihydrochloride (9). Compounds 39 (0.075 g, 0.245 mmol) and 49 (0.077 g, 0.245 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 61 as a pale-yellow foam (0.092 g, 87%). This compound was immediately deprotected using General Procedure 2. After workup, the free aminoquinoline was washed with 10:1 hexanes/$CH_2Cl_2$ (10 mL). The solid was collected and diluted in ether/MeOH (3:1). After treatment with methanolic HCl, the mixture was concentrated, and the residue was azeotroped with toluene twice. After precipitation of the residue from MeOH (1 mL) with ether (10 mL), 9 was obtained as a tan hygroscopic powder (0.058, 75% from 61) after washing with ether and drying in vacuo: mp >260° C. (darkens slowly), 281-282° C. (dec). $^1$H-NMR (500 MHz; DMSO-$d_6$): δ 14.27 (s, 1H), 9.00 (br s, 1H), 8.20 (br s, 1H), 8.14-8.13 (m, 3H), 8.06 (d, J=8.5 Hz, 1H), 7.96 (d, J=1.5 Hz, 1H), 7.82 (dd, J=8.5, 1.5 Hz, 1H), 7.76 (d, J=8.2 Hz, 2H), 7.45 (d, J=8.2 Hz, 2H), 6.94 (s, 1H), 3.50-3.45 (m, 1H), 3.10 (dd, J=13.4, 5.3 Hz, 1H), 2.78 (dd, J=13.4, 8.8 Hz, 1H), 2.66 (s, 3H), 1.17 (d, J=6.5 Hz, 3H). $^{13}$C-NMR (126 MHz; DMSO-$d_6$): δ 154.3, 152.5, 143.8, 138.1, 137.3, 136.8, 130.7 (2 C), 127.7 (2 C), 126.7, 123.9, 120.8, 115.3, 112.9, 48.4, 19.4, 18.2; one of the aliphatic carbons is obscured by the solvent peak; HRMS calcd for $C_{19}H_{22}N_3^+$: 292.1808; found, 292.1818.

7-(2-(Aminomethyl)phenyl)-4-methylquinolin-2-amine Dihydrochloride (10). Compounds 39 (0.075 g, 0.245 mmol) and 52 (0.070 g, 0.245 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 62 as pale-yellow crystals (0.098 g, 99%). This compound was immediately deprotected using General Procedure 2. After workup, the free aminoquinoline was diluted in ether/MeOH (5:1). After treatment with methanolic HCl, the mixture was concentrated, and 10 was obtained as a white solid (0.070 g, 86% from 62) after precipitating twice from hot MeOH (1 mL) with ether (10 mL), washing with ether, and drying in vacuo: mp 290-291.5° C. $^1$H-NMR (500 MHz; DMSO-$d_6$): δ 14.21 (s, 1H), 9.00 (br s, 1H), 8.42 (s, 3H), 8.30 (br s, 1H), 8.07 (d, J=8.4 Hz, 1H), 7.74 (d, J=7.6 Hz, 1H), 7.67 (s, 1H), 7.59-7.51 (m, 3H), 7.39-7.38 (m, 1H), 6.97 (s, 1H), 3.97 (br d, J=4.0 Hz, 2H), 2.67 (s, 3 H); $^{13}$C-NMR (126 MHz; DMSO-$d_6$): δ 154.4, 143.7, 140.4, 132.0, 130.5, 129.29, 129.18, 129.09, 126.4, 126.0, 120.9, 118.7, 113.3, 19.5; two of the quinoline carbons are not visible due to baseline broadening; one of the aliphatic carbon signals is obscured by the solvent peak; HRMS calcd for $C_{17}H_{18}N_3^+$: 264.1495; found, 264.1503.

7-(2-(2-Aminoethyl)phenyl)-4-methylquinolin-2-amine Dihydrochloride (11). Compounds 39 (0.075 g, 0.245 mmol) and 53 (0.077 g, 0.257 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 63 as pale-yellow crystals (0.093 g, 90%). This compound was immediately deprotected using General Procedure 2. After workup, the free aminoquinoline was sonicated with hexanes, and the solid was collected and diluted in ether/MeOH (2:1). After treatment with methanolic HCl, the mixture was concentrated, and 11 was obtained as an off-white powder (0.064 g, 83% from 63) after precipitating twice from hot MeOH (2 mL) with ether (10 mL), washing with ether, and drying in vacuo: mp >300° C. (darkens slowly), 323-325° C. (dec). $^1$H-NMR (500 MHz; DMSO-$d_6$): δ 14.37 (s, 1H), 8.10 (br s, 1H), 8.10 (br s, 1H), 8.07 (d, J=8.4 Hz, 1H), 7.92 (s, 3H), 7.68 (d, J=1.0 Hz, 1H), 7.49-7.39 (m, 4H), 7.30 (d, J=7.4 Hz, 1H), 6.98 (s, 1H), 2.89-2.86 (m, 4H), 2.67 (s, 3H); $^{13}$C-NMR (126 MHz; DMSO-$d_6$): δ 154.2, 152.6, 144.9, 140.5, 136.1, 135.1, 130.40, 130.22, 129.1, 127.6, 126.4, 126.1, 120.7, 118.1, 113.1, 30.7, 19.5; one of the aliphatic carbon signals is obscured by the solvent peak; HRMS calcd for $C_{18}H_{20}N_3^+$: 278.1652; found, 278.1664.

7-(3-(2-Aminoethyl)phenyl)-4-methylquinolin-2-amine Dihydrochloride (12). Compounds 39 (0.075 g, 0.245 mmol) and 56 (0.070 g, 0.245 mmol) were coupled using General Procedure 1. Purification by flash column chromatography, eluting with a gradient of 5% EtOAc in $CH_2Cl_2$ to 40% EtOAc in $CH_2Cl_2$, afforded protected phenylquinoline 64 as a yellow foam (0.089 g, 90%). This compound was immediately deprotected using General Procedure 2. After workup, the free aminoquinoline was precipitated from EtOAc (2 mL) with hexanes (20 mL), and diluted in ether/MeOH (5:1). After treatment with methanolic HCl, 12 was obtained as a cream-colored flocculent solid (0.053 g, 72% from 64) after filtering, precipitating twice from hot MeOH (2 mL) with ether (10 mL), washing with ether, and drying in vacuo: mp 305.5-306.5° C. $^1$H-NMR (500 MHz; DMSO-$d_6$): δ 14.01 (s, 1H), 9.00 (br s, 1H), 8.41 (s, 3H), 8.25 (br s, 1H), 8.11 (d, J=8.5 Hz, 1H), 7.95-7.93 (m, 2H), 7.84 (dd, J=8.4, 1.2 Hz, 1H), 7.78 (d, J=7.6 Hz, 1H), 7.62-7.59 (m, 2H), 6.94 (s, 1H), 4.15 (q, J=5.3 Hz, 2H), 2.67 (s, 3H); $^{13}$C-NMR (126 MHz; DMSO-$d_6$): δ 154.4, 143.7, 139.2, 135.6, 130.1, 129.7, 128.3, 127.6, 126.8, 124.0, 121.1, 115.5, 113.2, 42.7, 19.4; two of the quinoline carbons are not visible due to baseline broadening; HRMS calcd for $C_{17}H_{18}N_3^+$: 264.1495; found, 264.1504.

7-(3-(2-Aminoethyl)phenyl)-4-methylquinolin-2-amine Dihydrochloride (13). Compounds 39 (0.075 g, 0.245 mmol) and 57 (0.077 g, 0.257 mmol) were coupled using General Procedure 1. Purification by flash column chromatography, eluting with a gradient of 5% EtOAc in $CH_2Cl_2$ to 45% EtOAc in $CH_2Cl_2$, afforded protected phenylquinoline 65 as a yellow syrup (0.090 g, 88%). This compound was immediately deprotected using General Procedure 2. After workup, the free aminoquinoline was diluted in ether/MeOH (5:1), and after treatment with methanolic HCl, ether (5 mL) was added and 13 was obtained as a tan hygroscopic semisolid (0.053 g, 71% from 65) after filtering, precipitating twice from hot MeOH (2 mL) with ether (10 mL), washing with ether, and drying in vacuo: $^1$H-NMR (500 MHz; DMSO-$d_6$): δ 14.17 (s, 1H), 9.00 (br s, 1H), 8.08-8.06 (m, 5H), 7.95 (d, J=1.4 Hz, 1H), 7.84 (dd, J=8.5, 1.5 Hz, 1H), 7.66-7.64 (m, 2H), 7.53 (t, J=7.8 Hz, 1H), 7.39 (d, J=7.6 Hz, 1H), 6.94 (s, 1H), 3.17-3.09 (m, 2H), 3.01 (t, J=7.8 Hz, 2H), 2.66 (s, 3H); $^{13}$C-NMR (126 MHz; DMSO-$d_6$): δ 154.3, 152.6, 144.1, 139.2, 139.0, 136.7, 130.1, 129.6, 128.0, 126.6, 126.1, 124.1, 120.9, 115.5, 113.0, 33.5, 19.4; HRMS calcd for $C_{18}H_{20}N_3^+$: 278.1652; found, 278.1662.

3-(2-Amino-4-methylquinolin-7-yl)-5-(aminomethyl) benzonitrile Dihydrochloride (14). Compounds 39 (0.075 g, 0.245 mmol) and 67 (0.083 g, 0.269 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 68 as a yellow foam (0.082 g, 78%). This compound was immediately deprotected using General Procedure 2. After workup, the free aminoquinoline was purified by flash column chromatography, eluting with a gradient of EtOAc to 5% MeOH in EtOAc to yield a white semisolid that was diluted in ether/MeOH (10:1). After treatment with methanolic HCl, ether (5 mL) was added, and 14 was obtained as a cream-colored solid (0.069 g, 68% from 68) after filtering, precipitating from hot MeOH (2 mL) with ether (10 mL), washing with ether, and drying in vacuo: mp >320° C. (darkens)>360° C. (melts or decomposes). $^1$H-NMR (500 MHz; DMSO-$d_6$): δ 14.15 (s, 1H), 9.10 (br s, 1 H), 8.63 (s, 3H), 8.40 (br s, 1H), 8.34 (s, 1H), 8.29 (s, 1H), 8.14 (d, J=8.5 Hz, 1H), 8.08 (s, 1 H), 7.99 (d, J=1.1 Hz, 1H), 7.91 (dd, J=8.5, 1.2 Hz, 1H), 6.99 (s, 1H), 4.21 (s, 2H), 2.67 (s, 3 H). $^{13}$C-NMR (126 MHz; DMSO-$d_6$): δ 154.6, 152.5, 141.6, 140.2, 137.2, 136.6, 133.36, 133.19, 131.1, 127.0, 124.1, 121.6, 118.8, 115.9, 113.6, 112.8, 41.9, 19.5; HRMS calcd for $C_{18}H_{17}N_4^+$: 289.1448; found, 289.1459.

7-(5-(Aminomethyl)pyridin-3-yl)-4-methylquinolin-2-amine Trihydrochloride (15). Compounds 39 (0.075 g, 0.245 mmol) and 70 (0.114 g, 0.294 mmol) were coupled using General Procedure 1. Purification by flash column chromatography, eluting with a gradient of 5% EtOAc in $CH_2Cl_2$ to 70% EtOAc in $CH_2Cl_2$, afforded protected phenylquinoline 71 as a white solid (0.080 g, 65%). $^1$H-NMR confirmed the presence of two Boc groups. This compound was immediately deprotected using General Procedure 2, and after 3 h, an additional equivalent of $K_2CO_3$ was added to remove one of the Boc groups. The mixture was heated a total of 4.5 h, and after workup, the free aminoquinoline was precipitated from EtOAc (0.5 mL) with hexanes (5 mL), and diluted in ether/MeOH (1:1). After treatment with methanolic HCl, ether (20 mL) was added and 15 was obtained as a tan solid (0.053 g, 90% from 71) after filtering, precipitating from hot MeOH (5 mL) with ether (10 mL), washing with ether, and drying in vacuo: mp 290-292° C. $^1$H-NMR (500 MHz; DMSO-$d_6$): δ 14.18 (s, 1H), 9.03 (d, J=2.0 Hz, 1H), 8.81 (d, J=1.6 Hz, 1H), 8.62 (s, 3H), 8.52 (s, 1H), 8.17 (d, J=8.5 Hz, 1H), 8.01 (d, J=1.5 Hz, 1H), 7.91 (dd, J=8.5, 1.7 Hz, 1H), 6.99 (s, 1H), 4.22 (q, J=5.7 Hz, 2H), 2.68 (s, 3H); the pyridinium-NH proton is broadened into residual water around 4 ppm; $^{13}$C-NMR (126 MHz; DMSO-$d_6$): δ 154.5, 152.7, 149.8, 147.5, 140.4, 137.0, 136.5, 134.4, 131.1, 127.2, 124.1, 121.5, 115.7, 113.6, 19.5; one of the aliphatic carbon signals is obscured by the solvent peak; HRMS calcd for $C_{16}H_{17}N_4^+$: 265.1459; found, 265.1464.

7-(Isoindolin-4-yl)-4-methylquinolin-2-amine Dihydrochloride (16). Compounds 39 (0.075 g, 0.245 mmol) and 74 (0.077 g, 0.257 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 74 as a yellow gum (0.093 g, 91%). This compound was immediately deprotected using General Procedure 2. After workup, the free aminoquinoline was purified by flash column chromatography, eluting with EtOAc to yield a pale yellow solid. The solid was diluted in ether/MeOH (2:1). After treatment with methanolic HCl, the mixture was concentrated, and the residue was diluted in MeOH (3 mL) and filtered through a small pad of Celite. Reconcentration afforded a residue that was then precipitated three times from hot MeOH (3 mL) with ether (10 mL) to yield 16 as a pale tan solid (0.040 g, 52% from 74) after washing with ether and drying in vacuo: mp 220-224° C. (softens), 233-235° C. (dec). $^1$H-NMR (500 MHz; DMSO-$d_6$): δ 13.98 (s, 1H), 9.87 (s, 2H), 9.00 (br s, 1H), 8.20 (br s, 1H), 8.09 (d, J=8.5 Hz, 1H), 7.78 (s, 1H), 7.63 (d, J=8.3 Hz, 1H), 7.59-7.53 (m, 3H), 6.95 (s, 1H), 4.64 (s, 2H), 4.61 (s, 2H), 2.66 (s, 3H); $^{13}$C-NMR (126 MHz; DMSO-$d_6$): δ 154.4, 152.3, 142.5, 137.1, 136.8, 135.5, 133.5, 129.9, 128.9, 126.6, 124.9, 123.7, 121.1, 117.2, 113.4, 50.5, 50.2, 19.4; HRMS calcd for $C_{18}H_{18}N_3^+$: 276.1495; found, 276.1508.

7-(1-Amino-2,3-dihydro-1H-inden-5-yl)-4-methylquinolin-2-amine Dihydrochloride (17). Compounds 39 (0.075 g, 0.245 mmol) and 79 (0.076 g, 0.245 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 81 as a yellow foam (0.091 g, 86%). This compound was immediately deprotected using General Procedure 2. After deprotection, the free aminoquinoline was precipitated from EtOAc (1 mL) with hexanes (20 mL), and the gel-like solid was filtered and diluted in ether/MeOH (2:1). After treatment with methanolic HCl, ether (8 mL) was added, and 17 was obtained as a white solid (0.059 g, 78% from 81) after precipitating from hot MeOH (5 mL) with ether (10 mL), washing with ether, and drying in vacuo: mp: >300° C. (darkens slowly), >340° C. (chars). $^1$H-NMR (500 MHz; DMSO-$d_6$): δ 13.98 (s, 1H), 9.00 (br s, 1H), 8.49 (s, 3H), 8.10 (br s, 1H), 8.07 (d, J=8.5 Hz, 1H), 7.94 (s, 1H), 7.82 (dd, J=8.5, 1.3 Hz, 1H), 7.76-7.69 (m, 3H), 3.20-3.14 (m, 1H), 3.02-2.95 (m, 1H), 2.57-2.54 (m, 1H), 2.10-2.03 (m, 1H); $^{13}$C-NMR (126 MHz; DMSO-$d_6$): δ 154.3, 145.8, 143.9, 140.5, 139.9, 126.7, 126.32, 126.18, 124.10, 124.01, 121.0, 115.8, 113.1, 54.9, 31.0, 30.4, 19.4; two of the quinoline carbons are not visible due to baseline broadening; HRMS calcd for $C_{19}H_{20}N_3^+$: 290.1652; found, 290.1663.

7-(3-Amino-2,3-dihydro-1H-inden-5-yl)-4-methylquinolin-2-amine Dihydrochloride (18). Compounds 39 (0.075 g, 0.245 mmol) and 80 (0.076 g, 0.245 mmol) were coupled using General Procedure 1. Purification by flash column chromatography, eluting with a gradient of 2% EtOAc in $CH_2Cl_2$ to 35% EtOAc in $CH_2Cl_2$, afforded protected phenylquinoline 82 as a yellow semisolid (0.093 g, 88%). This compound was immediately deprotected using General Procedure 2. After deprotection, the free aminoquinoline was purified by flash column chromatography, eluting with EtOAc. Concentration afforded a residue that was diluted in MeOH. After treatment with methanolic HCl, the mixture was concentrated, azeotroped with toluene twice, and 18 was obtained as a white solid (0.064 g, 82% from 82) after precipitating twice from hot MeOH (2 mL) with ether (10 mL), washing with ether, and drying in vacuo: mp 250-256° C. (darkens, then chars). $^1$H-NMR (500 MHz; DMSO-$d_6$): δ 14.15 (s, 1H), 9.00 (br s, 1H), 8.61 (s, 3H), 8.20 (br s, 1H), 8.11 (t, J=4.2 Hz, 2H), 7.90 (d, J=1.5 Hz, 1H), 7.79 (dd, J=8.5, 1.6 Hz, 1H), 7.74 (dd, J=7.9, 1.5 Hz, 1H), 7.51 (d, J=7.9 Hz, 1H), 6.94 (s, 1H), 4.83-4.80 (m, 1H), 3.14 (ddd, J=19.1, 7.1, 4.3 Hz, 1H), 2.98-2.92 (m, 1H), 2.58-2.52 (m, 1H), 2.10-2.03 (m, 1H); $^{13}$C-NMR (126 MHz; DMSO-$d_6$): δ 154.5, 145.3, 144.1, 141.1, 137.6, 136.8, 128.4, 126.9, 126.2, 124.3, 123.9, 120.9, 115.2, 113.0, 55.1, 31.0, 30.2, 19.4; HRMS calcd for $C_{19}H_{20}N_3^+$: 290.1652; found, 290.1664.

7-(3-(Aminomethyl)-4-fluorophenyl)-4-methylquinolin-2-amine Dihydrochloride (19). Compounds 39 (0.075 g, 0.245 mmol) and 87 (0.099 g, 0.282 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 117 as a dark yellow foam (0.088 g, 85%). This compound was immediately deprotected using General Procedure 2. After workup, the free aminoquinoline was diluted in ether/MeOH (5:1). After treatment with methanolic HCl, 19 was obtained as a cream-colored flocculent solid (0.060 g, 81% from 117) after precipitating from hot MeOH (1 mL) with ether (10 mL), washing with ether, and drying in vacuo: mp 300-302° C. (dec). $^1$H-NMR (500 MHz; DMSO-$d_6$): δ 14.08 (s, 1H), 9.05 (br s, 1H), 8.52 (s, 3H), 8.25 (br s, 1H), 8.12-8.08 (m, 2H), 7.92 (d, J=1.4 Hz, 1H), 7.86-7.82 (m, 2H), 7.49 (t, J=9.2 Hz, 1H), 6.95 (s, 1H), 4.18 (br d, J=3.2 Hz, 2H), 2.67 (s, 3H); $^{13}$C-NMR (126 MHz; DMSO-$d_6$): δ (162.1+160.1, 1 C), 154.5, 152.6, 142.8, 136.6, (135.34+135.31, 1 C), (130.90+130.87), 1 C), (129.99+129.92, 1 C), 126.9, 124.0, (122.47+122.35, 1 C), (117.05+116.87, 1 C), 115.3, 113.2, (36.17+36.14, 1 C), 19.5; HRMS calcd for $C_{17}H_{17}FN_3^+$: 282.1401; found, 282.1408.

7-(3-(Aminomethyl)-4-chlorophenyl)-4-methylquinolin-2-amine Dihydrochloride (20). Compounds 39 (0.075 g, 0.245 mmol) and 88 (0.105 g, 0.282 mmol) were coupled using General Procedure 1. Purification by flash column chromatography, eluting with a gradient of 5% EtOAc in $CH_2Cl_2$ to 40% EtOAc in $CH_2Cl_2$, afforded protected phenylquinoline 118 as a yellow foam (0.095 g, 88%). This compound was immediately deprotected using General Procedure 2. After workup, the free aminoquinoline was diluted in ether/MeOH (5:1). After treatment with methanolic HCl, 20 was obtained as a cream-colored powder (0.057 g, 71% from 118) after precipitating four times from hot MeOH (2 mL) with ether (15 mL), washing with ether, and drying in vacuo: mp 249-250° C. (softens slightly), 255-257° C. (melts). $^1$H-NMR (500 MHz; DMSO-$d_6$): δ 14.13 (s, 1H), 8.65 (s, 3H), 8.13-8.11 (m, 2H), 7.95 (d, J=1.5 Hz, 1H), 7.87 (dd, J=8.5, 1.1 Hz, 1H), 7.81 (dd, J=8.4, 2.2 Hz, 1H), 7.72 (d, J=8.4 Hz, 1H), 6.95 (s, 1H), 4.24 (s, 2H), 3.39-3.30 (m, 3H), 2.66 (s, 3H); the aminoquinoline-NH protons are not visible as discrete peaks, but are broadened into the baseline around 8.4 ppm; $^{13}$C-NMR (126 MHz; DMSO-$d_6$): δ 154.7, 152.5, 142.3, 138.1, 133.8, 132.9, 130.8, 130.0, 129.1, 126.9, 123.8, 121.4, 115.8, 113.3, 19.4; one of the quinoline carbons is not visible due to baseline broadening; one of the aliphatic carbon signals is obscured by the solvent peak; HRMS calcd for $C_{17}H_{17}ClN_3^+$: 298.1106; found, 298.1114.

7-(3-(Aminomethyl)-4-trifluoromethylphenyl)-4-methylquinolin-2-amine Dihydrochloride (21). Compounds 39 (0.075 g, 0.245 mmol) and 90 (0.100 g, 0.282 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 119 as a yellow solid (0.102 g, 88%). This compound was immediately deprotected using General Procedure 2. After workup, the free aminoquinoline was purified by flash column chromatography, eluting with EtOAc to yield a pale yellow gum that was diluted in ether/MeOH (10:1). After treatment with methanolic HCl, ether (5 mL) was added, and 21 was obtained as a cream-colored powder (0.054 g, 62% from 119) after precipitating from hot MeOH (2 mL) with ether (10 mL), washing with ether, and drying in vacuo: mp 327-329° C. $^1$H-NMR (500 MHz; DMSO-$d_6$): δ 14.09 (s, 1H), 9.00 (br s, 1H), 8.30 (br s, 1H), 8.76 (s, 3H), 8.31 (s, 1H), 8.17 (d, J=8.5 Hz, 1H), 8.03 (d, J=1.5 Hz, 1H), 7.99-7.95 (m, 3H), 6.98 (s, 1H), 4.29 (s, 2H), 2.68 (s, 3H); $^{13}$C-NMR (126 MHz; DMSO-$d_6$): δ 154.6, 152.4, 143.0, 141.9, 136.8, 133.6, 130.2, 127.82, (127.77+127.73+127.68+127.64+127.59, 1 C), (127.49+127.3, 1 C), (125.6+123.4, 1 C), 127.0, 124.2, 121.7, 116.1, 113.7, 39.14, 39.13, 19.5; the splitting of the signals for the trifluoromethyl group and nearby carbons is partially obscured by other signals; HRMS calcd for $C_{18}H_{17}F_3N_3^+$: 332.1369; found, 332.1383.

7-(3-(Aminomethyl)-4-ethylphenyl)-4-methylquinolin-2-amine Dihydrochloride (22). Compounds 39 (0.060 g, 0.196 mmol) and 95 (0.065 g, 0.206 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 120 as a cream-colored solid (0.074 g, 87%). This compound was immediately deprotected using General Procedure 2. After workup, the free aminoquinoline was triturated with 5% EtOAc in hexanes and the solid was collected, washed with hexanes, diluted in EtOAc, filtered, and concentrated. The residue was diluted in ether/MeOH (6:1). After treatment with methanolic HCl, the mixture was concentrated, and 22 was obtained as a an off-white solid (0.035 g, 56% from 120) after precipitating three times from hot MeOH (1.5 mL) with ether (10 mL), washing with ether, and drying in vacuo: mp 307-309° C. $^1$H-NMR (500 MHz; DMSO-$d_6$): δ 14.06 (s, 1H), 9.05 (br s, 1H), 8.48 (s, 3H), 8.25 (br s, 1H), 8.10 (d, J=8.5 Hz, 1H), 7.94 (t, J=2.2 Hz, 2H), 7.88 (dd, J=8.5, 1.6 Hz, 1H), 7.73 (dd, J=8.0, 1.8 Hz, 1H), 7.46 (d, J=8.1 Hz, 1H), 6.94 (d, J=0.6 Hz, 1H), 4.16-4.13 (m, 2H), 2.76 (q, J=7.5 Hz, 2H), 2.65 (s, 3H), 1.22 (t, J=7.5 Hz, 3H); $^{13}$C-NMR (126 MHz; DMSO-$d_6$): δ 154.4, 152.7, 143.71, 143.55, 136.65, 136.54, 133.1, 130.0, 128.6, 127.6, 126.7, 124.0, 120.9, 115.0, 113.0, 39.5, 25.1, 19.5, 15.4; HRMS calcd for $C_{19}H_{22}N_3^+$: 292.1808; found, 292.1815.

7-(3-(Aminomethyl)-4-methoxyphenyl)-4-methylquinolin-2-amine Dihydrochloride (23). Compounds 39 (0.075 g, 0.245 mmol) and 98 (0.085 g, 0.269 mmol) were coupled using General Procedure 1. Purification by flash column chromatography, eluting with a gradient of 5% EtOAc in $CH_2Cl_2$ to 40% EtOAc in $CH_2Cl_2$, afforded protected phenylquinoline 121 as a yellow foam (0.077 g, 72%). This compound was immediately deprotected using General Procedure 2. After workup, the free aminoquinoline was triturated with hexanes. The solid was collected and diluted in ether/MeOH (8:1). After treatment with methanolic HCl, 23 was obtained as a yellow amorphous solid (0.057 g, 88% from 121) after precipitating from hot MeOH (5 mL) with ether (10 mL), washing with ether, and drying in vacuo: mp 232-234° C. $^1$H-NMR (500 MHz; DMSO-$d_6$): δ 14.16 (s, 1H), 9.00 (br s, 1H), 8.34-8.30 (2 br s, 4H), 8.07 (d, J=8.6 Hz, 1H), 7.91 (d, J=2.2 Hz, 1H), 7.90 (d, J=1.4 Hz, 1H), 7.82 (ddd, J=8.5, 4.7, 2.0 Hz, 2H), 7.26 (d, J=8.7 Hz, 1H), 6.93 (s, 1H), 4.08 (q, J=5.3 Hz, 2H), 3.92 (s, 3H), 2.65 (s, 3H); $^{13}$C-NMR (126 MHz; DMSO-$d_6$): δ 158.3, 154.4, 152.7, 143.5, 136.7, 130.8, 129.7, 129.3, 126.7, 123.7, 123.1, 120.5, 114.5, 112.7, 112.4, 56.4, 38.1, 19.4; HRMS calcd for $C_{18}H_{20}N_3O^+$: 294.1601; found, 294.1611.

7-(3-(Aminomethyl)-4-ethoxyphenyl)-4-methylquinolin-2-amine Dihydrochloride (24). Compounds 39 (0.075 g, 0.245 mmol) and 101 (0.089 g, 0.269 mmol) were coupled using General Procedure 1. Purification by flash column chromatography, eluting with a gradient of 5% EtOAc in $CH_2Cl_2$ to 40% EtOAc in $CH_2Cl_2$, afforded protected phenylquinoline 122 as a cream-colored solid (0.072 g, 65%). This compound was immediately deprotected using General Procedure 2. After workup, the free aminoquinoline was triturated with hexanes. The solid was collected and diluted in ether/MeOH (2:1). After treatment with methanolic HCl, 24 was obtained as a yellow glassy solid (0.060 g, 99% from 122) after washing with 2% MeOH in ether, diluting in MeOH and reconcentrating, washing with ether, and drying in vacuo: mp 250° C. softens), 265-267° C. (bubbles, melts). $^{1}$H-NMR (500 MHz; DMSO-$d_6$): δ 14.23 (s, 1H), 9.07 (br s, 1H), 8.39 (s, 3H), 8.25 (br s, 1H), 8.07 (d, J=8.6 Hz, 1H), 7.92 (d, J=2.1 Hz, 1H), 7.89 (d, J=1.2 Hz, 1H), 7.82 (dd, J=8.5, 1.4 Hz, 1H), 7.78 (dd, J=8.6, 2.2 Hz, 1H), 7.24 (d, J=8.7 Hz, 1H), 6.93 (s, 1H), 4.18 (br q, J=6.9 Hz, 2H), 4.07 (d, J=5.4 Hz, 2H), 2.65 (s, 3H), 1.42 (t, J=6.9 Hz, 3 H); $^{13}$C-NMR (126 MHz; DMSO-$d_6$): δ 157.5, 154.4, 152.6, 143.5, 136.7, 130.6, 129.6, 129.2, 126.7, 123.7, 123.1, 120.5, 114.4, 113.0, 112.7, 64.5, 37.9, 19.4, 15.0; HRMS calcd for $C_{19}H_{22}N_3O^+$: 308.1757; found, 308.1772.

7-(3-(Aminomethyl)-4-propoxyphenyl)-4-methylquinolin-2-amine Dihydrochloride (25). Compounds 39 (0.075 g, 0.245 mmol) and 104 (0.093 g, 0.269 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 123 as an off-white solid (0.083 g, 73%). This compound was immediately deprotected using General Procedure 2. After deprotection, the free aminoquinoline was triturated with 5% EtOAc in hexanes (15 mL), and the obtained solid was diluted in ether/MeOH (2:1). After treatment with methanolic HCl, the mixture was concentrated, the residue was azeotroped twice with toluene, and 25 was obtained as a yellow glassy solid (0.044 g, 62% from 123) after precipitating twice from hot MeOH (2 mL) with ether (10 mL), and drying in vacuo: mp 220° C. (softens), 264-266° C. (bubbles, melts). $^{1}$H-NMR (500 MHz; DMSO-$d_6$): δ 14.06 (s, 1H), 9.00 (br s, 1H), 8.32 (s, 4H), 8.07 (d, J=8.5 Hz, 1 H), 7.91 (d, J=2.2 Hz, 1H), 7.89 (d, J=1.4 Hz, 1H), 7.82 (dd, J=8.6, 1.2 Hz, 1H), 7.78 (dd, J=8.6, 2.3 Hz, 1H), 7.25 (d, J=8.7 Hz, 1H), 6.91 (s, 1H), 4.09 (br t, J=6.5 Hz, 4H), 2.63 (t, J=1.8 Hz, 3H), 1.83 (sextet, J=7.0 Hz, 2H), 1.03 (t, J=7.4 Hz, 3H); $^{13}$C-NMR (126 MHz; DMSO-$d_6$): δ 157.6, 154.4, 143.51, 130.7, 129.4, 129.2, 126.7, 123.6, 123.2, 120.6, 114.6, 113.1, 112.7, 70.2, 37.8, 22.4, 19.4, 10.9; two of the quinoline carbons are not visible due to baseline broadening; HRMS calcd for $C_{20}H_{24}N_3O^+$: 322.1914; found, 322.1927.

7-(3-(Aminomethyl)-4-isopropoxyphenyl)-4-methylquinolin-2-amine Dihydrochloride (26). Compounds 39 (0.075 g, 0.245 mmol) and 105 (0.093 g, 0.269 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 124 as an off-white solid (0.083 g, 73%). This compound was immediately deprotected using General Procedure 2. After deprotection, the free aminoquinoline was precipitated from EtOAc (1 mL) with hexanes (10 mL) and the obtained solid was diluted in ether/MeOH (4:1). After treatment with methanolic HCl, the mixture was concentrated and azeotroped twice with toluene, and 26 was obtained as an off-white solid (0.0097 g, 14% from 124) after precipitating twice from hot MeOH (1 mL) with ether (10 mL), washing with ether, and drying in vacuo: mp 237-239° C. (softens), 245-246° C. (melts). $^{1}$H-NMR (500 MHz; DMSO-$d_6$): δ 13.97 (s, 1H), 9.00 (br s, 1H), 8.26 (br s, 4H), 8.07 (d, J=8.6 Hz, 1H), 7.89 (d, J=9.5 Hz, 2H), 7.81 (d, J=8.3 Hz, 1H), 7.77 (d, J=8.7 Hz, 1H), 7.28 (d, J=8.4 Hz, 1H), 6.91 (s, 1H), 4.81-4.75 (m, 1H), 4.06 (d, J=4.9 Hz, 2H), 2.66 (s, 3H), 1.37 (d, J=6.0 Hz, 6 H; $^{13}$C-NMR (126 MHz; DMSO-$d_6$): δ 156.5, 154.5, 152.5, 143.5, 136.9, 130.4, 129.5, 129.0, 126.7, 123.80, 123.61, 120.5, 114.5, 114.2, 112.7, 71.0, 37.9, 22.2 (2 C), 19.4; HRMS calcd for $C_{20}H_{24}N_3O^+$: 322.1914; found, 322.1933.

7-(3-(Aminomethyl)-4-isobutoxyphenyl)-4-methylquinolin-2-amine Dihydrochloride (27). Compounds 39 (0.050 g, 0.163 mmol) and 106 (0.058 g, 0.160 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 125 as a yellow (0.056 g, 72%). This compound was immediately deprotected using General Procedure 2. After deprotection, the free aminoquinoline was diluted in MeOH (10 mL), filtered, and diluted with 4 mL ether. After treatment with methanolic HCl, the mixture was concentrated and azeotroped with toluene twice to yield 27 as a cream-colored solid (0.043 g, 90% from 125) after precipitating from MeOH (2 mL) with ether (15 mL), washing with ether, and drying in vacuo: mp: 283-285° C. (softens, bubbles), 308° C. (chars). $^{1}$H-NMR (500 MHz; DMSO-$d_6$): δ 13.85 (s, 1H), 8.26 (s, 3H), 8.08 (d, J=8.5 Hz, 1H), 7.89 (dd, J=8.8, 1.6 Hz, 2H), 7.82-7.78 (m, 2H), 7.26 (d, J=8.7 Hz, 1H), 6.90 (s, 1H), 4.11 (q, J=5.4 Hz, 2H), 3.91 (d, J=6.5 Hz, 2H), 2.66 (s, 3H), 2.16-2.10 (m, 1H), 1.04 (d, J=6.7 Hz, 6H); the aminoquinoline-NH protons are broadened into the baseline around 8.5 ppm; $^{13}$C-NMR (126 MHz; DMSO-$d_6$): δ 157.5, 154.4, 152.7, 143.5, 130.7, 129.23, 129.12, 126.7, 123.6, 123.2, 120.6, 114.5, 113.1, 112.7, 74.8, 37.7, 28.1, 19.60, 19.43; one of the aminoquinoline carbons is not visible due to baseline broadening; HRMS calcd for $C_{21}H_{26}N_3O^+$: 336.2070; found, 336.2080.

7-(3-(Aminomethyl)-4-(cyclobutylmethoxy)phenyl)-4-methylquinolin-2-amine Dihydrochloride (28). Compounds 39 (0.082 g, 0.270 mmol) and 107 (0.110 g, 0.300 mmol) were coupled using General Procedure 1. Purification by flash column chromatography, eluting with a gradient of 5% EtOAc in $CH_2Cl_2$ to 80% EtOAc in $CH_2Cl_2$, afforded protected phenylquinoline 126 as a tan foam (0.052 g, 40%). A portion of this compound (0.04 g) was immediately deprotected using General Procedure 2. After workup, the free aminoquinoline was taken up in MeOH (1.0 mL) and treated with methanolic HCl for 18 h. The mixture was concentrated to minimal solvent and triturated with ether (10 mL) 3× to afford 28 as an off-white solid (0.031 g, 88% from 126) after filtering, washing with ether, and drying in vacuo: mp 83-84° C. (softens)>209.5° C. (darkens)>241.2° C. (dec) $^{1}$H-NMR (500 MHz, DMSO-$d_6$) δ 14.38 (s, 1H), 9.20 (bs, 1 H), 8.58 (s, 3H), 8.28 (bs, 1H), 8.05 (d, J=8.4 Hz, 1H), 7.97 (d, J=2.3 Hz, 1H), 7.88 (d, J=1.7 Hz, 1H), 7.84 (dd, J=8.6, 1.7 Hz, 1H), 7.75 (dd, J=8.6, 2.4 Hz, 1H), 7.24 (d, J=8.6 Hz, 1 H), 6.96 (s, 1H), 4.09 (d, J=6.4 Hz, 2H), 4.06 (d, J=5.3 Hz, 2H), 2.81 (hept, J=7.0 Hz, 1H), 2.64 (s, 3H), 2.18-2.05 (m, 2H), 1.99-1.82 (m, 4H). $^{13}$C-NMR (126 MHz, DMSO-$d_6$) δ 156.97, 153.88, 151.95, 143.00, 135.99, 130.05, 128.66, 128.37, 126.08, 123.12, 122.73, 119.86, 113.68, 112.59, 112.08, 71.86, 36.84, 33.78, 24.15, 18.85, 18.07; one of the aminoquinoline carbons is not visible due to baseline broadening; HRMS calcd for $C_{22}H_{26}N_3O_4^+$: 348.2076; found, 348.2073.

7-(3-(Aminomethyl)-4-(cyclopropylmethoxy)phenyl)-4-methylquinolin-2-amine Dihydrochloride (29). Compound 108 (0.078 g, 0.219 mmol), tetrahydroxydiboron (0.059 g, 0.77 mmol), and KOAc (0.064 g, 0.66 mmol), XPhos-Pd-G3 (2.4 mg, 2.8 μmol), and XPhos (2.6 mg, 5.5 μmol) was added to an oven-dried glass vial equipped with a Teflon-lined cap.[49] EtOH (2.2 mL degassed) was then added to the reaction vessel and a nitrogen stream was allowed to bubble through the solution at room temperature for 15 min with stirring. The vessel was then sealed, and the reaction mixture was heated to 80° C. for the 2 h. The reaction was then allowed to cool to ambient temperatures before 3 equiv (0.364 mL, 0.66 mmol) of 1.8 M degassed aqueous $K_2CO_3$ was added via syringe followed by compound 38 (0.055 g, 0.20 mmol). The reaction vial was degassed with argon, resealed with a Teflon-lined cap, and left to stir at 80° C. for an additional 15 h. The reaction mixture was cooled to room temperature and partitioned between EtOAc and $H_2O$ (20 mL each). The layers were separated, the aqueous layer was extracted with EtOAc (3×20 mL), the organic layer was washed with 5% aq. NaCl (2×20 mL) and sat. aq. NaCl (20 mL), dried over anhydrous sodium sulfate, and concentrated. Purification by flash column chromatography, eluting with a gradient of 5% EtOAc in $CH_2Cl_2$ to 90% EtOAc in $CH_2Cl_2$, afforded protected phenylquinoline 127 as a colorless solid (0.073 g, 78%). A portion of this compound (0.069 g) was immediately deprotected using General Procedure 2. After workup, the free aminoquinoline was taken up in MeOH (3.0 mL) and treated with methanolic HCl for 18 h, and concentrated to dryness. The title compound (29) was obtained as a yellow-colored solid (0.029 g, 49% from 127) after reverse phase flash column chromatography, eluting through a 15.5 g C18 RediSep RF Gold cartridge column with a gradient of 100% water to 100% acetonitrile, azeotropic removal of water with toluene, and drying in vacuo: mp >193.5° C. (foam dec) $^1$H-NMR (500 MHz, DMSO-$d_6$) δ 14.30 (s, 1H), 8.50 (s, 3H), 8.06 (d, J=8.5 Hz, 1H), 7.95 (d, J=2.4 Hz, 1H), 7.89 (d, J=1.7 Hz, 1H), 7.83 (dd, J=8.6, 1.8 Hz, 1H), 7.75 (dd, J=8.7, 2.4 Hz, 1H), 7.23 (d, J=8.7 Hz, 1H), 6.99-6.87 (m, 1H), 4.09 (d, J=5.0 Hz, 2H), 3.99 (d, J=6.9 Hz, 2H), 2.65 (s, 3H), 1.33 (tt, J=7.3, 5.0 Hz, 1H), 0.61 (td, J=7.7, 6.1, 4.5 Hz, 2H), 0.41 (q, J=4.9 Hz, 2H); 13C NMR (126 MHz, DMSO-$d_6$) δ 156.93, 153.87, 151.99, 142.97, 136.11, 130.08, 128.75, 128.43, 126.09, 123.08, 122.71, 119.91, 113.79, 112.80, 112.10, 72.70, 37.08, 18.84, 9.93, 3.01; HRMS calcd for $C_{21}H_{24}N_3O^+$: 334.1914; found, 334.1910.

7-(3-(Aminomethyl)-4-((3-fluorobenzyl)oxy)phenyl)-4-methylquinolin-2-amine Dihydrochloride (30). Compounds 39 (0.060 g, 0.196 mmol) and 109 (0.090 g, 0.216 mmol) were coupled using General Procedure 1. Purification by flash column chromatography, eluting with a gradient of 5% EtOAc in $CH_2Cl_2$ to 35% EtOAc in $CH_2Cl_2$, afforded protected phenylquinoline 128 as a brown foam (0.078 g, 76%). This compound was immediately deprotected using General Procedure 2. After deprotection, the free aminoquinoline was purified by passing through a short plug of $SiO_2$, washing with EtOAc and then 10% MeOH in EtOAc. Concentration afforded a residue that was diluted in ether/MeOH (2:1). After treatment with methanolic HCl, the mixture was concentrated, and 30 was obtained as a white solid (0.057 g, 84% from 128) after precipitating twice from MeOH (2 mL) with ether (10 mL), and drying in vacuo: mp 242-243.5° C. $^1$H-NMR (500 MHz; DMSO-$d_6$): δ 14.00 (s, 1H), 9.00 (br s, 1H), 8.35 (br s, 4H), 8.07 (d, J=8.5 Hz, 1 H), 7.94 (d, J=2.2 Hz, 1H), 7.89 (d, J=1.4 Hz, 1H), 7.81 (ddd, J=12.4, 8.8, 1.8 Hz, 2H), 7.50-7.46 (m, 1H), 7.43-7.38 (m, 2H), 7.29 (d, J=8.7 Hz, 1H), 7.19 (td, J=8.7, 2.2 Hz, 1H), 6.91 (s, 1H), 4.16 (br q, J=5.5 Hz, 2H), 2.65 (s, 3H); $^{13}$C-NMR (126 MHz; DMSO-$d_6$): δ (163.8 +161.8, 1 C) 157.0, 154.4, 152.8, 143.4, (140.16+140.10, 1 C), 131.19, (131.06+130.99, 1 C), 129.7, 129.2, 126.7, 123.88, (123.86+ 123.67, 1 C), 123.5, 120.6, (115.31+115.15, 1 C), (114.74 +114.57, 1 C), 113.6, 112.8, 69.4, 37.9, 19.4; three of the quinoline and aryl ring carbons are not visible because of baseline broadening; HRMS calcd for $C_{24}H_{23}FN_3O^+$: 388.1820; found, 388.1828.

4-((4-(2-Amino-4-methylquinolin-7-yl)-2-(aminomethyl)phenoxy)methyl)benzonitrile Dihydrochloride (31). Compounds 39 (0.075 g, 0.245 mmol) and 1110 (0.102 g, 0.245 mmol) were coupled using General Procedure 1. After workup, the crude residue was suspended in EtOAc/ether (1:1) and filtered through a small pad of Celite overlaid with silica. The filtrate was concentrated to yield a residue that was washed with 5% hexanes/EtOAc (30 mL) to afford 129 as a white solid (0.073 g, 56%) after washing with hexanes. This compound was immediately deprotected using General Procedure 2. After deprotection, the free aminoquinoline was purified by flash column chromatography, eluting with a gradient of EtOAc to 2% MeOH in EtOAc to yield a white solid that was diluted in ether/MeOH (2:1). After treatment with methanolic HCl, the mixture was concentrated, the residue was azeotroped with toluene, and 31 was obtained as a white solid (0.054 g, 84% from 129) after precipitating twice from MeOH (3 mL) with ether (15 mL), and drying in vacuo: mp 280-282° C. $^1$H-NMR (500 MHz; DMSO-$d_6$): δ 14.03 (s, 1H), 8.37 (s, 3H), 8.06 (d, J=8.4 Hz, 1H), 7.94-7.88 (m, 4H), 7.80-7.75 (m, 4H), 7.27 (d, J=8.5 Hz, 1H), 6.90 (s, 1H), 5.40 (s, 2H), 4.17 (s, 2 H), 2.64 (s, 3H); the aminoquinoline-NH protons are not visible as discrete peaks, but are broadened into the baseline around 8.4 and 7.9 ppm; $^{13}$C-NMR (126 MHz; DMSO-$d_6$): δ 19.38, 37.79, 69.30, 111.09, 112.77, 113.52, 115.19, 119.23, 120.72, 123.49, 126.60, 128.52, 129.11, 129.80, 131.43, 132.93, 143.01, 143.16, 154.74, 156.78; three of the aminoquinoline and aryl carbons are not visible because of baseline broadening; HRMS calcd for $C_{25}H_{23}N_4O^+$: 395.1866; found, 395.1872.

7-(3-(Aminomethyl)-4-(pyridin-2-ylmethoxy)phenyl)-4-methylquinolin-2-amine Trihydrochloride (32). Compounds 39 (0.075 g, 0.245 mmol) and 111 (0.096 g, 0.245 mmol) were coupled using General Procedure 1. Purification by flash column chromatography, eluting with a gradient of 10% EtOAc in $CH_2Cl_2$ to 85% EtOAc in $CH_2Cl_2$, afforded protected phenylquinoline 130 as a white powder (0.091 g, 72%) after precipitating from EtOAc (1 mL) with hexanes (20 mL). This compound was immediately deprotected using General Procedure 2. After deprotection, the free aminoquinoline was purified by flash column chromatography, eluting with a gradient of EtOAc to 15% MeOH in EtOAc. Concentration afforded a residue that was diluted in MeOH. After treatment with methanolic HCl, the mixture was concentrated, the residue was azeotroped three times with toluene, and 32 was obtained as a white powder (0.063 g, 74% from 130) after precipitating three times from MeOH (5 mL) with ether (10 mL), washing with ether, and drying in vacuo: mp 231-233° C. (dec). $^1$H-NMR (500 MHz; DMSO-$d_6$): δ 14.08 (s, 1H), 9.04 (br s, 1H), 8.66 (d, J=4.8 Hz, 1H), 8.46 (s, 3H), 8.22 (br s, 1H), 8.08 (d, J=8.6 Hz, 1H), 7.99 (t, J=7.3 Hz, 1H), 7.94 (d, J=2.3 Hz, 1H), 7.89 (d, J=1.6 Hz, 1H), 7.82 (dd, J=8.6, 1.7 Hz, 1H), 7.79 (dd, J=8.6, 2.3 Hz, 1H), 7.72 (d, J=7.8 Hz, 1H), 7.49 (t, J=6.1 Hz, 1H), 7.33 (d, J=8.7 Hz, 1H), 6.92 (s, 1H), 4.21 (d, J=5.7 Hz, 2H); the pyridinium-NH proton is broadened into residual water around 4.3 ppm; $^{13}$C-NMR (126 MHz; DMSO-$d_6$): δ 157.1, 156.0, 154.4, 152.7, 148.7, 143.4, 139.0, 136.6, 131.5, 130.0, 129.3, 126.8, 124.2, 123.73, 123.67, 122.8, 120.6, 114.6, 113.8, 112.8, 70.4, 38.3, 19.4; HRMS calcd for $C_{23}H_{23}N_4O^+$: 371.1866; found, 371.1880.

7-(3-(Aminomethyl)-4-(pyridin-3-ylmethoxy)phenyl)-4-methylquinolin-2-amine Trihydrochloride (33). Compounds 39 (0.075 g, 0.245 mmol) and 112 (0.096 g, 0.245 mmol)

were coupled using General Procedure 1. As the product was poorly soluble in EtOAc, the aqueous layer was extracted with 200 mL of EtOAc during the workup. After concentration, the residue was washed with 50% hexanes/EtOAc (30 mL) to afford 131 as an off-white solid (0.100 g, 80%) after washing with hexanes. This compound was immediately deprotected using General Procedure 2. After deprotection, the free aminoquinoline was purified by flash column chromatography, eluting with a gradient of 3% MeOH in EtOAc to 15% MeOH in EtOAc to yield a colorless foam. This was diluted with ether/MeOH (1:1). After treatment with methanolic HCl, the mixture was concentrated, and 33 was obtained as a pale orange solid (0.062 g, 66% from 131) after precipitating twice from hot MeOH (1 mL) with ether (10 mL), washing with ether, and drying in vacuo: mp 238-240° C. (softens) 248-250° C. (melts). $^{1}$H-NMR (500 MHz; DMSO-$d_6$): δ 14.07 (s, 1H), 9.00 (br s, 1H), 8.94 (s, 1H), 8.72 (d, J=4.7 Hz, 1H), 8.39 (s, 3H), 8.30 (d, J=6.9 Hz, 1H), 8.25 (br s, 1H), 8.08 (d, J=8.6 Hz, 1H), 7.95 (d, J=2.1 Hz, 1H), 7.90 (d, J=1.3 Hz, 1H), 7.84-7.81 (m, 2H), 7.74-7.72 (m, 1H), 7.35 (d, J=8.7 Hz, 1H), 6.93 (s, 1H), 5.40 (s, 2H), 4.15 (q, J=5.5 Hz, 3H), 2.66 (s, 3H); the pyrdinium —NH proton is broadened into residual water around 4.0 ppm; $^{13}$C-NMR (126 MHz; DMSO-$d_6$): δ 156.9, 154.4, 152.8, 146.9, 143.4, 136.6, 134.4, 131.4, 130.0, 129.3, 126.8, 125.4, 123.74, 123.55, 120.6, 114.5, 113.6, 112.8, 67.5, 37.9, 19.4; one of the quinoline carbons is not visible due to baseline broadening; $^{13}$C-NMR (126 MHz; DMSO-$d_6$): δ 157.1, 156.0, 154.4, 152.7, 148.6, 143.4, 139.0, 136.6, 131.5, 130.0, 129.3, 126.8, 124.2, 123.73, 123.67, 122.8, 120.6, 114.6, 113.8, 112.8, 70.4, 38.3, 19.4; HRMS calcd for $C_{23}H_{23}N_4O^+$: 371.1866; found, 371.1878.

7-(3-(Aminomethyl)-4-((5-methylisoxazol-3-yl)methoxy)phenyl)-4-methylquinolin-2-amine Dihydrochloride (34). Compounds 39 (0.085 g, 0.276 mmol) and 113 (0.132 g, 0.33 mmol) were coupled using General Procedure 1. Purification by flash column chromatography, eluting with a gradient of 5% EtOAc in $CH_2Cl_2$ to 70% EtOAc in $CH_2Cl_2$, afforded protected phenylquinoline 133 as a white solid (0.032 g, 22%). This compound was immediately deprotected using General Procedure 2. After workup, the free aminoquinoline was taken up in MeOH (1.0 mL) and treated with methanolic HCl (1 mL) for 18 h, resulting in the formation of a white precipitate, which was concentrated to dryness. The title compound (34) was obtained as a tan solid (0.012 g, 43% from 133) after recrystallization overnight from methanol that was slowly diffused with ether, followed by removal of mother liquor, washing with 1:20 methanol-ether, and drying in vacuo: mp >267° C. (browns slowly) 272-274° C. (melts/gels)>277° C. (foams and decomp.). $^{1}$H NMR (500 MHz, DMSO-$d_6$) δ 14.29 (s, 1H), 8.52 (s, 3H), 8.10-8.01 (m, 1H), 8.01-7.93 (m, 1H), 7.90 (s, 1H), 7.83 (dd, J=8.5, 2.0 Hz, 1H), 7.79 (dt, J=8.8, 2.4 Hz, 1H), 7.36 (d, J=8.6 Hz, 1H), 6.94 (d, J=4.6 Hz, 1H), 6.49 (d, J=4.4 Hz, 1H), 5.32 (s, 2H), 4.10 (d, J=5.6 Hz, 2H), 2.65 (s, 3H), 2.44 (s, 3H); $^{13}$C NMR (126 MHz, DMSO-$d_6$) δ 169.98, 164.79, 160.32, 156.15, 153.88, 142.80, 130.94, 129.19, 128.56, 126.44, 126.14, 123.17, 122.96, 120.01, 114.03, 112.93, 112.20, 101.47, 61.85, 37.13, 18.84, 11.76; HRMS calcd for $C_{22}H_{23}N_4O_2^+$: 375.1821; found, 375.1816.

7-(3-(Aminomethyl)-4-(thiazol-4-ylmethoxy)phenyl)-4-methylquinolin-2-amine Trihydrochloride (35). Compounds 39 (0.087 g, 0.282 mmol) and 114 (0.122 g, 0.304 mmol) were coupled using General Procedure 1. Purification by flash column chromatography, eluting with a gradient of 5% EtOAc in $CH_2Cl_2$ to 80% EtOAc in $CH_2Cl_2$, afforded protected phenylquinoline 133 as a cream-colored solid (0.056 g, 38%). A portion of this compound (0.047 g) was immediately deprotected using General Procedure 2. After workup, the free aminoquinoline was treated with methanolic HCl (2 mL), and sonicated for 10 minutes before stirring at room temperature for 18 h. The resulting grey precipitate was collected to afford 35 as a grey solid (0.044 g, 99% from 133) after filtering, washing with ether, and drying in vacuo. Because of the NMR spectral overlap of differing HCl species of 35, the precipitate was further purified using reverse phase chromatography, eluting through a 15.5 g C18 RediSep RF Gold cartridge column with a gradient of 100% water to 100% acetonitrile to afford 35 as a yellow solid (0.009 g, 38%) which was used for characterization: mp 210.8-212° C. (softens)>315° C. (dec); $^{1}$H-NMR (500 MHz, DMSO-$d_6$) δ 14.20 (s, 1H), 9.18 (d, J=1.9 Hz, 1H), 8.43 (s, 4H), 8.05 (d, J=8.5 Hz, 1 H), 7.94 (d, J=2.4 Hz, 1H), 7.92 (d, J=2.0 Hz, 1H), 7.89 (d, J=1.8 Hz, 1H), 7.84-7.75 (m, 2H), 7.42 (d, J=8.6 Hz, 1H), 6.91 (s, 1H), 5.42 (s, 2H), 4.12 (s, 2H), 2.64 (s, 3H); $^{13}$C-NMR (126 MHz, 500 MHz, DMSO-$d_6$) δ 156.45, 154.96, 154.03, 152.12, 151.95, 142.98, 136.00, 130.73, 129.20, 128.44, 126.18, 123.27, 123.18, 119.99, 118.35, 113.82, 113.36, 112.24, 65.99, 37.17, 18.97. HRMS calcd for $C_{21}H_{21}N_4OS^+$: 377.1436; found, 377.1429.

7-(3-(Aminomethyl)-4-(oxazol-4-ylmethoxy)phenyl)-4-methylquinolin-2-amine Trihydrochloride (36). Compounds 39 (0.089 g, 0.289 mmol) and 115 (0.133 g, 0.347 mmol) were coupled using General Procedure 1. Purification by flash column chromatography, eluting with a gradient of 5% EtOAc in $CH_2Cl_2$ to 80% EtOAc in $CH_2Cl_2$, afforded protected phenylquinoline 134 as a tan powder (0.027 g, 19%). A portion of this compound (0.024 g) was immediately deprotected using General Procedure 2. After workup, the free aminoquinoline was taken up in MeOH (1.0 mL) and treated with methanolic HCl (1.5 mL) for 18 h, and concentrated to dryness. The title compound (36) was obtained as a tan solid (0.014 g, 65% from 134) in 90% purity after recrystallizing once from 1:3 methanol-ethanol followed by an additional overnight recrystallization from methanol that was slowly diffused with ether, followed by removal of mother liquor, washing with 1:20 methanol-ether, and drying in vacuo. Additional purification of the crude product was achieved after reverse phase flash column chromatography, eluting through a 15.5 g C18 RediSep RF Gold cartridge column with a gradient of 100% water to 100% acetonitrile to afford pure 36 as a cream-colored solid (0.011 g, 47% from 135) after azeotropic removal of water with toluene and drying in vacuo: mp >151° C. (slowly browns) 253-254° C.). $^{1}$H-NMR (500 MHz, DMSO-$d_6$) δ 8.45 (s, 1H), 8.30 (s, 1H), 8.22-7.91 (m, 1H), 7.88 (d, J=2.5 Hz, 1H), 7.82 (d, J=8.4 Hz, 1H), 7.75 (dd, J=8.6, 2.5 Hz, 1H), 7.72 (d, J=1.9 Hz, 1H), 7.50 (dd, J=8.5, 2.1 Hz, 1H), 7.35 (dd, J=8.7, 2.8 Hz, 1H), 6.61 (s, 1H), 6.33 (s, 2H), 5.18 (s, 2H), 4.05 (s, 2H), the aminoquinoline-NH proton is broadened into baseline and the benzylic $CH_3$ protons are obscured by the solvent peak around 2.5; $^{13}$C NMR (126 MHz, DMSO-$d_6$) δ 158.23, 155.33, 152.46, 148.39, 143.80, 139.52, 137.92, 135.55, 132.62, 128.25, 127.67, 124.30, 123.67, 122.30, 121.93, 119.46, 113.05, 112.08, 62.21, 37.52, 18.08. HRMS calcd for $C_{21}H_{21}N_4O_2^+$: 361.1659; found, 361.1655.

7-(3-(Aminomethyl)-4-(thiazol-5-ylmethoxy)phenyl)-4-methylquinolin-2-amine Trihydrochloride (37). Compounds 39 (0.081 g, 0.265 mmol) and 116 (0.127 g, 0.32 mmol) were coupled using General Procedure 1. Purification by flash column chromatography, eluting with a gradient of 5% EtOAc in $CH_2Cl_2$ to 70% EtOAc in $CH_2Cl_2$, afforded protected phenylquinoline 135 as a tan solid (0.036 g, 26%). A portion of this compound (0.032 g) was immediately deprotected using General Procedure 2. After workup, the free aminoquinoline was taken up in MeOH (1.0 mL) and treated with methanolic HCl (1 mL) for 18 h, resulting in the formation of a white precipitate, which was concentrated to dryness. The pure title compound (37) was obtained as a brown crystalline solid (0.018 g, 60% from 135) after recrystallizing once from 1:5 methanol-ethanol and then from methanol, washing with 1:20 methanol-ether, and drying in vacuo: mp >238° C. (darkens) 252-255° C. (slowly softens)>256° C. (decomposes into brown foam). $^1$H NMR (500 MHz, DMSO-$d_6$) δ 14.33 (s, 1H), 9.18 (s, 1H), 8.54 (d, J=6.1 Hz, 3H), 8.12 (s, 1H), 8.06 (d, J=8.5 Hz, 1H), 7.98 (d, J=2.4 Hz, 1H), 7.90 (d, J=1.8 Hz, 1H), 7.84 (dd, J=8.6, 1.8 Hz, 1H), 7.79 (dd, J=8.6, 2.3 Hz, 1H), 7.42 (d, J=8.7 Hz, 1H), 6.96 (s, 1H), 5.57 (s, 2H), 4.06 (q, J=5.8 Hz, 3H), 2.65 (s, 4H); 13C NMR (126 MHz, DMSO) δ 155.94, 155.51, 153.86, 152.02, 142.93, 142.82, 135.97, 133.64, 130.85, 129.06, 128.42, 126.13, 123.18, 123.04, 119.97, 115.67, 113.86, 113.19, 112.18, 62.40, 37.04, 18.85; HRMS calcd for $C_{21}H_{21}N_4OS^+$: 377.1436 found, 377.1431.

Potassium 2-Acetamido-4-methylquinoline-7-trifluoroborate (39). Compound 38 (0.368 g, 1.32 mmol), $B_2Pin_2$ (0.503 g, 1.98 mmol), anhydrous KOAc (0.388 g, 3.96 mmol), and Pd(dppf)$Cl_2$ (5 mol %, 0.048 g) were combined in a sealable vial and diluted with anhydrous dioxane (5 mL). The mixture was purged with argon, sealed, and heated at 75° C. for 19 h. The mixture was then cooled, diluted with EtOAc (20 mL) and filtered through a pad of Celite overlaid with a thin layer of $SiO_2$. The pad was washed with EtOAc (200 mL), and the combined filtrate was washed with 5% aq. NaCl and sat. aq. NaCl (100 mL each). The organic layer was dried over anhydrous sodium sulfate and concentrated to yield a brown foam containing the crude 7-BPin quinoline, which was immediately diluted in THF/$H_2O$ (5 mL/1.5 mL). $KHF_2$ (0.412 g, 5.28 mmol) was added, and the mixture was stirred at r.t. for 3 h. THF (2 mL) and $H_2O$ (1 mL) were then added, and the mixture was sonicated vigorously for 5 min and concentrated. The residue was azeotroped three times with toluene, diluted with acetone, and filtered. The filter cake was extracted with boiling acetone (6×60 mL), and the combined acetone filtrates were concentrated. The residue was washed with 10% hexanes in $CH_2Cl_2$ to yield 39 as a light tan powder (0.371 g, 92%): mp >260° C. (darkens), 290-292° C. (dec). $^1$H-NMR (500 MHz; acetone-$d_6$): δ 9.33 (s, 1H), 8.12 (s, 1H), 7.91 (s, 1H), 7.71 (d, J=8.2 Hz, 1H), 7.66 (d, J=8.2 Hz, 1H), 2.63 (d, J=0.8 Hz, 3H), 2.23 (s, 3H); $^{13}$C-NMR (126 MHz; DMSO-$d_6$): δ 169.4, 150.2, 146.0, 145.1, 129.46, 129.45, 129.42, 123.9, 121.0, 112.7, 24.0, 18.7; this compound does not ionize well by ESI-MS or LC-TOF.

Purified NOS Enzyme Assays. Rat and human nNOS, rat nNOS mutants, murine macrophage iNOS, human iNOS, and human eNOS were recombinant enzymes (expressed in *E. coli* and purified as reported previously).[21,50-52] To test for NOS inhibition, the hemoglobin capture assay was used to measure nitric oxide production. The assay was performed at 37° C. in HEPES buffer (100 mM with 10% glycerol, pH 7.4) in the presence of 10 UM L-arginine, used because a) it is close to the $K_m$ values all three isoforms, where detection of competitive inhibitors is most sensitive, and b) significant NOS uncoupling does not occur at this concentration. Also included were 100 μM NADPH, 0.83 mM $CaCl_2$), approximately 320 units/mL of calmodulin, 10 μM $H_4B$, and human oxyhemoglobin (3 μM). For iNOS, the $CaCl_2$) and calmodulin were omitted and replaced with HEPES buffer (as neither are required for activation of iNOS). The assay was performed in 96-well plates using a Synergy 4 BioTek hybrid reader. The dispensing of NOS enzyme and hemoglobin was automated, and after 30 sec (maximum delay), NO production was read by monitoring the absorbance at 401 nm (resulting from the conversion of oxyhemoglobin to methemoglobin). Kinetic readouts were performed for 5 min. Each compound was assayed at least in duplicate, and six to nine concentrations (500 μM-50 nM or 100 μM-10 nM for eNOS and iNOS; 50 μM to 5 nM for rat and human nNOS) were used to construct concentration-response curves. $IC_{50}$ values were calculated by nonlinear regression (variable slope, four parameters) using GraphPad Prism software (standard error is reported for the Log$IC_{50}$), and $K_i$ values were obtained from $IC_{50}$ values using the Cheng-Prusoff 53 equation [$K_i=IC_{50}/(1+[S]/K_m)$] with the following $K_m$ values: 1.3 μM (rat nNOS), 1.6 μM (human nNOS), 8.2 μM (murine macrophage iNOS), 8 μM (human iNOS),[54] 3.9 μM (human eNOS),[55] 1.7 μM (rat nNOS D597N single mutant),[56] and 1.9 μM (rat nNOS D597N/M336V double mutant).

PAMPA-BBB Assay. The PAMPA-BBB assay was performed following a protocol described previously.[21] Briefly, the assay was performed in 10 mM phosphate-buffered saline (PBS) buffer (pH 7.5), and compounds were tested at a concentration of 200 μM. The donor plate was first coated with 4 μL of porcine brain lipid (20 mg/mL in dodecane), followed by addition of 250 μL of a test compound. The acceptor plate was filled with 250 μL of PBS, and the donor plate was carefully placed on top of the acceptor plate to make a "sandwich". The plate was incubated at 25° C. for 17 h in a saturated humidity atmosphere with orbital agitation at 100 rpm. Verapamil, chlorpromazine, and dopamine were used as a positive, intermediate, and negative control, respectively. After incubation, 150 μL of the test solution was taken from each well from both sides (donor and acceptor) and transferred to the UV plate for measurement. The effective permeability (Pe) was calculated using the following equation[57]

$$P_e = \frac{2.303}{A\times(t-\tau_{ss})}\times\frac{V_A\times V_D}{(V_A+V_D)}\times\lg\left[1-\left(\frac{V_A+V_D}{(1-R)\times V_D}\right)\times\left(\frac{C_A(t)}{C_D(0)}\right)\right]$$

where $P_e$ is the effective permeability (cm/s); $V_A$ and $V_D$ are the volumes of the acceptor and donor wells (0.25 $cm^3$), respectively; $C_A$ (t) is the concentration of the acceptor well at time t; $C_D$ (0) and $C_D$ (t) are the concentrations of the donor well at $t_0$ and t, respectively; A is the filter well area (0.21 $cm^2$); t is the incubation time(s); and $\tau_{ss}$ is the time to reach a steady state (usually very short compared to the incubation time). R is the retention membrane factor and was calculated using the following equation $$R = \left[1-\frac{C_D(t)}{C_D(0)}-\frac{V_A}{V_D}\times\frac{C_A(t)}{C_D(0)}\right]$$

$P_e$ was reported as an average of triplicate measurements with a standard deviation.

Human Liver Microsome Stability Assay. A 1120 μL aliquot of potassium phosphate buffer (50 mM, pH 7.4) containing liver microsomes (0.714 mg/mL) was added to individual 2 mL tubes (final concentration 0.5 mg/mL). Positive control (terfenadine) and 12 (1 mM DMSO stocks) were directly spiked into respective tubes to prepare a concentration of 1.428 μM (final concentration 1 μM). From the above mixture, 70 μL was added to individual wells of 96-well reaction plates and preincubated at 37° C. for 5 min. All reactions were initiated by adding 30 μL of 3.33 mM NADPH (1 mM final concentration). Reactions without NADPH and buffer controls (minus NADPH) at 0 min and 60 min were also incubated to rule out non-NADPH metabolism or chemical instability in the incubation buffer. All reactions were terminated using 100 μL of ice-cold acetonitrile containing an internal standard (glipizide) at 0, 5, 15, 30, and 60 min. The plates were centrifuged at 4000 rpm for 15 min, and 100 μL aliquots were analyzed for parent compound disappearance in the multiple-reaction monitoring (MRM) mode using liquid chromatography-mass spectrometry (LC-MS)/MS. The percent remaining of test compounds and positive controls in each sample was determined by considering the peak area ratio in the 0 minute sample as 100%. The half-life ($t_{1/2}$ in min) and the in vitro intrinsic clearance ($CL_{int}$ units in mL/min/kg) were calculated according to the following equations, where k is the gradient of line determined from a plot of the peak area ratio (compound peak area/internal standard peak area; plot can be found in FIG. 4) against time:

$$t_{1/2} = \frac{0.693}{k}; CL_{int} = \frac{0.693}{\text{in vitro } t_{1/2}} \times \frac{\text{mL incubation}}{\text{mg microsomes}} \times \frac{45\text{ mg microsomes}}{\text{gm liver}} \times \frac{20\text{ mg liver weight}}{\text{kg } b.w}$$

For liver microsomes, the scaling factor used was 45 mg of microsomal protein per gram liver.

Inhibitor Complex Crystal Preparation. The sitting drop vapor diffusion method was used to grow crystals at 4° C. for the heme domains of rnNOS (8 mg/mL containing 20 mM histidine), the hnNOS K301R/R354A/G357D mutant (10 mg/mL containing 20 mM histidine), and heNOS (6 mg/mL). The crystal growth conditions were as described previously. The only exception is that the pH for the heNOS crystal growth is 7.5 rather than 6.5 as mistakenly reported there. Fresh crystals were first passed stepwise through cryoprotectant solutions. The pH of the final soaking solution for mNOS was adjusted from 5.8 through 6.5, 7.0 (in MES) to 7.5 (in HEPES) and that for hnNOS from pH 7.2 to 7.5 (in HEPES), for heNOS the BIS-TRIS buffer at pH 7.5 was unchanged. At pH 7.5, crystals were soaked with 5-10 mM inhibitor for 2-4 h at 4° C. before being flash cooled with liquid nitrogen and stored until data collection.

X-ray Diffraction Data Collection, Data Processing, and Structural Refinement. The cryogenic (100 K) X-ray diffraction data were collected remotely at the Stanford Synchrotron Radiation Lightsource (SSRL) or Advanced Light Source (ALS) through the data collection control software Blu-Ice[58] and a crystal-mounting robot. When a CCD detector was used, 100-125° of data were typically collected with 0.5° per frame. If a Pilatus pixel array detector was used, 140-200° of fine-sliced data were collected with 0.2° per frame. More data frames were collected for heNOS which has a low symmetry ($P2_1$). Raw CCD data frames were indexed, integrated, and scaled using iMOSFLM,[59] but the pixel array data were preferably processed with XDS[60] and scaled with Aimless.[61] The binding of inhibitors was detected by initial difference Fourier maps calculated with REFMAC.[62] The inhibitor molecules were then modeled in Coot[63] and refined using REFMAC or PHENIX.[64] The symmetry of heNOS crystals was changed from the orthorhombic $P2_12_12_1$ reported previously[65] to monoclinic $P2_1$, with a β angle only 0.6-0.7° off compared to the original 90°. Therefore, a molecular replacement calculation with PHASER-MR[66] was needed to solve the structure. In the $P2_1$ space group, there are two heNOS dimers in the asymmetric unit. Disordering in portions of inhibitors bound in the NOS active sites was often observed, sometimes resulting in poor density quality. However, partial structural features were usually still visible if the contour level of the sigmaA weighted 2m|Fo|−D|Fc| map was dropped to 0.5 σ, which afforded the building of reasonable models into the disordered regions. Water molecules were added in PHENIX and visually checked by Coot. The TLS[67] protocol was implemented in the PHENIX refinements with each subunit as one TLS group. The omit Fo-Fc density maps were calculated by the Polder map facility in PHENIX for the bound inhibitors.[68] The refined structures were validated in Coot before deposition in the Protein Data Bank.

PDB ID Codes. PDB codes for X-ray crystal structures described in this study have been deposited in the Protein Data Bank under the following accession codes: 6PMV, 6PMW, 6PMX, 6PMY, 6PMZ, 6PN0, 6PN1, 6PN2, 6PN3, 6PN4, 6PN5, 6PN6, 6PN7, 6PN8, 6PN9, 6PNA, 6PNB, 6PNC, 6PND, 6PNE, 6PNF, 6PNG, 6PNH, 6PO5, 6PO7, 6PO8, 6PO9, 6POA, 6POB, 6POC, 6POT, 6POU, 6POV, 6POW, 6POX, 6POY, 6POZ, 6PP0, 6PP1, 6PP2, 6PP3, 6PP4.

REFERENCES (1) Torreilles, F.; Salman-Tabcheh, S.; Guérin, M.; Torreilles, J. Neurodegenerative disorders: the role of peroxynitrite. Brain Res. Rev. 1999, 30, 153-163.

(2) Uehara, T.; Nakamura, T.; Yao, D.; Shi, Z.; Gu, Z.; Ma, Y.; Masliah, E.; Nomura, Y.; Lipton, S. A. S-Nitrosylated proteindisulphide isomerase links protein misfolding to neurodegeneration. Nature 2006, 441, 513-517.

(3) Trippier, P. C.; Jansen Labby, K.; Hawker, D. D.; Mataka, J. J.; Silverman, R. B. Target- and mechanism-based therapeutics for neurodegenerative diseases: strength in numbers. J. Med. Chem. 2013, 56, 3121-3147.

(4) Campbell, M. G.; Smith, B. C.; Potter, C. S.; Carragher, B.; Marletta, M. A. Molecular architecture of mammalian nitric oxide synthase. Proc. Natl. Acad. Sci. U.S.A. 2014, 111, E3614-E3623.

(5) Gamboa, A.; Shibao, C.; Diedrich, A.; Choi, L.; Pohar, B.; Jordan, J.; Paranjape, S.; Farley, G.; Biaggioni, I. Contribution of endothelial nitric oxide to blood pressure in humans. Hypertension 2007, 49, 170-177.

(6) Cinelli, M. A.; Li, H.; Chreifi, G.; Martasek, P.; Roman, L. J.; Poulos, T. L.; Silverman, R. B. Simplified 2-aminoquinoline-based scaffold for potent and selective neuronal nitric oxide synthase inhibition. J. Med. Chem. 2014, 57, 1513-1530.

(7) Cinelli, M. A.; Li, H.; Pensa, A. V.; Kang, S.; Roman, L. J.; Martasek, P.; Poulos, T. L.; Silverman, R. B. Phenyl ether- and anilinecontaining 2-aminoquinolines as potent and selective inhibitors of neuronal nitric oxide synthase. J. Med. Chem. 2015, 58, 8694-8712.

(8) Cinelli, M. A.; Li, H.; Chreifi, G.; Poulos, T. L.; Silverman, R. B. Nitrile in the hole: discovery of a small auxiliary pocket in neuronal nitric oxide synthase leading to the development of potent and selective 2-aminoquinoline inhibitors. J. Med. Chem. 2017, 60, 3958-3978.

(9) Pensa, A. V.; Cinelli, M. A.; Li, H.; Chreifi, G.; Mukherjee, P.; Roman, L. J.; Martasek, P.; Poulos, T. L.; Silverman, R. B. Hydrophilic, potent, and selective 7-substituted 2-aminoquinolines as improved human neuronal nitric oxide synthase inhibitors. J. Med. Chem. 2017, 60, 7146-7165.

(10) Ballell, L.; Bates, R. H.; Young, R. J.; Alvarez-Gomez, D.; Alvarez-Ruiz, E.; Barroso, V.; Blanco, D.; Crespo, B.; Escribano, J.; González, R.; Lozano, S.; Huss, S.; Santos-Villarejo, A.; Martín-Plaza, J. J.; Mendoza, A.; Rebollo-Lopez, M. J.; Remuiñan-Blanco, M.; Lavandera, J. L.; Pérez-Herran, E.; Gamo-Benito, F. J.; García-Bustos, J. F.; Barros, D.; Castro, J. P.; Cammack, N. Fueling open-source drug discovery: 177 small-molecule leads against tuberculosis. ChemMed-Chem 2013, 8, 313-321.

(11) Mugumbate, G.; Abrahams, K. A.; Cox, J. A. G.; Papadatos, G.; van Westen, G.; Lelièvre, J.; Calus, S. T.; Loman, N. J.; Ballell, L.; Barros, D.; Overington, J. P.; Besra, G. S. Mycobacterial dihydrofolate reductase inhibitors identified using chemogenomic methods and in vitro validation. PLOS One 2015, 10, No. e0121492.

(12) Xue, F.; Li, H.; Fang, J.; Roman, L. J.; Martásek, P.; Poulos, T. L.; Silverman, R. B. Peripheral but crucial: A hydrophobic pocket (Tyr706, Leu337, and Met336) for potent and selective inhibition of neuronal nitric oxide synthase. Bioorg. Med. Chem. Lett. 2010, 20, 6258-6261.

(13) Duquenne, C.; Johnson, N.; Knight, S. D.; Lafrance, L.; Miller, W. H.; Newlander, K.; Romeril, S.; Rouse, M. B.; Tian, X.; Verma, S. K. Indazoles. WO2011140325A1, Nov. 10, 2011.

(14) Borg, G.; Cogan, D. A.; Ellman, J. A. One-pot asymmetric synthesis of tert-butanesulfinyl-protected amines from ketones by the in situ reduction of tert-butanesulfinyl ketimines. Tetrahedron Lett. 1999, 40, 6709-6712.

(15) Lind, K. E.; Cao, K.; Lin, E. Y—S.; Nguyen, T. B.; Tangonan, B. T.; Erlanson, D. A.; Guckian, K.; Simmons, R. C.; Lee, W—C.; Sun, L.; Hansen, S.; Pathan, N.; Zhang Pyridinonyl pdk1 Inhibitors. WO2008005457, Jan. 10, 2008.

(16) Heil, M.; Heilmann, E. K.; Sudau, A.; Kapferer, T.; Muhlthau, F. A.; Jeschke, P.; Voerste, R.; Gorgens, U.; Raming, K.; Ebbinghaus-Kinstscher, U.; Drewes, M.; Adamczewski, M.; Becker, A. Halogenalkyl-Substituted Amides Used as Insecticides and Acaricides. WO2011054436, Jul. 7, 2010.

(17) Brunton, S. A.; Guicherit, O. M.; Kruse, L. I.; Haydar, S. N.; Springer, D. M. Small Organic Molecule Regulators of Cell Proliferation. WO2008057469, May 15, 2008.

(18) Labby, K. J.; Xue, F.; Kraus, J. M.; Ji, H.; Mataka, J.; Li, H.; Martasek, P.; Roman, L. J.; Poulos, T. L.; Silverman, R. B. Intramolecular hydrogen bonding: A potential strategy for more bioavailable inhibitors of neuronal nitric oxide synthase. Bioorg. Med. Chem. 2012, 20, 2435-2443.

(19) Hevel, J. M.; Marletta, M. A. Nitric-oxide synthase assays. Methods Enzymol. 1994, 233, 250-258.

(20) Delker, S. L.; Xue, F.; Li, H.; Jamal, J.; Silverman, R. B.; Poulos, T. L. Role of zinc in isoform-selective inhibitor binding to neuronal nitric oxide synthase. Biochemistry 2010, 49, 10803-10810.

(21) Do, H. T.; Li, H.; Chreifi, G.; Poulos, T. L.; Silverman, R. B. Optimization of blood-brain barrier permeability with potent and selective human heuronal nitric oxide synthase inhibitors having a 2-aminopyridine scaffold. J. Med. Chem. 2019, 62, 2690-2707.

(22) The PyMOL Molecular Graphics System; version 1.8, Schrodinger, LLC.: 2015.

(23) Poulos, T. L.; Li, H. Structural basis for isoform-selective inhibition in nitric oxide synthase. Acc. Chem. Res. 2013, 46, 390-398.

(24) Huang, H.; Li, H.; Martasek, P.; Roman, L. J.; Poulos, T. J.; Silverman, R. B. Structure-guided design of selective inhibitors of neuronal nitric oxide synthase. J. Med. Chem. 2013, 56, 3024-3032.

(25) Delker, S. L.; Ji, H.; Li, H.; Jamal, J.; Fang, J.; Xue, F.; Silverman, R. B.; Poulos, T. L. Unexpected binding modes of nitric oxide synthase inhibitors effective in the prevention of cerebral palsy. J. Am. Chem. Soc. 2010, 132, 5437-5442.

(26) Mukherjee, P.; Li, H.; Sevrioukova, I.; Chreifi, G.; Martásek, P.; Roman, L. J.; Poulos, T. L.; Silverman, R. B. Novel 2,4-disubstituted pyrimidines as potent, selective, and cell-permeable inhibitors of neuronal nitric oxide Synthase. J. Med. Chem. 2015, 58, 1067-1088.

(27) Garcin, E. D.; Arvai, A. S.; Rosenfeld, R. J.; Kroeger, M. D.; Crane, B. R.; Andersson, G.; Andrews, G.; Hamley, P. J.; Mallinder, P. R.; Nicholls, D. J.; St-Gallay, S. A.; Tinker, A. C.; Gensmantel, N. P.; Mete, A.; Cheshire, D. R.; Connolly, S.; Stuehr, D. J.; Aberg, A.; Wallace, A. V.; Tainer, J. A.; Getzoff, E. D. Anchored plasticity opens doors for selective inhibitor design in nitric oxide synthase. Nat. Chem. Biol. 2008, 4, 700-707.

(28) Besnard, J.; Ruda, G. F.; Setola, V.; Abecassis, K.; Rodriguiz, R. M.; Huang, X.; Norval, S.; Sassano, M. F.; Shin, A. I.; Webster, L. A.; Simeons, F. R. C.; Stojanovski, L.; Prat, A.; Seidah, N. G.; Constam, D. B.; Bickerton, G. R.; Read, K. D.; Wetsel, W. C.; Gilbert, I. H.; Roth, B. L.; Hopkins, A. L. Automated design of ligands to polypharmacological profiles. Nature 2012, 492, 215-220.

(29) Basith, S.; Cui, M.; Macalino, S. J. Y.; Park, J.; Clavio, N. A. B.; Kang, S.; Choi, S. Exploring G-protein-coupled Receptors (GPCRs) ligand space via cheminformatics approaches: impact on rational drug design. Front. Pharmacol. 2018, 9, 128.

(30) Yanagisawa, I.; Hirata, Y.; Ishii, Y. Studies on histamine H2 receptor antagonists. 2. Synthesis and pharmacological activities of Nsulfamoyl and N-sulfonyl amidine derivatives. J. Med. Chem. 1987, 30, 1787-1793.

(31) Rankovic, Z. CNS drug design: balancing physicochemical properties for optimal brain exposure. J. Med. Chem. 2015, 58, 2584-2608.

(32) Di, L.; Kerns, E. H.; Fan, K.; McConnell, O. J.; Carter, G. T. High throughput artificial membrane permeability assay for blood-brain barrier. Eur. J. Med. Chem. 2003, 38, 223-232.

(33) Di, L.; Kerns, E. H.; Bezar, I. F.; Petusky, S. L.; Huang, Y. Comparison of blood-brain barrier permeability assays: in situ brain perfusion, MDR1-MDCKII and PAMPA-BBB. J. Pharm. Sci. 2009, 98, 1980-1991.

(34) Könczöl, Á.; Müller, J.; Földes, E.; Béni, Z.; Végh, K.; Kéry, Á.; Balogh, G. T. Applicability of a blood-brain barrier specific artificial membrane permeability assay at the early stage of natural productbased CNS drug discovery. J. Nat. Prod. 2013, 76, 655-663.

(35) Daina, A.; Michielin, O.; Zoete, V. SwissADME: a free web tool to evaluate pharmacokinetics, drug-likeness and medicinal chemistry friendliness of small molecules. Sci. Rep. 2017, 7, No. 42717.

(36) Daina, A.; Zoete, V. A BOILED-Egg to predict gastrointestinal absorption and brain penetration of small molecules. ChemMedChem 2016, 11, 1117-1121.

(37) Do, H. T.; Wang, H.-Y.; Li, H.; Chreifi, G.; Poulos, T. L.; Silverman, R. B. Improvement of Cell Permeability of Human Neuronal Nitric Oxide Synthase Inhibitors Using Potent and Selective 2-Aminopyridine-Based Scaffolds with a Fluorobenzene Linker. J. Med. Chem. 2017, 60, 9360-9375.
(38) Dialer, L. O.; Selivanova, S. V.; Muller, C. J.; Muller, A.; Stellfeld, T.; Graham, K.; Dinkelborg, L. M.; Kramer, S. D.; Schibli, R.; Reiher, M.; Ametamey, S. M. Studies toward the development of new silicon-containing building blocks for the direct (18) F-labeling of peptides. J. Med. Chem. 2013, 56, 7552-7563.
(39) Demont, E. H.; Garton, N. S.; Gosmini, R. L. M.; Hayhow, T. G. C.; Seal, J.; Wilson, D. M.; Woodrow, M. D. Tetrahydroquinoline Derivatives and their Pharmaceutical Use. WO2011054841, May 12, 2011.
(40) Günbaş, D. D.; Brouwer, A. M. Degenerate molecular shuttles with flexible and rigid spacers. J. Org. Chem. 2012, 77, 5724-5735.
(41) Brown, A. D.; Bunnage, M. E.; Glossop, P. A.; James, K.; Lane, C. A. L.; Lewthwaite, R. A.; Moses, I. A.; Price, D. A.; Thomson, N. M. Sulfonamide Derivatives for the Treatment of Diseases. US Patent US20100273758, Oct. 28, 2010.
(42) Jarboe, S. G.; Terrazas; Beak, P. The endocyclic restriction test: the geometries of nucleophilic substitutions at sulfur (VI) and sulfur (II). J. Org. Chem. 2008, 73, 9627-9632.
(43) Ballatore, C.; Soper, J. H.; Piscitelli, F.; James, M.; Huang, L.; Atasoylu, O.; Huryn, D. M.; Trojanowski, J. Q.; Lee, V. M.; Brunden, K. R.; Smith, A. B. Cyclopentane-1,3-dione: a novel isostere for the carboxylic acid functional group. Application to the design of potent thromboxane (A2) receptor antagonists. J. Med. Chem. 2011, 54, 6969-6983.
(44) Fisher, T. H.; Dershem, S. M.; Prewitt, M. L. Meta-substituent effects on benzyl free-radical stability. J. Org. Chem. 1990, 55, 1040-1043.
(45) Hoyt, S. B.; Petrilli, W. L.; London, C.; Xiong, Y.; Taylor, J. A.; Ali, A.; Lo, M.; Henderson, T. J.; Hu, Q.; Hartmann, R.; Yin, L.; Heim, R.; Bey, E.; Saxena, R.; Samanta, S. K.; Kulkarni, B. A. Aldosterone Synthase Inhibitors. WO2012148808, Nov. 1, 2012.
(46) Finkelstein, B. L.; Taggi, A. E.; Long, J. K.; Sharpe, P. L.; Tseng, C—P.; McCann, S. F.; Ding, A. X.; Swann, S. L., Jr. Substituted Benzene Fungicides. WO2008124092, Dec. 18, 2008.
(47) Nielsen, S. F.; Larsen, M.; Boesen, T.; Schonning, K.; Kromann, H. Cationic chalcone antibiotics. Design, synthesis, and mechanism of action. J. Med. Chem. 2005, 48, 2667-2677.
(48) Andreini, M.; Gabellieri, E.; Guba, W.; Marconi, G.;_Narquizian, R.; Power, E.; Travagli, M.; Woltering, T.; Wostl, W. 4,5-Dihydro-oxazol-2-yl Amine Derivatives. US Patent US10090209529, Aug. 20, 2009.
(49) Molander, G. A.; Trice, S. L. J.; Kennedy, S. M. Scope of the two-step, one-pot palladium-catalyzed borylation/suzuki cross-coupling reaction utilizing bis-boronic acid. J. Org. Chem. 2012, 77, 8678-8688.
(50) Roman, L. J.; Sheta, E. A.; Martásek, P.; Gross, S. S.; Liu, Q.; Masters, B. S. S. High-level expression of functional rat neuronal nitric oxide synthase in *Escherichia coli*. Proc. Natl. Acad. Sci. U.S.A. 1995, 92, 8428-8432.
(51) Hevel, J. M.; White, K. A.; Marletta, M. A. Purification of the inducible murine macrophage nitric oxide synthase: identification as a flavoprotein. J. Biol. Chem. 1991, 266, 22789-22791.
(52) Gerber, N. C.; Ortiz de Montellano, P. R. Neuronal nitric oxide synthase: expression in *Escherichia coli*, irreversible inhibition by phenyldiazene, and active site topology. J. Biol. Chem. 1995, 270, 17791-17796.
(53) Yung-Chi, C.; Prusoff, W. H. Relationship between the inhibition constant ($K_i$) and the concentration of the inhibitor which causes 50 percent inhibition (IC50) of an enzymatic reaction. Biochem. Pharmacol. 1973, 22, 3099-3108.
(54) Fossetta, J. D.; Niu, X. D.; Lunn, C. A.; Zavodny, P. J.; Narula, S. K.; Lundell, D. Expression of human inducible nitric oxide synthase in *Escherichia coli*. FEBS Lett. 1996, 379, 135-138.
(55) Leber, A.; Hemmens, B.; Klosch, B.; Goessler, W.; Raber, G.; Mayer, B.; Schmidt, K. Characterization of recombinant human endothelial nitric-oxide synthase purified from the yeast *Pichia pastoris*. J. Biol. Chem. 1999, 274, 37658-37665.
(56) Li, H.; Wang, H. Y.; Kang, S.; Silverman, R. B.; Poulos, T. L. Electrostatic control of isoform selective inhibitor binding in nitric oxide synthase. Biochemistry 2016, 55, 3702-3707.
(57) Müller, J.; Essõ, K.; Dargo', G.; Könczöl, A.; Balogh, G. T. Tuning the predictive capacity of the PAMPA-BBB model. Eur. J. Pharm. Sci. 2015, 79, 53-60.
(58) McPhillips, T. M.; McPhillips, S. E.; Chiu, H.-J.; Cohen, A. E.; Deacon, A. M.; Ellis, P. J.; Garman, E.; Gonzalez, A.; Sauter, N. K.; Phizackerley, R. P.; Soltis, S. M.; Kuhn, P. Blu-Ice and the Distributed Control System: software for data acquisition and instrument control at macromolecular crystallography beamlines. J. Synchrotron Radiat. 2002, 9, 401-406.
(59) Battye, T. G. G.; Kontogiannis, L.; Johnson, O.; Powell, H. R.; Leslie, A. G. W. iMOSFLM: a new graphical interface for diffractionimage processing with MOSFLM. Acta Crystallogr., Sect. D: Biol. Crystallogr. 2011, 67, 271-281.
(60) Kabsch, W. XDS. Acta Crystallogr., Sect. D: Biol. Crystallogr. 2010, 66, 125-132.
(61) Evans, P. Scaling and assessment of data quality. Acta Crystallogr., Sect. D: Biol. Crystallogr. 2006, 62, 72-82.
(62) Murshudov, G. N.; Vagin, A. A.; Dodson, E. J. Refinement of macromolecular structures by the maximum-likelihood method. Acta Crystallogr., Sect. D: Biol. Crystallogr. 1997, 53, 240-255. (63) Emsley, P.; Cowtan, K. Coot: model-building tools for molecular graphics. Acta Crystallogr., Sect. D: Biol. Crystallogr. 2004, 60, 2126-2132.
(64) Adams, P. D.; Afonine, P. V.; Bunkoczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. PHENIX: a comprehensive Python-based system for macromolecular structure solution. Acta Crystallogr., Sect. D: Biol. Crystallogr. 2010, 66, 213-221.
(65) Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. Acta Crystallogr., Sect. D: Biol. Crystallogr. 2014, 70, 2667-2674.
(66) McCoy, A. J.; Grosse-Kunstleve, R. W.; Adams, P. D.; Winn, M. D.; Storoni, L. C.; Read, R. J. Phaser crystallographic software. J. Appl._Crystallogr. 2007, 40, 658-674.
(67) Winn, M. D.; Isupov, M. N.; Murshudov, G. N. Use of TLS parameters to model anisotropic displacements in macromolecular refinement. Acta Crystallogr., Sect. D: Biol. Crystallogr. 2001, 57, 122-133.

(68) Liebschner, D.; Afonine, P. V.; Moriarty, N. W.; Poon, B. K.; Sobolev, O. V.; Terwilliger, T. C.; Adams, P. D. Polder maps: improving OMIT maps by excluding bulk solvent. Acta Crystallogr., Sect. D: Biol. Crystallogr . . . 2017, 73, 148-157.

Example 2—Supporting Information for Example 1

Results and Discussion

Molecular Docking Protocol. Molecular models of 20, 22, 23, 24 and 30 were developed using the Molecular Operating Environment (MOE) computational suite's Builder utility followed by minimization in the gas phase using the MMFF94X1 force field. The X-ray crystal structure of compound 12 bound to rat nNOS was then uploaded into MOE and prepared for docking using MOE's Structure Preparation utility. The hydrogen-bonding network of the docking model was further optimized at pH 7.4 by automatically sampling different tautomer/protomer states using Protonate3D, which calculates optimal protonation states, including titration, rotamer, and "flips" using a large-scale combinatorial search. The heme binding pocket of chain A was surveyed using MOE's Site Finder utility and populated with inactivate dummy atoms that define the docking location. Following the preparation of the mNOS docking model and inactivation of the atoms of 12, molecular docking using the previously generated ligand conformation database was carried out at the docking site specified by the dummy atoms populating the binding pocket of chain A of the docking receptor. Ligand placement employed the Alpha Triangle method with Affinity dG scoring to generate 100 data points per unique ligand, which were further refined using the Induced Fit method with GBVI/WSA2 dG scoring to obtain the top 50 docking poses per ligand. The Amber12: EHT3 force field was used to perform these calculations. The top ligand docking pose was then imported into the docking rnNOS structure and overlaid with the original atoms of compound 12 to show a range of substituents capable of being accommodated at position 4 of the phenyl ring (data not shown).

Constrained Amine Analogues 16-18. The fact that both 5 and 10 can interfere with the aspartate site encouraged the preparation of isoindoline compound 16, which can be thought of as a conformationally constrained hybrid of both 5 and 10. However, at 254 nM, 16 is considerably less potent than either 5 or 10, which suggests that either (a) the flexibility of the aminomethyl group is explicitly needed for effective binding or (b) the extra methylene added to constrain the amine is detrimental to binding. This observation of reduced flexibility correlating with lower potency is also noted for 17 and 18. Compound 17, a constrained version of 7, was assayed against rnNOS and was found to be approximately 3-fold less potent than the parent molecule. Similarly, 18, another constrained derivative of 12, is also about 3-fold less potent.

Small 4-Alkyloxy-3-aminomethyl Analogues 25-28. Further extending the 4-position alkyloxyl substituent in 25-27 with a longer or branched alkyl chain resulted in similar potency against rnNOS compared to 12. The alkyloxyl moiety should approach the shallow hydrophobic pocket made by Met336, Leu337, and Tyr706. Also, compounds 24, 25, and 26 retain most of the isoform selectivity (24, rn/mi=418, hn/he=164; 25, rn/mi=333, hn/he=223; 26, rn/mi=360, hn/he=307), while increased binding affinities of 27 with miNOS and heNOS substantially reduces isoform selectivity (rn/mi=156, hn/he=78).

Based on our X-ray crystal structure analysis, 25 was observed to bind to rnNOS with its n-propyloxyl moiety pointing to the aforementioned hydrophobic pocket (data not shown). However, the position of the aminomethyl moiety of 25 is ambiguous with weak density. It is likely pointing toward Asn569 instead of interacting with heme propionate A as in the case for 24 (data not shown). Whereas in heNOS, 25 clearly binds with its aminomethyl moiety H-bonded to heme propionate A (data not shown). The good non-bonded contact from the n-propyloxyl tail to the bulky Phe105 stabilizes the binding. In the rnNOS-26 structure (data not shown), the central phenyl ring of 26 presses on the heme propionate D, forcing it into a downward conformation and allowing the aminomethyl group to directly H-bond with the propionate and Tyr706. The i-propyloxyl tail is not that close to the hydrophobic pocket. In the heNOS-26 structure (data not shown) the i-propyloxyl tail makes good contact with Phe105, and the aminomethyl group forms a good H-bond with the heme propionate A. Moreover, in one subunit of each dimer there is a second molecule of 26 bound in the pterin site via a stacking interaction between the aminoquinoline of 26 and the Trp447 side chain. However, the H4B in the other subunit is not displaced.

On the other hand, the hnNOS binding affinities of 25-27 show a slight decline in potency. This was thought to be the result of an increased repulsion of the 4-position alkyl group as the hydrophobic moieties approach the human nNOS-specific residue, His342.5 Unexpectedly, in each subunit there are two molecules of inhibitors bound in both the active site and the pterin site as shown in the crystal structures of 25 and 26 bound to hnNOS (data not shown). The aminomethyl moiety of 25 or 26 makes a H-bond with Asn574. The n-propyl group of 25 or i-propyl of 26 allows for interactions with hydrophobic residue Met341 but is far from His342. Both show superior binding affinity to hnNOS (25, Ki (hnNOS)=58 nM; 26, Ki (hnNOS)=66 nM). By virtue of their improved hnNOS inhibition, 25 and 26 also have improved hnNOS/heNOS selectivity (25; hn/he=333) relative to 24, while a loss in potency against human nNOS for 27 ($K_i$ (hnNOS)=72 nM) in conjunction with improved heNOS binding ($K_i$ (hnNOS)=5.65 μM) contributes to a substantial drop in n/e selectivity (hn/he=78).

The binding of a second inhibitor molecule in the pterin site results in some substantial and unexpected changes in structure. The quinoline ring of 25 or 26 in the pterin site is sandwiched between Trp683 and Phe696. The aminoquinoline also forms an extensive hydrogen-bonding network between the backbone carbonyl of Val682 and with heme propionate A through two additional water molecules. Most notably, displacement of H4B by 25 or 26 results in the loss of the H-bond between H4B and Arg601, leading to disordering of the protein backbone containing residues 598-611 (data not shown). The original helical structure (598-605) is disrupted and replaced by a small 310 helix (600-602) followed by a β-hairpin like surface loop (603-611). Dual inhibitor binding was also observed for 26 in heNOS (data not shown), and has been observed in the past,[6] where it often created an additional Zn binding site; however, there was no protein backbone distortion found in heNOS. The exact reason for this pterin site disruption-triggered protein backbone secondary structural changes in hnNOS remains to be explored.

Examination of the 1.80 Å resolution crystal structure of 28 bound to rnNOS (data not shown) showed that the cyclobutane ring has van der Waals interactions in the Met336-Leu337-Tyr706 pocket, allowing the aminomethyl group to form H-bonds with both Tyr706 and heme propionate D. This new position of the aminomethyl moiety of 28, along with the hydrophobic interactions with Met336, Leu337, and Tyr706, led to good potency against mNOS ($K_i$ (mNOS)=49 nM). Compound 28 binds somewhat differently in hnNOS. We observed that the tail cyclobutyl ring of 28 rotates "up" relative to how 28 binds in rnNOS, which is because of the repulsion from the more polar residue His342 (vs. Leu337 in rnNOS) (data not shown). The aminomethyl group points toward Asn574. It seems likely that the better nonpolar contacts provided by Met336/Leu337 in mNOS accounts for the difference in inhibitor binding and, possibly, the slightly better binding affinity to mNOS (Table 1). In heNOS, the cyclobutane of 28 is positioned similar to rnNOS (data not shown), where it can interact with Phe105 in heNOS. However, the central phenyl ring flips 1800 relative to mnNOS so that the aminomethyl group can interact with heme propionate A rather than heme propionate D as in rnNOS.

Unusual binding behavior of 31. Examination of the hnNOS-31 structure showed that 31 binds to human nNOS with high variability (data not shown), suggesting less than an optimal binding conformation. The available electron density is strongest at the aminoquinoline position but dissipates when moving toward the central and tail phenyl groups. The middle phenyl ring sits vertically between the heme propionates allowing the amine group to hydrogen bond with Gln483. The cyano group of the tail phenyl ring possibly approaches Trp311 (from the other chain). Even more puzzling is that we have failed to obtain good rnNOS X-ray data with 31 bound. On the other hand, the binding of 31 was found to be more ordered in the heNOS-31 structure (data not shown). The aminomethyl moiety points toward Glu361. The conformation of the tail phenyl is somewhat uncertain, but a piece of electron density is present next to His371, suggesting that the cyano group of the tail phenyl ring can interact with His371, which may explain the rather tight binding (8.3 μM) of 31 to heNOS.

Structural features of 36 and 37. In the rnNOS-36 structure, the aminomethyl moiety of the central phenyl ring was found to point to Gln478 (data not shown). The tail oxazole ring sits in the pocket of Met336, Leu337, and Tyr706, with its ring nitrogen pointing toward Tyr706. Binding of 36 to hnNOS is unusual (data not shown) because there are two molecules of 36 in each subunit. Instead of approaching the hydrophobic pocket made up by Met341, His342, and Tyr711, the tail oxazole ring of 36 bends over to reach the second inhibitor bound in the pterin site, stacking with the central benzene ring of that inhibitor. The disturbance of the protein backbone (residues 598-611, as discussed above) also occurs here, but it is not as severe as in the cases of hnNOS-25 or hnNOS-26. The backbone was finally modeled as a mixture of two alternate conformations.

Crystal structures of 37 bound to rat and human nNOS reveal strong densities for both the aminoquinoline and the middle phenyl rings, and weaker densities at the tail aminomethyl group and thiazole ring (data not shown). The orientation preference of the phenyl ring observed for 35 is repeated for 37 in two nNOS species, with the aminomethyl group pointing toward Gln478 in the rnNOS structure and toward Asn574 in the hnNOS structure. Although the orientation of the thiazole ring is almost identical in the two structures, the bulkier His342 of human nNOS slightly pushes the tail thiazole ring of 37 away relative to the position seen in the rat enzyme. The binding mode of 35 and 37 to hnNOS is worth more attention in future SAR studies because it provides better potency against human NOS than it does for rat nNOS.

SI Experimental Section.

tert-Butyl (4-iodobenzyl)(methyl)carbamate (46). NaH (0.100 g, 2.5 mmol of a 60% dispersion in mineral oil) was diluted with anhydrous THF (5 mL) under argon. Compound 45 (0.333 g, 1 mmol) was added as a solution in minimal THF, and the mixture was stirred at r.t. for 20 min. MeI (0.354 g, 0.155 mL, 2.5 mmol) was added, and the mixture was stirred at r.t. for 18 h and then quenched by the addition of sat. aq. $NaHCO_3$ (10 mL). The mixture was extracted with EtOAc (3×20 mL), and the organic layer was washed with $H_2O$ and sat. aq. NaCl (30 mL each), dried over anhydrous sodium sulfate, and concentrated. The residue was passed through a short $SiO_2$ plug, eluting with hexanes and then with EtOAc, and the latter fraction was concentrated and dried in vacuo to afford 46 as a clear, colorless syrup that was used in the next step without further characterization (0.341 g, 98%). $^1$H-NMR (500 MHz; $CDCl_3$): δ 7.65 (d, J=8.2 Hz, 2H), 6.97 (br s, 2H), 4.35 (s, 2H), 2.80 (2 s, 3H), 1.46 (s, 9H).

(S,S)—N—(-1-(4-Bromophenyl) propan-2-yl)-2-methylpropane-2-sulfinamide (48). Ketone 47 (0.426 g, 2.00 mmol) was diluted in anhydrous THF (10 mL) and Ti (OEt) 4 (1.048 mL, 4 mmol) was added, followed by(S)-t-butanesulfinamide (0.242 g, 2.00 mmol), as a solution in 2 mL anhydrous THF. The reaction mixture was heated to 70° C. for 3 h, and was cooled to r.t. and then to 0° C. This solution was added dropwise to a stirring suspension of NaBH4 (0.304 g, 8.00 mmol) in anhydrous THF (10 mL) at −48° C. After 45 min at −48° C., the reaction was quenched by addition of MeOH until gas evolution ceased. The mixture was then warmed to r.t. and an equal volume of sat. aq. NaCl was added to precipitate titanium salts. After stirring for 5 min, the suspension was filtered through Celite and the filter cake was washed with EtOAc (100 mL). The organic layers were separated, and the aqueous layer was extracted with EtOAc (2×40 mL). The combined organic layers were dried over anhydrous sodium sulfate, and concentrated to yield a residue that was purified by flash column chromatography, eluting with a gradient of 30% EtOAc in hexanes to 85% EtOAc in hexanes, to afford the title compound (major diastereomer) as a colorless, clear syrup (0.354 g, 56%) that solidified upon standing. The compound was used crude in the next step without further purification. $^1$H-NMR (500 MHz; $CDCl_3$): δ 7.45-7.42 (m, 2H), 7.11-7.08 (m, 2H), 3.65 (qd, J=6.4, 5.4 Hz, 1H), 3.13 (d, J=5.1 Hz, 1H), 2.81 (d, J=6.5 Hz, 2H), 1.17-1.15 (m, 12H).

tert-Butyl(S)-(1-(4-bromophenyl) propan-2-yl) carbamate (49). Compound 48 (0.349 g, 1.10 mmol) was diluted in ether, and methanolic HCl (3 M, 2 mL, 6 mmol) was added. The mixture was stirred at r.t. for 1 h and concentrated. Ether (10 mL) was added to precipitate a white crystalline solid that was collected and diluted in minimal MeOH (2 mL). $Et_3N$ (0.142 mL, 1.1 mmol) was added, and after 5 min, the mixture was diluted with anhydrous THF (10 mL). $Boc_2O$ (0.217 g, 1.02 mmol) was then added as a solution in anhydrous THF (3 mL). The mixture was stirred at r.t. for 90 min and concentrated, and the residue was extracted 3× with boiling 20% EtOAc in hexanes (20 mL). Concentration afforded a residue that was purified by flash column chromatography, eluting with a gradient of 3% EtOAc in hexanes to 15% EtOAc in hexanes, to yield the title compound as a white wax ((0.281 g, 81% from (48)). The spectral data for this compound are consistent with those previously reported.9 $^1$H-NMR (500 MHz; $CDCl_3$): δ 7.42-7.40 (m, 2H), 7.05 (d, J=8.3 Hz, 2H), 4.34 (br s, 1H), 3.87 (br s, 1H), 2.81-2.77 (m, 1H), 2.62 (dd, J=13.4, 7.3 Hz, 1H), 1.42 (s, 9H), 1.07 (d, J=6.7 Hz, 3H).

tert-Butyl (3-bromo-5-cyanobenzyl) carbamate (67). NaH (0.061 g, 1.45 mmol of a 60% dispersion) was diluted in anhydrous THF (4 mL) under argon. A solution of Boc2NH (0.175 g, 0.806 mmol) was added in minimal THF, and the mixture was stirred at r.t. for 30 min before a solution of 66 (0.200 g, 0.732 mmol) in THF (2 mL) was added. The mixture was stirred overnight and quenched by the addition of sat. aq. NaHCO3 (20 mL). The mixture was extracted with EtOAc (3×20 mL), and the organic phase was washed with 5% aq. NaCl and sat. aq. NaCl (20 mL each), dried over anhydrous sodium sulfate, and concentrated. The residue was purified by flash column chromatography, eluting with a gradient of hexanes to 25% EtOAc in hexanes, to yield a clear syrup that was crystallized from hexanes to afford 67 as a white powder (mostly the mono-Boc protected amine), which was immediately used without further characterization or purification. $^{1}$H-NMR (500 MHz; $CDCl_3$): δ 7.68 (s, 1H), 7.66 (s, 1H), 7.51 (s, 1H), 4.96 (br s, 1H), 4.33 (br d, J=5.7 Hz, 2H), 1.47 (s, 9H).

tert-Butyl 4-bromoisoindoline-2-carboxylate (73). Compound 72 (0.234 g, 1.00 mmol) was diluted in MeOH (2 mL). $Et_3N$ (0.153 mL, 1.1 mmol) was added, and the mixture was heated gently to affect solution. After 5 min, THF (10 mL) was added, followed by $Boc_2O$ (0.218 g, 1.00 mmol) in THF (3 mL). The mixture was stirred at r.t. for 18 h and concentrated. The residue was partitioned between EtOAc and $H_2O$ (30 mL each). The phases were separated, and the aqueous layer was extracted with EtOAc (20 mL). The organic layers were washed with $H_2O$ (2×30 mL) and sat. aq. NaCl (30 mL), dried over anhydrous sodium sulfate, and concentrated to yield 73 as a white waxy solid (0.298 g, quant.) after drying in vacuo: mp 92.5-93° C. $^{1}$H-NMR (500 MHz; $CDCl_3$): δ 7.40 (d, J=8.2 Hz, 1H), 7.21-7.14 (m, 2H), 4.75 (d, J=19.7 Hz, 2H), 4.64 (d, J=30.8 Hz, 2H), 1.52 (2 s, 9H); $^{13}$C-NMR (126 MHz; $CDCl_3$, shows a mixture of rotameric states): δ (154.36+154.30, 1 C), (139.1+138.8, 1 C), (138.12+137.93, 1 C), (130.37+130.32, 1 C), (129.23+129.16, 1 C), (121.6+121.3, 1 C), (117.7+117.4, 1 C), (80.06+79.95, 1 C), (53.59+53.50, 1 C), (53.2+53.0, 1 C), (28.56+28.53, 3 C); LC-TOF ESI m/z 320/322 (MNa+).

(±)—N-(5-Bromo-2,3-dihydro-1H-inden-1-yl)-2-methylpropane-2-sulfinamide (77). Ketone 75 (0.422 g, 2.00 mmol) was diluted in anhydrous THF (10 mL) and Ti(OEt)4 (1.048 mL, 4 mmol) was added, followed by (RS)-t-butanesulfinamide (0.242 g, 2.00 mmol), as a solution in 2 mL of anhydrous THF. The reaction mixture (a suspension) was heated to 70° C. for 3 h, and was cooled to r.t. and then to −48° C. $NaBH_4$ (0.304 g, 8.00 mmol) was added in one portion. After 40 min at −48° C., the reaction was quenched by addition of MeOH until gas evolution ceased. The mixture was then warmed to r.t. and an equal volume of sat. aq. NaCl was added to precipitate titanium salts. After stirring for 5 min, the suspension was filtered through Celite and the filter cake was washed with EtOAc (100 mL). The organic layers were separated, and the aqueous layer was extracted with EtOAc (2×40 mL). The combined organic layers were dried over anhydrous sodium sulfate, and concentrated to yield a residue that was purified by flash column chromatography, eluting with a gradient of hexanes to 50% EtOAc in hexanes, to afford the title compound (presumably the RR and SS diasteromers) as a white wax (0.103 g, 16%). The compound was used immediately in the next step without further characterization. $^{1}$H-NMR (500 MHz; $CDCl_3$): δ 7.45 (d, J=8.0 Hz, 1H), 7.37-7.34 (m, 2H), 4.84 (q, J=6.9 Hz, 1H), 3.40 (d, J=6.3 Hz, 1H), 2.97 (ddd, J=16.0, 8.5, 4.4 Hz, 1H), 2.81 (dt, J=16.0, 7.9 Hz, 1H), 2.52-2.45 (m, 1H), 2.04-1.96 (m, 1H), 1.23 (s, 9H).

(±)—N-(6-Bromo-2,3-dihydro-1H-inden-1-yl)-2-methylpropane-2-sulfinamide (78). Ketone 76 (0.422 g, 2.00 mmol) was diluted in anhydrous THF (10 mL) and Ti(OEt)4 (1.048 mL, 4 mmol) was added, followed by (RS)-t-butanesulfinamide (0.282 g, 2.52 mmol), as a solution in 2 mL anhydrous THF. The reaction mixture (a suspension) was heated to 70° C. for 3 h, and was cooled to r.t. and then to −48° C. $NaBH_4$ (0.304 g, 8.00 mmol) was added in one portion. After 50 min at −48° C., the reaction was quenched by addition of MeOH until gas evolution ceased. The mixture was then warmed to r.t. and an equal volume of sat. aq. NaCl was added to precipitate titanium salts. After stirring for 5 min, the suspension was filtered through Celite, and the filter cake was washed with EtOAc (100 mL). The organic layers were separated, and the aqueous layer was extracted with EtOAc (2×40 mL). The combined organic layers were dried over anhydrous sodium sulfate, and concentrated to yield a residue that was purified by flash column chromatography, eluting with a gradient of hexanes to 50% EtOAc in hexanes, to afford the title compound (presumably the RR and SS diasteromers) as a white wax (0.157 g, 25%). The compound used immediately in the next step without further characterization. $^{1}$H-NMR (500 MHz; $CDCl_3$): δ 7.69 (s, 1H), 7.36 (d, J=8.0 Hz, 1H), 7.10 (d, J=8.0 Hz, 1H), 4.88 (q, J=6.9 Hz, 1 H), 3.44 (d, J=6.1 Hz, 1H), 2.93 (ddd, J=15.1, 9.2, 5.0 Hz, 1H), 2.76 (dt, J=16.0, 7.9 Hz, 1 H), 2.51-2.45 (m, 1H), 2.01 (dq, J=13.7, 7.0 Hz, 1H), 1.24 (s, 9H).

(±)-tert-Butyl (5-Bromo-2,3-dihydro-1H-inden-1-yl) carbamate (79).10 Compound 77 (0.103 g, 0.325 mmol) was diluted in 2:1 ether/MeOH (15 mL), and methanolic HCl (3 M, 1.5 mL, 1.5 mmol) was added. The mixture was stirred at r.t. for 18 h and concentrated. The residue was diluted in MeOH (1.5 mL). $Et_3N$ (0.090 mL, 0.650 mmol) was added, and after 5 min, the mixture was diluted with anhydrous THF (10 mL). $Boc_2O$ (0.074 g, 0.341 mmol) was then added as a solution in anhydrous THF (2 mL). The mixture was stirred at r.t. for 2 h and concentrated. The residue was partitioned between EtOAc and $H_2O$ (20 mL each). The layers were separated, and the aqueous layer was extracted with EtOAc (2×20 mL), and the combined organic layers were washed with $H_2O$ and sat. aq. NaCl (30 mL) and dried over anhydrous sodium sulfate. Concentration afforded a residue that was purified by flash column chromatography, eluting with a gradient of hexanes to 20% EtOAc in hexanes to yield 79 as a white waxy solid (0.095 g, 94%) after drying in vacuo: mp 103-103.5° C. $^{1}$H-NMR (500 MHz; $CDCl_3$): δ 7.36 (s, 1H), 7.33 (d, J=8.1 Hz, 1H), 7.19 (d, J=8.0 Hz, 1H), 5.15-5.10 (br m, 1H), 4.70-4.67 (br m, 1H), 2.93 (ddd, J=16.2, 8.8, 3.6 Hz, 1H), 2.85-2.79 (m, 1H), 2.60-2.53 (m, 1H), 1.83-1.75 (m, 1H); $^{13}$C-NMR (126 MHz; $CDCl_3$): δ 155.6, 145.5, 142.7, 129.8, 127.9, 125.6, 121.7, 79.6, 55.5, 34.4, 29.9, 28.4 (3 C); LC-TOF ESI m/z 334/336 (MNa+).

(±)-tert-Butyl (6-bromo-2,3-dihydro-1H-inden-1-yl) carbamate (80). Compound 78 (0.157 g, 0.0.497 mmol) was diluted in 2:1 ether/MeOH (10 mL), and methanolic HCl (3 M, 1.5 mL, 1.5 mmol) was added. The mixture was stirred at r.t. for 18 h, concentrated, and azeotroped twice with toluene. The residue was diluted in MeOH (3 mL). $Et_3N$ (0.139 mL, 1.00 mmol) was added, and after 5 min, the mixture was diluted with anhydrous THF (10 mL). $Boc_2O$ (0.108 g, 0.497 mmol) was then added as a solution in anhydrous THF (2 mL). The mixture was stirred at r.t. for 2 h and concentrated. The residue was partitioned between EtOAc and $H_2O$ (20 mL each). The layers were separated, and the aqueous layer was extracted with EtOAc (2×20 mL), and the combined organic layers were washed with $H_2O$ and sat. aq. NaCl (30 mL), and dried over anhydrous sodium sulfate. Concentration afforded a residue that was purified by flash column chromatography, eluting with a gradient of hexanes to 20% EtOAc in hexanes to yield 80 as a white waxy solid (0.147 g, 95%) after drying in vacuo. mp 101-102° C. $^{1}$H-NMR (500 MHz; $CDCl_3$): δ 7.44 (s, 1H), 7.33 (dd, J=8.0, 1.1 Hz, 1H), 7.08 (d, J=8.0 Hz, 1H), 5.18-5.17 (m, 1 H), 4.72-4.69 (m, 1H), 2.89 (ddd, J=16.0, 8.8, 3.3 Hz, 1H), 2.80-2.73 (m, 1H), 2.60-2.54 (m, 1 H), 1.82-1.75 (m, 1H), 1.49 (s, 9H); $^{13}$C-NMR (126 MHz; $CDCl_3$): δ 155.6, 146.1, 142.1, 130.8, 127.2, 126.3, 120.3, 79.7, 55.8, 34.6, 29.7, 28.4 (3 C); LC-TOF ESI m/z 334/336 (MNa+).

2-(Bromomethyl)-1-fluoro-4-iodobenzene (85). Compound 83 (0.708 g, 3.00 mmol) was diluted in $CCl_4$ (30 mL). NBS (0.561 g, 3.15 mmol) was added, followed by $(PhCO_2)_2$ (~20 mg). The mixture was heated at reflux for 18 h, cooled, and diluted with hexanes (20 mL). The insoluble precipitate was filtered, and the filtrate was concentrated. The residue was purified by flash column chromatography, eluting with hexanes.

Fractions containing 85 were concentrated and re-purified by column chromatography using the same eluent, and pure 85 (0.455 g, 48%) was obtained as a clear, colorless oil, >90% pure by NMR spectroscopy and suitable for use in the next step without further purification. 1H-NMR (500 MHz; $CDCl_3$): δ 7.70 (dd, J=6.9, 2.2 Hz, 1H), 7.59 (ddd, J=8.6, 4.8, 2.3 Hz, 1H), 6.84 (t, J=9.1 Hz, 1H), 4.42 (d, J=0.7 Hz, 2H).

tert-Butyl (5-bromo-2-(trifluoromethyl)benzyl) carbamate (90). Compound 89 (0.500 g, 2.00 mmol) was diluted in anhydrous THF (7 mL) and cooled to 0° C. Borane-dimethylsulfide (0.684 g, 9.00 mmol, 0.854 mL) was added dropwise.11 The mixture was warmed to r.t. and then heated at reflux for 17 h. The mixture was then cooled, and methanolic HCl (3 M, 7 mL) was added. The mixture was heated at reflux for 30 min, cooled, and concentrated. The residue was diluted with $H_2O$ (20 mL) and basified with 1 M NaOH (to pH 12), and extracted with EtOAc (3×20 mL). The organic phase was washed with sat. aq. NaCl (50 mL), dried over anhydrous sodium sulfate, and concentrated. The residue was passed through a short $SiO_2$ plug and washed with EtOAc; then the solution was concentrated and the residue diluted in THF (20 mL). $Boc_2O$ (0.436 g, 2.00 mmol) was added as a solution in minimal THF, and the mixture was stirred at r.t. for 75 min. Concentration afforded a residue that was purified by flash column chromatography, eluting with a gradient of hexanes to 20% EtOAc in hexanes to afford the product as colorless crystals (0.577 g, 81%) after drying in vacuo: mp 54.5-58° C. $^{1}$H-NMR (500 MHz; $CDCl_3$): δ 7.71 (s, 1 H), 7.52-7.48 (m, 2H), 4.92 (s, 1H), 4.48 (d, J=5.7 Hz, 2H), 1.47 (s, 9H); $^{13}$C-NMR (126 MHz; $CDCl_3$): δ 155.8, 139.8, 132.6, 130.5, (127.6+127.58+127.54+127.49, 1 C), (127.41+125.2+123.1+120.9, 1 C), 127.01, 80.2, 40.8, 28.4 (3 C); LC-TOF ESI m/z 376/378 (MNa+).

3-Bromo-2-ethylbenzaldehyde (92a) and 5-Bromo-2-ethylbenzaldehyde (92b).12 Compound 91 (0.500, 3.72 mmol) was diluted in anhydrous CH2Cl2 (2.5 mL). AlCl3 (0.867 g, 6.59 mmol) was added, and the mixture was cooled to 0° C. and stirred 10 min. Bromine (0.190 mL, 3.72 mmol) in CH2Cl2 (3 mL) was added over 6 h via syringe pump, and the mixture was then warmed to r.t. and stirred for 16 h. The mixture was poured into crushed ice and $H_2O$ (100 mL), and the suspension was extracted with CH2Cl2 (3×50 mL). The organic layer was washed with 2 M HCl, sat. aq. $NaHCO_3$, and sat. aq. NaCl (50 mL each), dried over anhydrous sodium sulfate, and concentrated to yield a residue that was purified by flash column chromatography, eluting with a gradient of hexanes to 35% CH2Cl2 in hexanes, to yield a yellow oil (0.509 g, 64%) that was a 3:1 mixture of pure 92b (major) and 92a (minor). This compound was reduced immediately.

(5-Bromo-2-ethylphenyl) methanol (93). The mixture of 92b and 92a (0.509 g, 2.39 mmol) was diluted in MeOH (25 mL). NaBH4 (0.110 g, 2.87 mmol) was added, and the mixture was stirred for 18 h at r.t. and then concentrated. The residue was partitioned between EtOAc and 5% aq. NaCl (25 mL each). The layers were separated, and the aqueous layer was extracted with EtOAc (2×25 mL). The organic layer was washed with sat. aq. NaCl (50 mL), dried over anhydrous sodium sulfate, and concentrated. The residue was purified by flash column chromatography, eluting with a gradient of hexanes to 20% EtOAc in hexanes to afford compound 93 (0.342 g, 67%), which was chlorinated without further characterization.

4-Bromo-2-(chloromethyl)-1-ethylbenzene (94). Compound 93 (0.342 g, 1.59 mmol) was diluted in anhydrous CH2Cl2 (10 mL) and cooled to 0° C. SOCl2 (0.461 mmol, 6.36 mmol) was added dropwise under argon, and the mixture was warmed to r.t., stirred 90 min, heated at reflux for 90 min, and then stirred at r.t. for 20 h. The mixture was concentrated, azeotroped with toluene twice, and the residue was purified by flash column chromatography, eluting with a gradient of hexanes to 20% EtOAc in hexanes to yield 94 as a clear, colorless oil (0.151 g, 41%) that was immediately used without further characterization.

4-Bromo-2-(bromomethyl)-1-ethoxybenzene (100). Compound 99 (0.608 g, 2.82 mmol) and NBS (0.528, 2.96 mmol) were diluted in CCl4 (25 mL), and $(PhCO_2)_2$ (~20 mg) was added. The mixture was heated at reflux for 20 h, cooled, and diluted with hexanes (20 mL). The insoluble precipitate was filtered, and the filtrate was concentrated. The residue was purified by flash column chromatography, eluting with hexanes. Fractions containing 100 were concentrated and re-purified by column chromatography, eluting with a gradient of hexanes to 5% EtOAc in hexanes, and pure 100 (0.356 g, 43%) was obtained as a white wax, >90% pure by NMR spectrometry and suitable for use in the next step without further purification.

General Procedure 1: Delépine Reaction of Benzyl Halides and Amine Protection. Step 1. The requisite benzyl halide (1 equiv), hexamethylenetetramine (1 equiv), and NaI (1 equiv) were diluted in absolute EtOH (12 mL/mmol), and the mixture was stirred at r.t. for 20-84 h (typically overnight), upon which a white precipitate formed. Conc. HCl (3-4 mL/mmol of halide) was added, and the mixture was heated at reflux for 2 h. After cooling, the mixture was concentrated, and the residue was partitioned between EtOAc and $H_2O$ (30 mL each). The EtOAc layer was extracted with 2 M HCl (typically 2-3×20 mL), and the combined aqueous layers were washed with EtOAc (2×30 mL). The aqueous layer was then basified with 2 M aq. NaOH until the pH was approximately 12, and extracted with EtOAc (with at least 100 mL/mmol). The organic phase was washed with sat. aq. NaCl, dried over anhydrous sodium sulfate, and concentrated to yield the crude amine, which was diluted in THF (5 mL/mmol).

Step 2. $Boc_2O$ (1-1.1 equiv) was added as a solution in minimal THF. The mixture was stirred at least 1 h at r.t. and then concentrated, and the residue was purified by flash column chromatography (as described below under subheadings for the individual compounds) to yield the desired carbamate.

tert-Butyl(2-fluoro-5-iodobenzyl) carbamate (87). Using General Procedure 1, Compound 85 (0.455 g, 1.44 mmol) yielded 87 as a clear, colorless syrup (0.330 g, 65%) after purification by flash column chromatography, eluting with a gradient of hexanes to 20% EtOAc in hexanes, and drying in vacuo. This product was used immediately without further characterization or purification. $^1$H-NMR (500 MHz; $CDCl_3$): δ 7.63 (dd, J=6.8, 1.9 Hz, 1H), 7.54 (ddd, J=8.1, 5.1, 2.6 Hz, 1H), 6.80 (t, J=9.2 Hz, 1H), 4.87 (br s, 1H), 4.32 (br d, J=4.9 Hz, 2H), 1.46 (s, 9H).

tert-Butyl(2-chloro-5-iodobenzyl) carbamate (88). Using General Procedure 1, Compound 86 (0.300 g, 0.905 mmol) yielded 88 as a clear, colorless syrup that solidified upon standing (0.263 g, 79%) after purification by flash column chromatography, eluting with a gradient of 5% EtOAc hexanes to 25% EtOAc in hexanes, and drying in vacuo. This product was used immediately without further characterization or purification. $^1$H-NMR (500 MHz; $CDCl_3$): δ 7.68 (d, J=2.1 Hz, 1H), 7.52 (dd, J=8.3, 2.1 Hz, 1H), 7.08 (d, J=8.3 Hz, 1H), 4.96 (br s, 1H), 4.35 (br d, J=5.8 Hz, 2H), 1.46 (s, 9H).

tert-Butyl (5-bromo-2-ethylbenzyl) carbamate (95). Using General Procedure 1, Compound 94 (0.151 g, 0.647 mmol) yielded 95 as a white solid (0.072 g, 35%) after purification by flash column chromatography, eluting with a gradient of 5% EtOAc in hexanes to 20% EtOAc in hexanes, and drying in vacuo: mp 60.5-61.5° C. $^1$H-NMR (500 MHz; $CDCl_3$): δ 7.38 (s, 1H), 7.34 (dd, J=8.1, 1.9 Hz, 1H), 7.06 (d, J=8.1 Hz, 1H), 4.70 (br s, 1H), 4.32 (br d, J=5.1 Hz, 2 H), 2.61 (q, J=7.5 Hz, 2H), 1.47 (s, 9H), 1.20 (t, J=7.6 Hz, 3H); $^{13}$C-NMR (126 MHz; $CDCl_3$): δ 155.6, 141.1, 138.2, 130.8, 130.60, 130.40, 119.7, 79.8, 41.7, 28.4 (3 C), 24.9, 15.0; LC-TOF ESI m/z 336/338 (MNa+).

tert-Butyl (5-bromo-2-methoxybenzyl) carbamate (98). Using General Procedure 1, -Compound 97 (0.200 g, 0.849 mmol) yielded 98 as a white, waxy crystalline solid (0.194 g, 72%) after purification by flash column chromatography, eluting with a gradient of hexanes to 40% EtOAc in hexanes, and drying in vacuo. The spectral data for this compound are identical to those previously reported. 13 tert-Butyl (5-bromo-2-ethoxybenzyl) carbamate (101). Using General Procedure 1, Compound 100 (0.294 g, 1.00 mmol) yielded 101 as a white waxy solid (0.250 g, 76%) after purification by flash column chromatography, eluting with a gradient of hexanes to 40% EtOAc in hexanes, and drying in vacuo: mp 80-81° C. $^1$H-NMR (500 MHz; $CDCl_3$): δ 7.36 (s, 1H), 7.31 (dd, J=8.6, 2.5 Hz, 1H), 6.70 (d, J=8.7 Hz, 1H), 4.94 (br s, 1H), 4.28 (br d, J=5.7 Hz, 2H), 4.02 (q, J=7.0 Hz, 2H), 1.45 (s, 9H), 1.42 (t, J=7.0 Hz, 3H). $^{13}$C-NMR (126 MHz; $CDCl_3$): δ 155.83, 155.82, 131.6, 131.0, 129.5, 112.74, 112.60, 79.5, 63.9, 39.9, 28.4 (3 C), 14.8; LC-TOF ESI m/z 352/354 (MNa+).

tert-Butyl (5-bromo-2-hydroxybenzyl) carbamate (103). Compound 102 (1.19 g, 6 mmol) was diluted in anhydrous THF (10 mL) and cooled to 0° C. Borane-dimethylsulfide (2.05 g, 27 mmol, 2.55 mL) was added dropwise. The mixture was warmed to r.t. and then heated at reflux for 18 h. The mixture was then cooled, and methanolic HCl (3 M, 12 mL) was added. The mixture was heated at reflux for 30 min, cooled, and concentrated. The residue was purified by cation-exchange chromatography (Dowex 50WX8-400 H+ form resin), washing with MeOH and eluting with 2 M $NH_3$ in MeOH. The fraction containing the intermediate hydroxybenzylamine by TLC was concentrated, and the residue was diluted in 4:1 THF/MeOH (80 mL). $Boc_2O$ (0.736 g, 3.42 mmol) was added as a solution in 5 mL THF, and the mixture was stirred at r.t. for 18 h and concentrated. The residue was purified by flash column chromatography, eluting with a gradient of 5% EtOAc in hexanes to 35% EtOAc in hexanes to yield 103 as a white crystalline solid (0.931 g, 51%): mp 126.5-127.2° C. $^1$H-NMR (500 MHz; $CDCl_3$): δ 9.10 (s, 1H), 7.28 (dd, J=8.6, 2.4 Hz, 1H), 7.17 (d, J=2.4 Hz, 1H), 6.82 (d, J=8.6 Hz, 1H), 5.26 (br s, 1H), 1.44 (s, 9H); $^{13}$C-NMR (126 MHz; $CDCl_3$): δ 158.5, 155.1, 133.1, 132.5, 127.0, 119.8, 111.4, 81.7, 40.9, 28.3 (3 C); LC-TOF ESI m/z 324/326 (MNa+).

General Procedure 2: Ether formation from 103. NaH (1 equiv of a 60% dispersion in mineral oil) was diluted with anhydrous DMF (1.5 mL/mmol) and cooled to 0° C. under argon. A solution of 103 (1 equiv) in anhydrous DMF was added dropwise, and the mixture was stirred at 0° C. for 25 min. The alkyl or benzyl halide (1.1-2 equiv) was then added dropwise (liquids were added directly, whereas solids or free-based pyridines were added as a solution in minimal DMF). The mixture was allowed to warm to r.t. and stirred overnight (or warmed if necessary). The reaction was quenched by adding a mixture of $H_2O$ and sat. aq. NaHCO3 (1:1, 10 mL/mmol of 103). The mixture was then extracted with EtOAc (3×30 mL), and the organic layers were washed with 5% aq. NaCl (3×50 mL) and sat. aq. NaCl (50 mL) and dried over anhydrous sodium sulfate. Concentration afforded a residue that was purified by flash column chromatography (as described below under subheadings for the individual compounds) to yield the desired carbamate.

tert-Butyl (5-bromo-2-propoxybenzyl) carbamate (104). Following General Procedure 2, compound 103 (0.151 g, 0.50 mmol) and 1-iodopropane (0.127 g, 0.75 mmol) yielded 104 as a white flocculent solid (0.138 g, 80%) after purification by flash column chromatography, eluting with a gradient of hexanes to 35% EtOAc in hexanes. This product was used immediately without further characterization or purification. $^1$H-NMR (500 MHz; $CDCl_3$): δ 7.35 (s, 1H), 7.31 (dd, J=8.6, 2.5 Hz, 1H), 6.71 (d, J=8.7 Hz, 1H), 4.94 (br s, 1H), 4.28 (br d, J=5.6 Hz, 2H), 3.92 (t, J=6.4 Hz, 2H), 1.82 (sextet, J=6.9 Hz, 2H), 1.45 (s, 9H), 1.04 (t, J=7.4 Hz, 3H).

tert-Butyl (5-bromo-2-isopropoxybenzyl) carbamate (105). Following General Procedure 2, compound 103 (0.151 g, 0.50 mmol) and 2-iodopropane (0.170 g, 1.00 mmol) yielded 105 as a white waxy solid (0.127 g, 74%) after purification by flash column chromatography, eluting with a gradient of hexanes to 30% EtOAc in hexanes. This product was used immediately without further characterization or purification. $^1$H-NMR (500 MHz; $CDCl_3$): δ 7.35 (s, 1H), 7.30 (dd, J=8.7, 2.5 Hz, 1H), 6.72 (d, J=8.7 Hz, 1H), 4.91 (br s, 1H), 4.53 (dt, J=12.1, 6.0 Hz, 1 H), 4.26 (br d, J=5.6 Hz, 2H), 1.45 (s, 9H), 1.34 (d, J=6.1 Hz, 6H).

tert-Butyl (5-bromo-2-isobutoxybenzyl) carbamate (106). Following General Procedure 2 (stirring for four days at r.t. and then heating to 50° C. for 3 h) compound 103 (0.120 g, 0.397 mmol) and 1-iodo-2-methylpropane (0.147 g, 1.00 mmol) yielded 106 as a white waxy solid (0.045 g, 32%) after purification by flash column chromatography, eluting with a gradient of hexanes to 30% EtOAc in hexanes: mp 95.8-96.8° C. $^1$H-NMR (500 MHz; $CDCl_3$): δ 7.35 (d, J=1.9 Hz, 1 H), 7.31 (dd, J=8.6, 2.5 Hz, 1H), 6.70 (d, J=8.7 Hz, 1H), 4.92 (br s, 1H), 4.30 (br d, J=5.7 Hz, 2H), 3.72 (d, J=6.4 Hz, 2H), 2.11 (dquintet, J=13.3, 6.6 Hz, 1H), 1.45 (s, 9H), 1.03 (d, J=6.7 Hz, 6H); $^{13}$C-NMR (126 MHz; $CDCl_3$): δ 156.10, 155.94, 131.6, 131.2, 129.5, 112.78, 112.66, 79.6, 74.7, 40.1, 28.57 (3 C), 28.42, 19.5; LC-TOF ESI m/z 380/382 (MNa+)

tert-Butyl (5-bromo-2-(cyclobutylmethoxy)benzyl) carbamate (107). Compound 103 (0.154 g, 0.51 mmol) and $K_2CO_3$ (0.278 g, 2.01 mmol) were diluted in freshly distilled acetone (2.0 mL) and cooled to 0° C. After being stirred for 5 min, (2-bromomethyl)cyclobutane (0.100 mL, 0.417 mmol) was added dropwise. The mixture was warmed to r.t., purged with nitrogen, and then heated in a pressure vessel at 115° C. for 18 h. The mixture was cooled and filtered through a plug of Celite. The filter cake was washed with three portions of warm acetone before the combined filtrate was concentrated to yield a colorless oil. The residue was purified by flash column chromatography, eluting with a gradient of 5% EtOAc in hexanes to 40% EtOAc in hexanes to yield 107 as a white crystalline solid (0.137 g, 72%): mp 80.2-82.6° C.; $^1$H-NMR (500 MHz, $CDCl_3$) δ 7.35 (d, J=2.7 Hz, 1H), 7.31 (dd, J=8.6, 2.6 Hz, 1H), 6.71 (d, J=8.6 Hz, 1H), 4.96 (s, 1H), 4.28 (d, J=6.2 Hz, 2H), 3.92 (d, J=6.4 Hz, 2H), 2.78 (p, J=7.3 Hz, 1H), 2.15 (ddt, J=12.4, 8.5, 3.3 Hz, 2H), 2.05-1.91 (m, 4H), 1.45 (s, 9H); $^{13}$C-NMR (126 MHz, $CDCl_3$) δ 156.1, 155.8, 131.5, 131.0, 129.4, 112.8, 112.6, 79.4, 72.2, 40.1, 34.5, 28.4, 24.8, 18.6; LC-TOF ESI m/z 371/373 (MH+).

tert-Butyl (5-bromo-2-(cyclopropylmethoxy)benzyl) carbamate (108). Compound 103 (0.812 g, 2.69 mmol) and $K_2CO_3$ (1.49 g, 10.7 mmol) were diluted in freshly distilled acetone (9.0 mL) and cooled to 0° C. After stirring for 5 min, (2-bromomethyl)cyclopropane (0.326 mL, 3.36 mmol) was added dropwise. The mixture was warmed to r.t., purged with nitrogen, and heated in a pressure vessel at 115° C. for 18 h. The mixture was cooled and filtered through a plug of Celite. The filter cake was washed with three portions of warm acetone before the combined filtrate was concentrated to yield a colorless oil. The residue was purified by flash column chromatography, eluting with a gradient of 5% EtOAc in hexanes to 40% EtOAc in hexanes to yield 108 as a white crystalline solid (0.907 g, 95%): mp 73.8-76.2° C.; $^1$H-NMR (500 MHZ, $CDCl_3$) δ 8.84 (s, 1H), 7.90 (d, J=1.0 Hz, 1H), 7.40 (d, J=2.5 Hz, 1H), 7.35 (dd, J=8.6, 2.5 Hz, 1H), 6.81 (d, J=8.7 Hz, 1H), 5.29 (d, J=0.8 Hz, 2H), 4.88 (s, 1H), 4.27 (d, J=6.3 Hz, 2H), 1.44 (s, 9H); 13C-NMR (126 MHz, $CDCl_3$) δ 155.7, 154.7, 154.3, 142.5, 133.5, 131.9, 131.1, 130.1, 114.0, 113.2, 79.6, 62.8, 39.7, 28.4; LC-TOF ESI m/z 356/358 (MH+).

tert-Butyl (5-bromo-2-((3-fluorobenzyl)oxy)benzyl) carbamate (109). Following General Procedure 2, compound 104 (0.105 g, 0.35 mmol) and 3-fluorobenzyl bromide (0.073 g, 0.385 mmol) yielded 109 as a white waxy solid (0.109 g, 76%) after purification by flash column chromatography, eluting with a gradient of hexanes to 20% EtOAc in hexanes. This product was used immediately without further characterization or purification. $^1$H-NMR (500 MHz; $CDCl_3$): δ 7.40 (d, J=1.8 Hz, 1H), 7.38-7.30 (m, 2H), 7.17 (d, J=7.6 Hz, 1H), 7.11 (d, J=9.4 Hz, 1H), 7.03 (td, J=8.4, 2.4 Hz, 1H), 6.75 (d, J=8.7 Hz, 1H), 5.07 (s, 2H), 4.93 (br s, 1H), 4.34 (br d, J=5.5 Hz, 2H), 1.45 (s, 9H).

tert-Butyl (5-bromo-2-((4-cyanobenzyl)oxy)benzyl) carbamate (110). Following General Procedure 2, compound 103 (0.151 g, 0.50 mmol) and 4-cyanobenzyl bromide (0.098 g, 0.5 mmol) yielded 110 as a white solid (0.169 g, 81%) after purification by flash column chromatography, eluting with a gradient of 10% EtOAc in hexanes to 35% EtOAc in hexanes: mp 130-131.5° C. $^1$H-NMR (500 MHz; $CDCl_3$): δ 7.69 (d, J=8.2 Hz, 2H), 7.52 (d, J=8.1 Hz, 2H), 7.41 (d, J=2.4 Hz, 1H), 7.32 (dd, J=8.7, 2.4 Hz, 1H), 6.72 (d, J=8.7 Hz, 1H), 5.13 (s, 2H), 4.88 (s, 1H), 4.36 (d, J=5.4 Hz, 2H), 1.45 (s, 9H); $^{13}$C-NMR (126 MHz; $CDCl_3$): δ 155.8, 154.8, 141.8, 132.6, 131.7, 131.2, 129.8, 127.42, 118.6, 113.8, 113.1, 112.0, 79.8, 69.2, 39.7, 28.43, 28.37; LC-TOF ESI m/z 417/419 (MH+).

tert-Butyl (5-bromo-2-(pyridin-2-ylmethoxy)benzyl) carbamate (111). Following General Procedure 2, compound 103 (0.151 g, 0.50 mmol) and 3-pyridylmethyl bromide HBr (0.140 g, 0.55 mmol, free-based with an equivalent of NaH in DMF at 0° C. for the last 10 min of phenoxide formation) yielded 113 as a white waxy solid (0.173 g, 88%) after purification by flash column chromatography, eluting with a gradient of 10% EtOAc in hexanes to 80% EtOAc in hexanes: mp 117.5-118° C. $^1$H-NMR (500 MHz; $CDCl_3$): δ 8.59 (d, J=4.5 Hz, 1H), 7.70 (td, J=7.7, 1.7 Hz, 1H), 7.43-7.41 (m, 1H), 7.38 (s, 1H), 7.29 (dd, J=8.7, 2.5 Hz, 1H), 7.23-7.21 (m, 1H), 6.76 (d, J=8.7 Hz, 1H), 5.49 (br s, 1H), 5.20 (s, 2H), 4.36 (br d, J=5.9 Hz, 2H), 1.44 (s, 9H); $^{13}$C-NMR (126 MHz; $CDCl_3$): δ 156.4, 156.0, 155.3, 149.4, 137.0, 131.9, 131.2, 129.9, 122.9, 121.2, 113.51, 113.45, 79.4, 70.8, 40.1, 28.5 (3 C); LC-TOF ESI m/z 393/395 (MH+).

tert-Butyl (5-bromo-2-(pyridin-3-ylmethoxy)benzyl) carbamate (112). Following General Procedure 2, compound 103 (0.103 g, 0.341 mmol) and 2-pyridylmethyl bromide HBr (0.095 g, 0.375 mmol, free-based with an equivalent of NaH in DMF at 0° C. for the last 10 min of phenoxide formation) yielded 112 as a white waxy solid (0.134 g, 99%) after purification by flash column chromatography, eluting with a gradient of 10% EtOAc in hexanes to 60% EtOAc in hexanes: mp 115-116° C. $^1$H-NMR (500 MHz; $CDCl_3$): δ 8.67 (d, J=1.6 Hz, 1H), 8.61 (dd, J=4.8, 1.4 Hz, 1H), 7.76 (d, J=7.7 Hz, 1H), 7.40 (d, J=2.3 Hz, 1H), 7.35-7.33 (m, 2H), 6.79 (d, J=8.7 Hz, 1H), 5.09 (s, 2H), 4.88 (br s, 1H), 4.32 (br d, J=5.5 Hz, 2H), 1.44 (s, 9H); 13C-NMR (126 MHz; $CDCl_3$): δ 155.8, 155.1, 149.7, 148.8, 135.1, 132.0, 131.7, 131.1, 129.8, 123.7, 113.7, 113.1, 79.7, 67.9, 39.7, 28.4 (3 C); LC-TOF ESI m/z 393/395 (MH+).

tert-Butyl (5-bromo-2-((5-methylisoxazol-3-yl) methoxy) benzyl) benzyl) carbamate (113). Compound 103 (0.154 g, 0.51 mmol) and $K_2CO_3$ (0.270 g, 2.0 mmol) were diluted in freshly distilled acetone (1.3 mL) and cooled to 0° C. After being stirred for 5 min, 3-chloromethyl-5-methylisoxazole (0.078 g, 0.60 mmol) was added to the reaction. The mixture was warmed to r.t., purged with nitrogen, and heated in a pressure vessel at 115° C. for 18 h. The mixture was cooled and filtered through a plug of Celite. The filter cake was washed with three portions of warm acetone before the combined filtrate was concentrated to yield a white solid. The residue was purified by flash column chromatography, eluting with a gradient of 5% EtOAc in hexanes to 60% EtOAc in hexanes to yield 113 as a white crystalline solid (0.168 g, 83%): mp 126.5-127.6° C.; $^1$H-NMR (500 MHz, $CDCl_3$) δ 7.38 (d, J=2.5 Hz, 1H), 7.33 (dd, J=8.7, 2.5 Hz, 1H), 6.82 (d, J=8.7 Hz, 1H), 6.09 (s, 1H), 5.12 (s, 2H), 4.95 (s, 1H), 4.30 (d, J=6.2 Hz, 2H), 2.43 (s, 3H), 1.45 (s, 9H); $^{13}$C-NMR (126 MHz, $CDCl_3$) δ 170.4, 160.3, 155.8, 154.8, 131.8, 131.2, 129.8, 113.8, 113.2, 100.8, 79.4, 62.1, 39.8, 28.4, 12.3; LC-TOF ESI m/z 398/400 (MH+).

tert-Butyl (5-bromo-2-(thiazol-4-ylmethoxy)benzyl) carbamate (114). Compound 103 (0.166 g, 0.56 mmol) and $K_2CO_3$ (0.398 g, 2.88 mmol) were diluted at r.t. in anhydrous DMF (1.5 mL). After being stirred for 15 min under a nitrogen stream, 4-(chloromethyl) thiazole hydrochloride (0.122 g, 0.72 mmol) was added to the reaction vessel, which was purged with nitrogen and sealed. The mixture was stirred for 18 h with continuous heating at 70° C. The mixture was cooled and filtered through a plug of Celite. The filter cake was washed with three portions of warm ethyl acetate. The combined filtrate was concentrated under reduced pressure to yield a dark oily residue. The residue was purified by flash column chromatography, eluting with a gradient of 5% EtOAc in hexanes to 50% EtOAc in hexanes to yield 114 as a white solid (0.177 g, 79%): mp 92.1-93.9° C.; $^{1}$H-NMR (500 MHZ, $CDCl_3$) δ 8.83-8.79 (m, 1H), 7.40-7.35 (m, 2H), 7.31 (dd, J=8.6, 2.5 Hz, 1H), 6.81 (d, J=8.7 Hz, 1H), 5.25 (s, 2H), 4.32 (d, J=6.2 Hz, 2 H), 1.43 (s, 9H); $^{13}$C-NMR (126 MHZ, $CDCl_3$) δ 155.9, 155.3, 153.5, 152.9, 132.0, 131.2, 129.9, 116.2, 113.6, 113.6, 79.4, 66.6, 40.0, 28.5; LC-TOF ESI m/z 399.51/401.45 (MH+).

tert-Butyl (5-bromo-2-(oxazol-4-ylmethoxy)benzyl) carbamate (115). Compound 103 (0.556 g, 1.8 mmol) and $Cs_2CO_3$ (1.25 g, 3.8 mmol) were diluted at r.t. in anhydrous DMF (9.0 mL). After being stirred for 30 min under a nitrogen stream, 4-(chloromethyl) oxazole hydrochloride (0.252 g, 2.2 mmol) was added to the mixture. The reaction vessel was sealed under nitrogen and left to stir at r.t. for 18 h. After 18 h of continuous stirring, a second portion of 4-(chloromethyl) oxazole hydrochloride (0.055 g, 0.47 mmol) was added to the mixture, and stirring was continued for an additional 18 h. The mixture was poured into 100 mL of sat. aq. $NaHCO_3$ solution and extracted with four 100 mL portions of EtOAc. The organic fractions were combined and washed once with sat. aq. NaCl, dried over anhydrous sodium sulfate, and concentrated to yield an oily residue. The residue was purified by flash column chromatography, eluting with a gradient of 5% EtOAc in hexanes to 55% EtOAc in hexanes to yield 115 as a yellow semi-solid (0.401 g, 57%): mp 94.1-95.7° C.; $^{1}$H-NMR (500 MHZ, $CDCl_3$) δ 7.91 (s, 2H), 7.75 (s, 2H), 7.39 (d, J=2.5 Hz, 2H), 7.34 (dd, J=8.7, 2.5 Hz, 2H), 6.84 (d, J=8.7 Hz, 2H), 5.16 (s, 2H), 5.05 (d, J=1.0 Hz, 4H), 4.29 (d, J=6.2 Hz, 3H), 2.96 (s, 1H), 2.88 (s, 1H), 1.44 (s, 17H); 13C NMR (126 MHz, $CDCl_3$) δ 162.5, 155.8, 155.2, 151.5, 136.8, 136.3, 132.1, 131.2, 130.1, 113.6, 79.5, 62.9, 39.9, 36.5, 31.4, 28.4; LC-TOF ESI m/z 384/386 (MH+).

tert-Butyl (5-bromo-2-(thiazol-5-ylmethoxy)benzyl) carbamate (116). Compound 103 (0.303 g, 1.0 mmol) and $Cs_2CO_3$ (0.966 g, 3.0 mmol) were diluted at r.t. in anhydrous DMF (5.0 mL). After being stirred for 30 min under a nitrogen stream, 5-(chloromethyl)-1,3-thiazole hydrochloride (0.252 g, 1.5 mmol) was added to the mixture. The reaction vessel was sealed under nitrogen and left to stir at r.t. for 18 h. The mixture was poured into 10 mL of sat. aq. $NaHCO_3$ solution and extracted with four 10 mL portions of EtOAc. The organic fractions were combined and washed once with brine, dried over sodium sulfate, and concentrated to an oily residue. The residue was purified by flash column chromatography, eluting with a gradient of 5% EtOAc in hexanes to 60% EtOAc in hexanes to yield 116 as a white crystalline solid (0.284 g, 71%): mp 116.2-118.6° C.; $^{1}$H-NMR (500 MHZ, $CDCl_3$) δ 8.84 (s, 1H), 7.90 (d, J=1.0 Hz, 1H), 7.40 (d, J=2.5 Hz, 1H), 7.35 (dd, J=8.6, 2.5 Hz, 1H), 6.81 (d, J=8.7 Hz, 1H), 5.29 (d, J=0.8 Hz, 2H), 4.88 (s, 1H), 4.27 (d, J=6.3 Hz, 2H), 1.44 (s, 9H); 13C NMR (126 MHz, $CDCl_3$) δ 155.7, 154.7, 154.3, 142.5, 133.5, 131.9, 131.1, 130.1, 114.0, 113.2, 79.6, 62.8, 39.7, 28.4; LC-TOF ESI m/z 399.5/401.5 (MH+).

REFERENCES AND NOTES (1) Halgren, T. A. Merck molecular force field. I. Basis, form, scope, parameterization, and performance of MMFF94. *J. Comput. Chem.* 1996, 17, 490-519.

(2) Labute P. The generalized Born/volume integral implicit solvent model: Estimation of the free energy of hydration using London dispersion instead of atomic surface area. *J. Comput. Chem.* 2008, 29, 1693-1698.

(3) Wang, J.; Wolf, R. M.; Caldwell, J. W.; Kollman, P. A.; Case, D. A. Development and testing of a general amber force field. *J. Comput. Chem.* 2004, 25, 1157-1174.

(4) Molecular Operating Environment (MOE), 2013.08; Chemical Computing Group ULC, 1010 Sherbrooke St. West, Suite #910, Montreal, QC, Canada, H3A 2R7, 2018

(5) Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. *Acta Crystallogr. D Biol. Crystallogr.* 2014, 70, 2667-74.

(6) Do, H. T.; Li, H.; Chreifi, G.; Poulos, T. L.; Silverman, R. B. Optimization of blood-brain barrier permeability with potent and selective human neuronal nitric oxide synthase inhibitors having a 2-aminopyridine scaffold. *J. Med. Chem.* 2019, 62, 2690-2707.

(7) Pensa, A. V.; Cinelli, M. A.; Li, H.; Chreifi, G.; Mukherjee, P.; Roman, L. J.; Martasek, P.; Poulos, T. L.; Silverman, R. B. Hydrophilic, potent, and selective 7-substituted 2-aminoquinolines as improved human neuronal nitric oxide synthase inhibitors. *J. Med. Chem.* 2017, 60, 7146-7165.

(8) Besnard, J.; Ruda, G. F.; Setola, V.; Abecassis, K.; Rodriguiz, R. M.; Huang, X. P.; Norval, S.; Sassano, M. F.; Shin, A. I.; Webster, L. A.; Simeons, F. R.; Stojanovski, L.; Prat, A.; Seidah, N. G.; Constam, D. B.; Bickerton, G. R.; Read, K. D.; Wetsel, W. C.; Gilbert, I. H.; Roth, B. L.; Hopkins, A. L. Automated design of ligands to polypharmacological profiles. *Nature* 2012, 492, 215-20.

(9) Hebeisen, P.; Weiss, U.; Staempfli, A.; Ring opening of cyclic sulfamidates with bromophenyl metal reagents: complementarity of sulfamidates and aziridines. *Tetrahedron Lett.* 2011, 52, 5229-4233.

(10) Moradi, A. W.; Mueller, T. N.; Murata, T.; Hutazawa, M.; Bruechner, P.; Shimojo, E.; Ichihara, T.; Ataka, M.; Shibuya, K.; and Goergens, U. Process for the preparation of pyrrolines from gamma-nitroketones. Use of gamma-nitroketones as pesticidal agents. WO 2011128299, Oct. 20, 2011.

(11) Heil, M.; Heilmann, E. K.; Sudau, A.; Kapferer, T.; Muhlthau, F. A.; Jeschke, P.; Voerste, R.; Gorgens, U.; Raming, K.; Ebbinghaus-Kinstscher, U.; Drewes, M.; Adamczewski, M.; Becker, A. Halogenalkyl-substituted amides used as insecticides and acaricides. WO2011054436, Jul. 7, 2010.

(12) Brunton, S. A.; Guicherit, O. M.; Kruse, L. I.; Haydar, S. N.; and Springer, D. M. Small organic molecule regulators of cell proliferation. WO2008057469, May 15, 2008.

(13) Lalwani, K. G.; and Sudalai, A. A concise enantioselective synthesis of (+)-L-733,060 and (+)-T-2328 via sequential proline catalysis. *Syn lett* 2016, 27, 1339-1343.

We claim:

1. A compound of a formula:

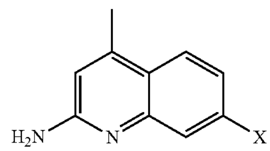

or a salt or solvate thereof, wherein:

X is selected from alkyl-amino substituted phenyl, alkyl-amino substituted pyridyl, isoindolinyl, and amino-substituted indanyl; and optionally X is substituted or further substituted with a substituent selected from cyano, halo, alkyl, haloalkyl, alkoxy, and substituents having a formula —$OCH_2$—Y, wherein Y is cycloalkyl, aryl, or heteroaryl and wherein Y is optionally substituted with a substituent selected from alkyl, halo, and cyano;

provided that the compound is not

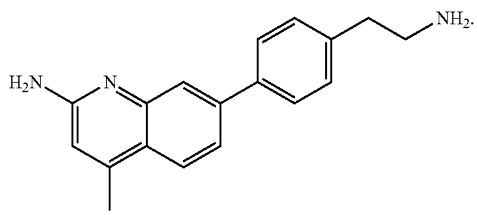 [SMILES: Cc1cc(N)nc2cc(-c3ccc(CCN)cc3)ccc12]

2. The compound of claim 1, wherein X is alkyl-amino substituted phenyl, and optionally X is substituted or further substituted with a substituent selected from cyano, halo, alkyl, haloalkyl, alkoxy, and substituents having a formula —O—$CH_2$—Y, wherein Y is cycloalkyl, aryl, or heteroaryl wherein Y is optionally substituted with a substituent selected from alkyl, halo, and cyano.

3. The compound of claim 2 of a formula:

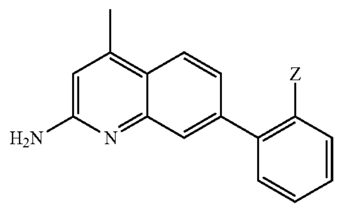

,

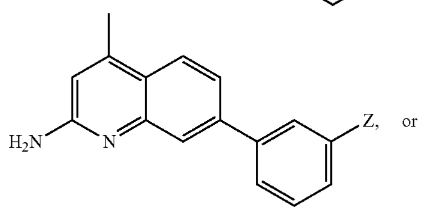

or

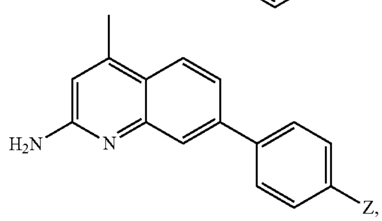

wherein:

Z is alkyl-amino.

4. The compound of claim 2 of a formula:

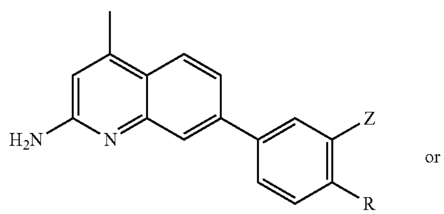

or

-continued

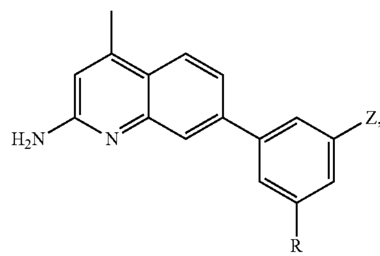

wherein:

R is selected from hydrogen, cyano, halo, alkyl, haloalkyl, alkoxy, and substituents having a formula —$OCH_2$—Y, wherein Y is cycloalkyl, aryl, or heteroaryl and wherein Y is optionally substituted with a substituent selected from alkyl halo, and cyano.

5. The compound of claim 4, wherein Z is —$CH_2NH_2$.

6. The compound of claim 5 of a formula:

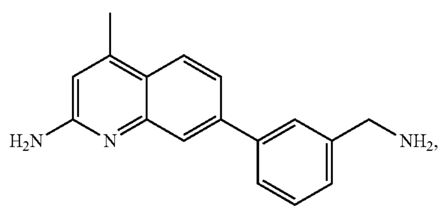

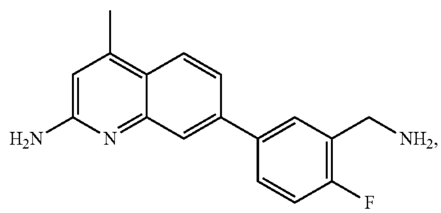 [SMILES: Cc1cc(N)nc2cc(-c3cncc(CN)c3)ccc12]

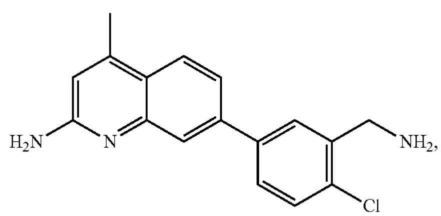

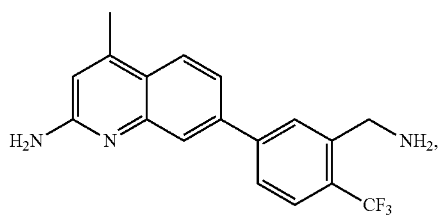

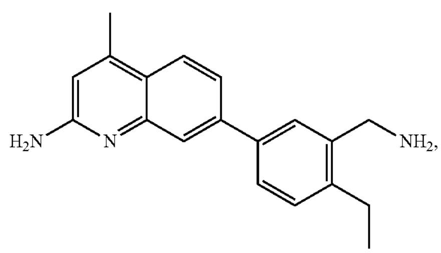

-continued
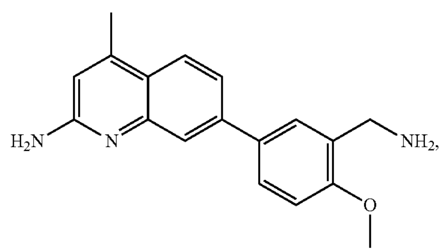
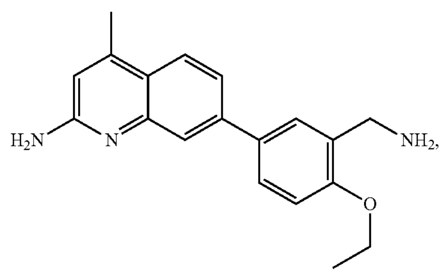
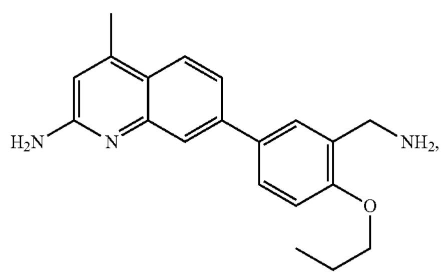
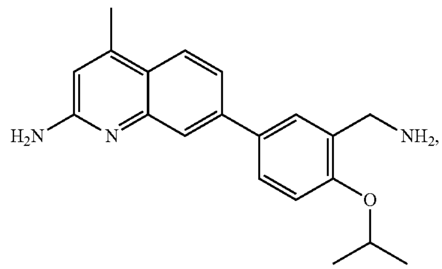
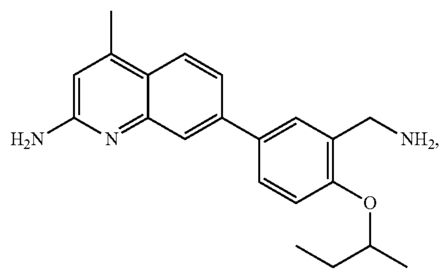
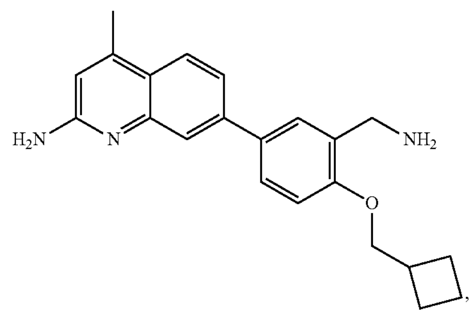
-continued
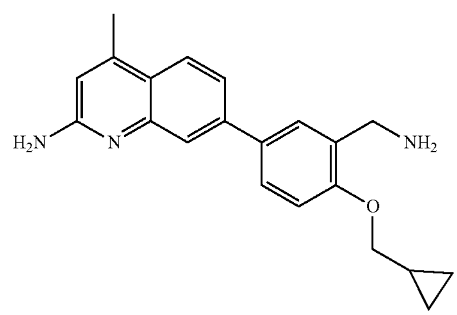
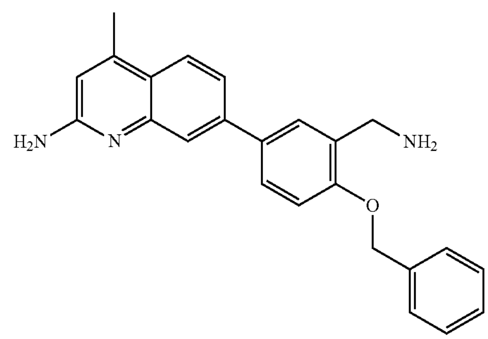
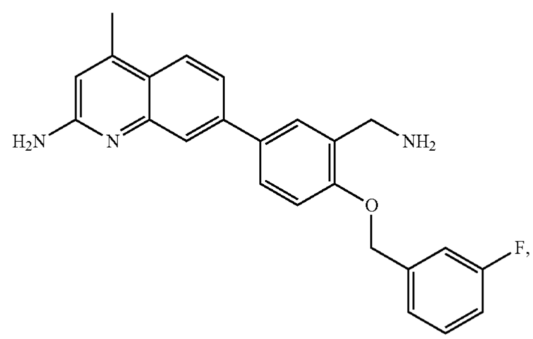
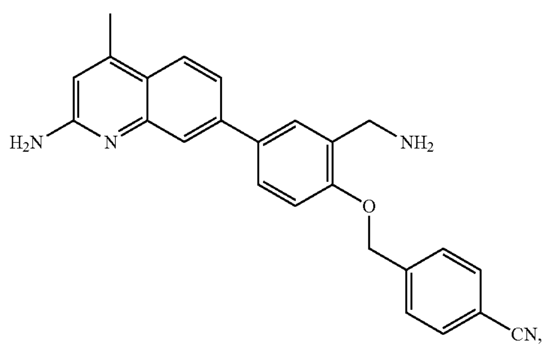
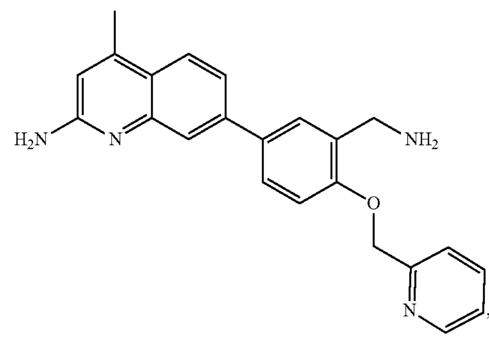

-continued

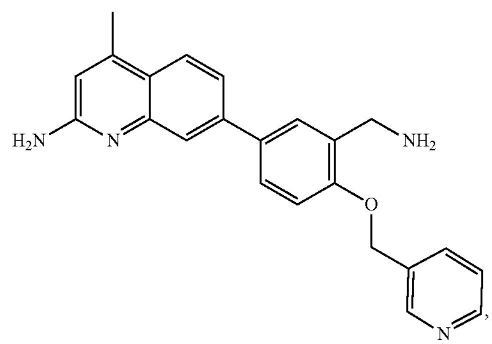

,

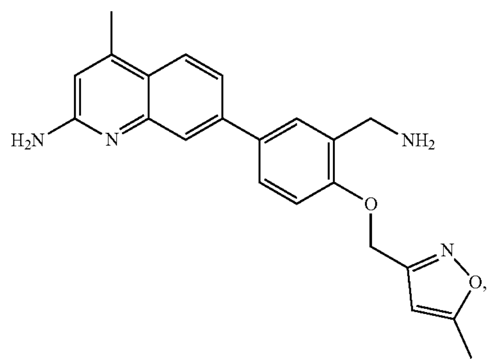

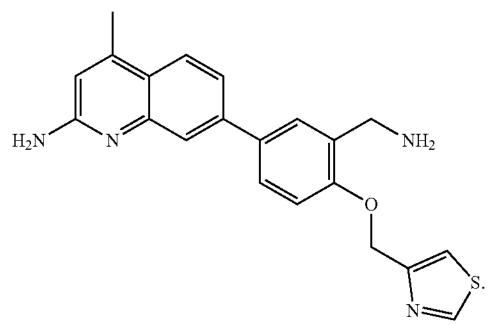

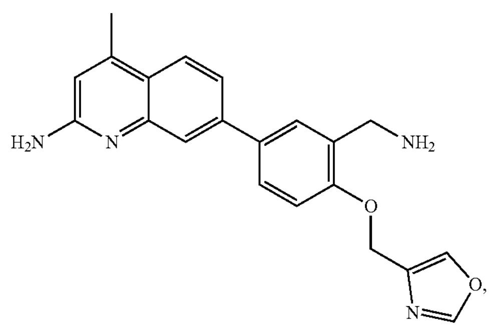

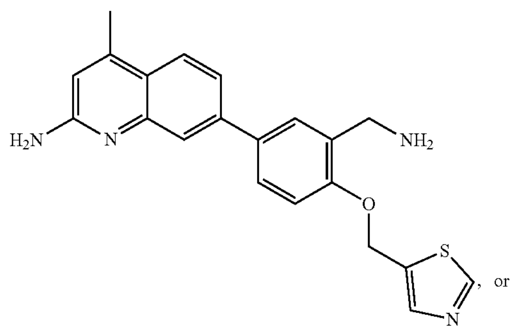

or

-continued

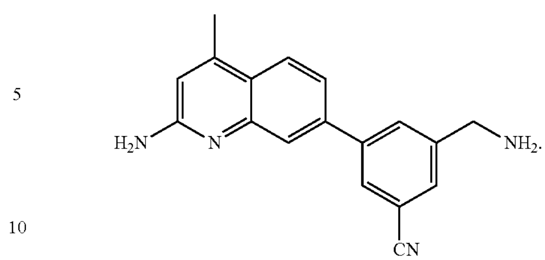

7. The compound of claim 1, wherein X is selected from alkyl-amino substituted pyridyl, isoindolinyl, and amino-substituted indanyl; and optionally X is substituted or further substituted with a substituent selected from cyano, halo, alkyl, haloalkyl, alkoxy, and substituents having a formula —$OCH_2$—Y, wherein Y is cycloalkyl, aryl, or heteroaryl and wherein Y is optionally substituted with a substituent selected from alkyl, halo, and cyano.

8. The compound of claim 7 of a formula:

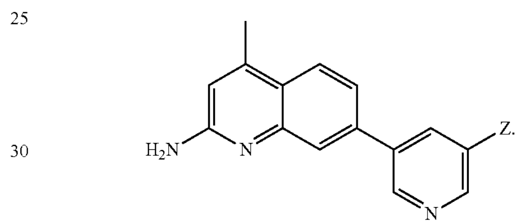

9. The compound of claim 8 of a formula:

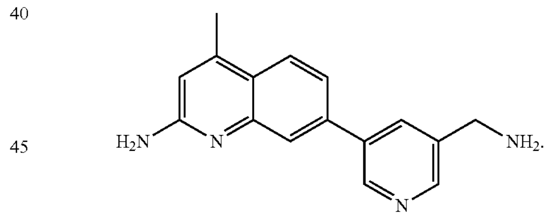

10. The compound of claim 1, wherein X is isoindolinyl.

11. The compound of claim 10 of a formula:

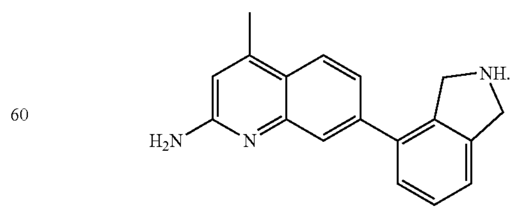

12. The compound of claim 1, wherein X is amino-substituted indanyl.

13. The compound of claim 12 of a formula:

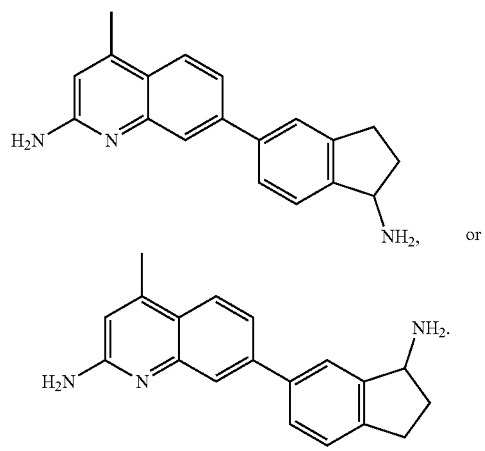

or

14. A method of treating a disease or disorder associated with nitric oxide synthase in a subject in need thereof, the method comprising administering to the subject the compound of claim 1.

15. The method of claim 14, wherein the disease or disorder is Alzheimer's disease.

16. The method of claim 14, wherein the disease or disorder is Huntington's disease.

17. The method of claim 14, wherein the disease or disorder is Parkinson's disease.

18. The method of claim 14, wherein the disease or disorder is amyotrophic lateral scleroris (ALS).

19. The method of claim 14, wherein the disease or disorder is cerebral palsy.

20. The method of claim 14, wherein the disease or disorder is a migraine.

* * * * *